(12) United States Patent
Taoda

(10) Patent No.: US 11,453,669 B2
(45) Date of Patent: Sep. 27, 2022

(54) POLYCYCLIC PYRIDONE DERIVATIVE

(71) Applicant: Shionogi & Co., Ltd., Osaka (JP)

(72) Inventor: Yoshiyuki Taoda, Osaka (JP)

(73) Assignee: SHIONOGI & CO., LTD., Osaka (JP)

( * ) Notice: Subject to any disclaimer, the term of this patent is extended or adjusted under 35 U.S.C. 154(b) by 68 days.

(21) Appl. No.: 17/058,260

(22) PCT Filed: May 30, 2019

(86) PCT No.: PCT/JP2019/021445
§ 371 (c)(1),
(2) Date: Nov. 24, 2020

(87) PCT Pub. No.: WO2019/230857
PCT Pub. Date: Dec. 5, 2019

(65) Prior Publication Data
US 2021/0155622 A1 May 27, 2021

(30) Foreign Application Priority Data
May 31, 2018 (JP) .............................. JP2018-104160

(51) Int. Cl.
*A61K 31/53* (2006.01)
*A61K 31/5365* (2006.01)
*A61P 31/18* (2006.01)
*C07D 471/14* (2006.01)
*C07D 471/22* (2006.01)
*C07D 498/14* (2006.01)
*C07D 498/22* (2006.01)

(52) U.S. Cl.
CPC ......... *C07D 471/14* (2013.01); *C07D 498/14* (2013.01); *C07D 498/22* (2013.01)

(58) Field of Classification Search
CPC ..... A61K 31/53; A61K 31/5365; A61P 31/18; C07D 471/14; C07D 471/22
See application file for complete search history.

(56) References Cited

U.S. PATENT DOCUMENTS

2013/0096109 A1    4/2013  Hattori et al.

FOREIGN PATENT DOCUMENTS

| | | |
|---|---|---|
| EP | 1 544 199 | 6/2005 |
| EP | 1 852 434 | 11/2007 |
| EP | 1 950 212 | 7/2008 |
| EP | 1 578 748 | 9/2010 |
| EP | 2 540 720 | 1/2013 |
| EP | 2 774 928 | 9/2014 |
| EP | 2 940 019 | 11/2015 |
| EP | 3 196 201 | 7/2017 |
| ID | 2016/027879 | 2/2016 |
| WO | 2004/024078 | 3/2004 |
| WO | 2005/016927 | 2/2005 |
| WO | 2006/088173 | 8/2006 |
| WO | 2006/116764 | 11/2006 |
| WO | 2007/049675 | 5/2007 |
| WO | 2011/105590 | 1/2011 |
| WO | 2011/129095 | 10/2011 |
| WO | 2013/054862 | 4/2013 |
| WO | 2014/099586 | 6/2014 |
| WO | 2014/100323 | 6/2014 |
| WO | 2014/104279 | 7/2014 |
| WO | 2014/183532 | 11/2014 |
| WO | 2014/200880 | 12/2014 |
| WO | 2015/006731 | 1/2015 |
| WO | 2015/006733 | 1/2015 |
| WO | 2015/039348 | 3/2015 |
| WO | 2015/048363 | 4/2015 |
| WO | 2015/089847 | 6/2015 |
| WO | 2015/095258 | 6/2015 |
| WO | 2015/199167 | 12/2015 |
| WO | 2016/090545 | 6/2016 |
| WO | 2016/094197 | 6/2016 |
| WO | 2016/094198 | 6/2016 |
| WO | 2016/106237 | 6/2016 |
| WO | 2016/154527 | 9/2016 |
| WO | 2016/161382 | 10/2016 |
| WO | 2016/187788 | 12/2016 |

(Continued)

OTHER PUBLICATIONS

Response to Opposition filed May 17, 2017 in European Patent No. 1950212, pp. 1-10.
Experimental Report filed in Response to Opposition to European Patent No. 1950212 filed May 11, 2017, pp. 1-38.
Further Experimental Report RE: European Patent No. 1950212 filed Oct. 26, 2017, pp. 1-2.
International Preliminary Report on Patentability dated Dec. 10, 2020 in International (PCT) Patent Application No. PCT/JP2019/021445.

(Continued)

*Primary Examiner* — Brenda L Coleman
(74) *Attorney, Agent, or Firm* — Wenderoth, Lind & Ponack, L.L.P.

(57) ABSTRACT

The present invention provides a compound represented by the following formula (I):

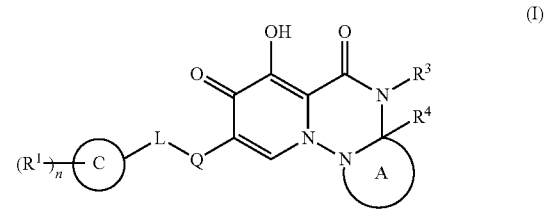

wherein, ring A is a substituted or unsubstituted non-aromatic heterocycle; ring C is a benzene ring or the like; Q is a 5-membered aromatic heterocycle or the like; each $R^1$ is independently halogen or the like; L is substituted or unsubstituted alkylene; $R^3$ is substituted or unsubstituted alkyl or the like; $R^4$ is hydrogen or the like; and n is an integer of 1 to 3.

18 Claims, No Drawings

(56) References Cited

FOREIGN PATENT DOCUMENTS

| WO | 2016/191239 | 12/2016 |
| WO | 2017/087256 | 5/2017 |
| WO | 2017/087257 | 5/2017 |
| WO | 2017/106071 | 6/2017 |
| WO | 2017/113288 | 7/2017 |
| WO | 2017/116928 | 7/2017 |
| WO | 2018/102485 | 6/2018 |
| WO | 2018/102634 | 6/2018 |
| WO | 2019/160783 | 10/2019 |
| WO | 2019/209667 | 10/2019 |
| WO | 2019/223408 | 11/2019 |
| WO | 2019/236396 | 12/2019 |
| WO | 2020/197991 | 10/2020 |

OTHER PUBLICATIONS

C.G. Wermuth, The Practice of Medicinal Chemistry, 1998, pp. 476, and 494-495, 10 total pages with English translation.
Miyazaki et al., Separation of optical isomers, 1989, pp. 16-17, 8 total pages, with English translation.

POLYCYCLIC PYRIDONE DERIVATIVE

TECHNICAL FIELD

The present invention relates to a novel compound having an antiviral effect. More specifically, the present invention relates to a polycyclic pyridone derivative having HIV integrase inhibitory activity and a medicament, particularly, an anti-HIV drug including thereof.

BACKGROUND ART

Among viruses, human immunodeficiency virus (hereinafter, abbreviated to HIV), one type of retrovirus, is known to cause acquired immunodeficiency syndrome (hereinafter, abbreviated to AIDS). Various guidelines currently recommend naive patients for a combination of an integrase inhibitor (dolutegravir, etc.) as a principal drug with two nucleic acid reverse transcriptase inhibitors (ABC+3TC, FTC+TAF, etc.) differing in resistance profile, as a therapeutic drug for this AIDS. Because of strong efficacy and high safety, these combinations have a high satisfaction level as compared with initial therapeutic drugs. Meanwhile, the start of treatment upon detection of HIV infection is recommended owing to the emergence of such a safe drug and good prognosis. In addition, a medication period becomes long because people infected with HIV have an average life expectancy closer to that of healthy people. If adverse reactions of the nucleic acid reverse transcriptase inhibitors occur or once a resistant virus appears due to the long-term medication, there is no further convenient treatment method. Therefore, there is a move afoot to leave the nucleic acid reverse transcriptase inhibitors unused. Hence, the establishment of two-drug treatment with two principal drugs is desired. Thus, the development of a principal drug that can be combined with the integrase inhibitor is desired. Furthermore, the development of a therapeutic drug with a longer medication interval, i.e., a long-acting injection with which treatment is completed merely by one injection at 1-month or longer intervals is desired for improving medication fatigue ascribable to the long-term medication and improving QOL (quality of life) of patients in such a way that the patients more enjoy daily life.

In order to meet such demands, an integrase inhibitor cabotegravir is under development as a long-acting injection at Ph3. Also, non-nucleic acid reverse transcriptase inhibitor rilpivirine is also under development as a long-acting injection. The establishment of a treatment method is being attempted using these two drugs. However, these drugs are injected once a month or two months and need to be injected at a total of 3 or 4 sites with pain. Hence, the development of a drug with which treatment is completed by one injection per 3 months with less pain at a lower dose is desired for further improving QOL of patients.

Raltegravir and elvitegravir as the first-generation oral agents and dolutegravir as the second-generation oral agent have already been launched as integrase inhibitors. When a naive patient uses dolutegravir, no resistant mutation appears. However, dolutegravir, when used in the treatment of a patient infected with a resistant virus to the first-generation integrase inhibitor, may be no longer effective due to the further addition of a resistant mutation. Hence, the development of an inhibitor having a higher resistance barrier than that of dolutegravir is also desired.

Pyridone derivatives having a heterocycle as a side chain are known as one of the anti-HIV drugs having an integrase inhibitory effect (Patent Documents 1 to 13). Among them, Patent Document 6 describes a condensed tricyclic pyridopyrazine derivative. Patent Document 4 describes a condensed tricyclic pyridopyrazine derivative and a condensed tricyclic pyridotriazine derivative.

PRIOR ART REFERENCES

Patent Document

[Patent Document 1] International Publication No. WO 2005/016927
[Patent Document 2] International Publication No. WO 2011/105590
[Patent Document 3] International Publication No. WO 2013/054862
[Patent Document 4] International Publication No. WO 2014/099586
[Patent Document 5] International Publication No. WO 2014/183532
[Patent Document 6] International Publication No. WO 2014/200080
[Patent Document 7] International Publication No. WO 2015/089847
[Patent Document 8] International Publication No. WO 2015/095258
[Patent Document 9] International Publication No. WO 2016/027879
[Patent Document 10] International Publication No. WO 2016/094197
[Patent Document 11] International Publication No. WO 2016/187788
[Patent Document 12] International Publication No. WO 2016/191239
[Patent Document 13] International Publication No. WO 2017/106071

SUMMARY OF THE INVENTION

Problems to be Solved by the Invention

An object of the present invention is to provide a novel long-acting compound having integrase inhibitory activity with a high resistance barrier.

Means for Solving the Problem

The present inventors have conducted diligent studies and consequently found that a novel pyridone derivative has an integrase inhibitory effect with a high resistance barrier. The present inventors have further discovered that the compound of the present invention and a medicament including thereof are useful as an antiviral drug (e.g., an anti-retrovirus drug, an anti-HIV drug, an anti-HTLV-1 (human T cell leukemia virus type 1) drug, an anti-FIV (feline immunodeficiency virus) drug, and an anti-SIV (simian immunodeficiency virus) drug), particularly, an anti-HIV drug, an anti-AIDS drug, or a therapeutic drug for related diseases thereof, etc., completing the present invention given below.

The present invention provides aspects given below.

[1] A compound represented by the following formula (I) or a pharmaceutically acceptable salt thereof:

[Chemical Formula 1]

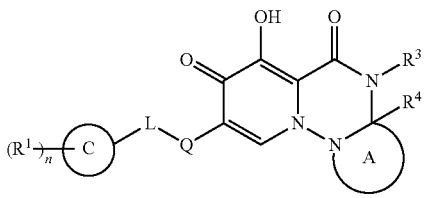
(I)

wherein
ring A is a substituted or unsubstituted non-aromatic heterocycle;
ring C is a benzene ring or a pyridine ring;
Q is a 5- or 6-membered aromatic heterocycle optionally substituted with one or more substituents selected from the group consisting of halogen, alkyl, haloalkyl, alkyloxy, haloalkyloxy, and alkylamino;
each $R^1$ is independently halogen, alkyl, haloalkyl, alkyloxy, cyano, or haloalkyloxy;
L is substituted or unsubstituted alkylene;
$R^3$ is substituted or unsubstituted alkyl, substituted or unsubstituted non-aromatic carbocyclyl, or substituted or unsubstituted non-aromatic heterocyclyl;
$R^4$ is hydrogen, or substituted or unsubstituted alkyl;
$R^3$ and $R^4$, or $R^3$ and a substituent on ring A may be taken together with the adjacent atoms to form a substituted or unsubstituted non-aromatic heterocycle; and
n is an integer of 1 to 3.

[2] The compound according to [1] or a pharmaceutically acceptable salt thereof, wherein ring A is any of the following rings:

[Chemical Formula 2]

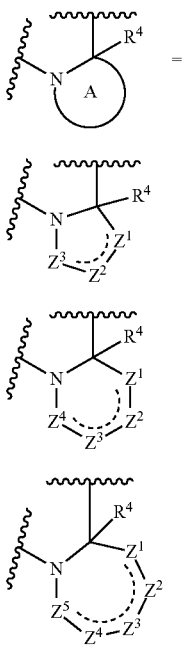

(a)

(b)

(c)

wherein
$R^4$ is hydrogen, or substituted or unsubstituted alkyl;
the broken line represents the presence or absence of a bond;

$Z^1$, $Z^2$, $Z^3$, $Z^4$ and $Z^5$ are each independently $CR^{5a}R^{5b}$, $CR^{5a}$, O, N, $NR^{5c}$, or S, wherein the number of heteroatoms forming the ring structure of ring A in $Z^1$, $Z^2$, $Z^3$, $Z^4$ and $Z^5$ is 0 or 1;

$Z^1$ and $Z^3$, $Z^1$ and $Z^4$, $Z^1$ and $Z^5$, $Z^2$ and $Z^4$, $Z^2$ and $Z^5$, $Z^3$ and $Z^5$, $R^4$ and $Z^2$, $R^4$ and $Z^3$, $R^4$ and $Z^4$ or $R^4$ and $Z^5$ may be taken together to form a substituted or unsubstituted C1-C4 cross-link optionally interrupted by one heteroatom selected from $NR^{5c}$, O and S;

$R^{5a}$ and $R^{5b}$ are each independently hydrogen, halogen, hydroxy, substituted or unsubstituted alkyl, or substituted or unsubstituted alkyloxy;

$R^{5a}$ and $R^{5b}$ on the same carbon atom may be taken together to form a substituted or unsubstituted non-aromatic carbocycle, or a substituted or unsubstituted non-aromatic heterocycle;

$R^{5c}$ is hydrogen, substituted or unsubstituted alkyl, substituted or unsubstituted alkylcarbonyl, substituted or unsubstituted alkyloxycarbonyl, substituted or unsubstituted carbamoyl, substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl;

$R^3$ and $R^4$ may be taken together with the adjacent atoms to form a substituted or unsubstituted non-aromatic heterocycle.

[3] The compound according to [1] or a pharmaceutically acceptable salt thereof, wherein ring A is any of the following rings:

[Chemical Formula 3]

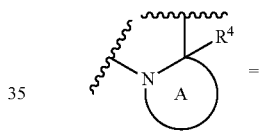

(a1)

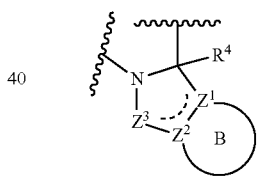

(b1)

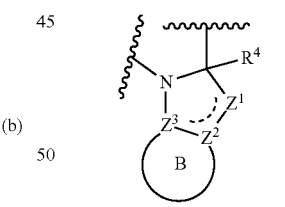

(c1)

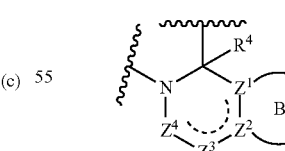

(d1)

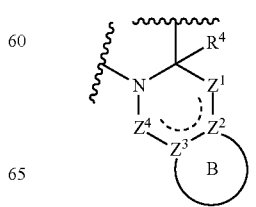

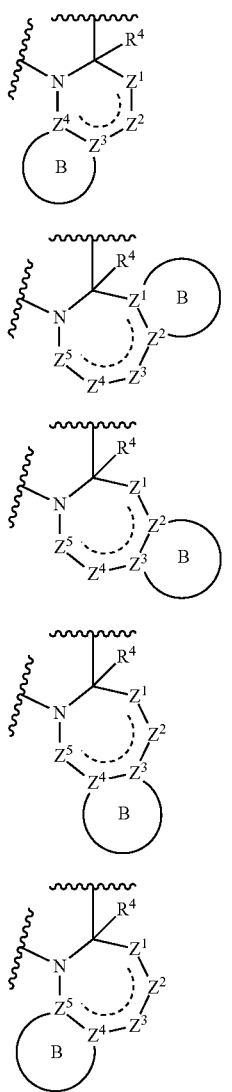

(e1)

(f1)

(g1)

(h1)

(i1)

wherein

R⁴ is hydrogen, or substituted or unsubstituted alkyl;

the broken line represents the presence or absence of a bond;

ring B is a substituted or unsubstituted carbocycle or a substituted or unsubstituted heterocycle;

$Z^1$, $Z^2$, $Z^3$, $Z^4$ and $Z^5$ are each independently $CR^{5a}R^{5b}$, $CR^a$, C, O, N, $NR^{5c}$, or S (provided that an atom constituting ring B is $CR^{5a}$, C or N);

$Z^1$ and $Z^3$, $Z^1$ and $Z^4$, $Z^1$ and $Z^5$, $Z^2$ and $Z^4$, $Z^2$ and $Z^5$, $Z^3$ and $Z^5$, $R^4$ and $Z^2$, $R^4$ and $Z^3$, $R^4$ and $Z^4$ or $R^4$ and $Z^5$ may be taken together to form a substituted or unsubstituted C2-C4 cross-link optionally interrupted by one heteroatom selected from $NR^{5c}$, O and S;

$R^{5a}$ and $R^{5b}$ are each independently hydrogen, halogen, substituted or unsubstituted alkyl, or substituted or unsubstituted alkyloxy;

$R^{5a}$ and $R^{5b}$ on the same carbon atom may be taken together to form a substituted or unsubstituted non-aromatic carbocycle, or a substituted or unsubstituted non-aromatic heterocycle;

$R^{5c}$ is hydrogen, substituted or unsubstituted alkyl, substituted or unsubstituted alkylcarbonyl, substituted or unsubstituted alkyloxycarbonyl, substituted or unsubstituted carbamoyl, substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl;

$R^3$ and $R^4$ may be taken together with the adjacent atoms to form a substituted or unsubstituted non-aromatic heterocycle.

[4] The compound according to any one of [1] to [3] or a pharmaceutically acceptable salt thereof, wherein the compound is represented by the following formula (II):

[Chemical Formula 4]

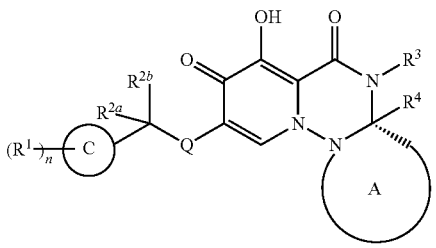

(II)

wherein ring A is any of the following ring;

[Chemical Formula 5]

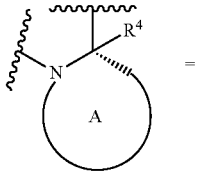

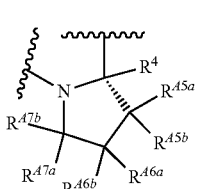

(a2)

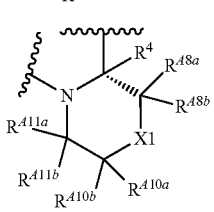

(b2)

X1 is $CR^{A9a}R^{A9b}$ or O;

$R^{A5a}$, $R^{A5b}$, $R^{A6a}$, $R^{A6b}$, $R^{A7a}$ and $R^{A7b}$ are each independently hydrogen, alkyl, alkyloxy or alkyloxyalkyl;

$R^{A5a}$ and $R^{A6a}$, or $R^{A6a}$ and $R^{A7a}$ may be taken together with the adjacent atoms to form an aromatic carbocycle optionally substituted with halogen, a 3- to 6-membered non-aromatic carbocycle optionally substituted with halogen, or a 4- to 6-membered non-aromatic heterocycle optionally substituted with halogen (provided that $R^{A5b}$ and $R^{A6b}$, or $R^{A6b}$ and $R^{A7b}$ are taken together to form a bond when forming an aromatic carbocycle);

$R^{A5b}$ and $R^{A6b}$ may be taken together to form a bond;

$R^{A8a}$, $R^{A8b}$, $R^{A9a}$, $R^{A9b}$, $R^{A10a}$, $R^{A10b}$, $R^{A11a}$ and $R^{A11b}$ are each independently hydrogen, alkyl, alkyloxy or alkyloxyalkyl;

$R^{A8a}$ and $R^{A10a}$ may be taken together to form a C1-C3 cross-link;

$R^{A10a}$ and $R^{A11a}$ may be taken together with the adjacent atoms to form a 5-membered non-aromatic carbocycle;

$R^{A9a}$ and $R^{A9b}$ may be taken together with the adjacent atoms to form a 4-membered non-aromatic carbocycle or a 5-membered non-aromatic heterocycle;

$R^{A8a}$ and $R^{A9a}$ may be taken together to form a bond;

ring C is a benzene ring or a pyridine ring;

Q is a 5-membered aromatic heterocycle;

each $R^1$ is independently halogen, alkyl, haloalkyl, alkyloxy, cyano, or haloalkyloxy;

$R^{2a}$ and $R^{2b}$ are each independently hydrogen, alkyl, or haloalkyl;

$R^3$ is alkyl or haloalkyl;

$R^4$ is hydrogen or alkyl; and n is an integer of 1 to 3.

[5] The compound according to any one of [1] to [3] or a pharmaceutically acceptable salt thereof, wherein $R^3$ is alkyl or haloalkyl.

[6] The compound according to any one of [1] to [4] or a pharmaceutically acceptable salt thereof, wherein $R^3$ is alkyl.

[7] The compound according to any one of [1] to [3], [5] or [6] or a pharmaceutically acceptable salt thereof, wherein $R^4$ is hydrogen or alkyl.

[8] The compound according to any one of [1] to [7] or a pharmaceutically acceptable salt thereof, wherein each $R^1$ is independently halogen, alkyl, or haloalkyl.

[9] The compound according to any one of [1] to [7] or a pharmaceutically acceptable salt thereof, wherein each $R^1$ is independently halogen.

[10] The compound according to any one of [1] to [3] or [5] to [9] or a pharmaceutically acceptable salt thereof, wherein $R^{2a}$ is hydrogen and $R^{2b}$ is hydrogen or alkyl, or $R^{2a}$ and $R^{2b}$ are taken together with the adjacent carbon atom to form a C3-C4 carbocycle.

[11] The compound according to any one of [1] to [9] or a pharmaceutically acceptable salt thereof, wherein $R^{2a}$ is hydrogen, and $R^{2b}$ is hydrogen or alkyl.

[12] The compound according to any one of [1] to [3] or [5] to [11] or a pharmaceutically acceptable salt thereof, wherein Q is a 5-membered aromatic heterocycle.

[13] The compound according to any one of [1] to [3] or [5] to [12] or a pharmaceutically acceptable salt thereof, wherein the carbon atom adjacent to $R^4$ has the following configuration:

[Chemical Formula 6]

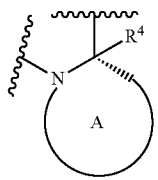

wherein ring A and $R^4$ are as defined in [1].

[14] The compound according to [1] or a pharmaceutically acceptable salt thereof, wherein the compound is selected from the group consisting of compounds I-2, I-6 and I-8.

[15] The compound according to [1] or a pharmaceutically acceptable salt thereof, wherein the compound is selected from the group consisting of compounds II-3, II-18, II-23, II-24, II-27, II-29, II-33, II-37, II-38, II-44, II-48, II-50, II-51, II-52, II-54, II-55, II-56, II-57, II-58, II-61, II-62, II-63, II-65, II-67 and II-68.

[16] A pharmaceutical composition comprising a compound according to any one of [1] to [15] or a pharmaceutically acceptable salt thereof.

[17] The pharmaceutical composition according to [16], wherein the pharmaceutical composition is an anti-HIV agent.

[18] An HIV integrase inhibitor comprising the compound according to any one of [1] to [15] or a pharmaceutically acceptable salt thereof.

[19] A method for treating and/or preventing HIV infection comprising administering the compound according to any one of [1] to [15], or a pharmaceutically acceptable salt thereof.

[20] The compound according to any one of [1] to [15], or a pharmaceutically acceptable salt thereof for use in treating and/or preventing HIV infection.

[1'] A compound represented by the following formula (I') or a pharmaceutically acceptable salt thereof:

[Chemical Formula 7]

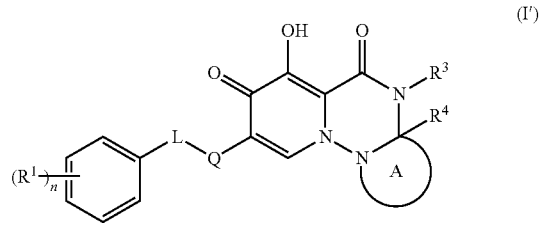

wherein ring A is a substituted or unsubstituted heterocycle;

Q is a heterocycle optionally substituted by halogen, alkyl, haloalkyl, alkyloxy, haloalkyloxy, or alkylamino;

each $R^1$ is independently halogen, alkyl, haloalkyl, alkyloxy, nitrile, or haloalkyloxy;

L is substituted or unsubstituted alkylene;

$R^3$ is substituted or unsubstituted alkyl, substituted or unsubstituted non-aromatic carbocyclyl, or substituted or unsubstituted non-aromatic heterocyclyl;

$R^4$ is hydrogen, or substituted or unsubstituted alkyl;

$R^3$ and $R^4$, or $R^3$ and a substituent on ring A may be taken together with the adjacent atoms to form a substituted or unsubstituted heterocycle; and n is an integer of 1 to 3.

[2'] The compound according to [1'] or a pharmaceutically acceptable salt thereof, wherein ring A is any of the following rings:

[Chemical Formula 8]

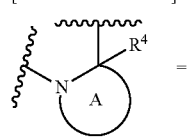 =

-continued (a)

(b)

(c)

wherein

R⁴ is hydrogen, or substituted or unsubstituted alkyl;
the broken line represents the presence or absence of a bond;
$Z^1$, $Z^2$, $Z^3$, $Z^4$ and $Z^5$ are each independently $CR^{5a}R^{5b}$, $CR^{5a}$, O, N, $NR^{5c}$, S, S(=O), S(=O)$_2$, or S(=O)=$NR^{5c}$, wherein the number of heteroatoms among $Z^1$, $Z^2$, $Z^3$, $Z^4$ and $Z^5$ is 0 or 1;
$Z^1$ and $Z^3$, $Z^1$ and $Z^4$, $Z^1$ and $Z^5$, $Z^2$ and $Z^4$, $Z^2$ and $Z^5$, $Z^3$ and $Z^5$, $R^4$ and $Z^2$, $R^4$ and $Z^3$, $R^4$ and $Z^4$ or $R^4$ and $Z^5$ may be taken together to form a substituted or unsubstituted C2-C4 cross-link;
$R^{5a}$ and $R^{5b}$ are each independently hydrogen, halogen, hydroxy, substituted or unsubstituted alkyl, substituted or unsubstituted alkyloxy, substituted or unsubstituted alkyloxycarbonyl, substituted or unsubstituted amino, substituted or unsubstituted carbamoyl, substituted or unsubstituted ureido, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, or substituted or unsubstituted non-aromatic heterocyclyloxy;
$R^{5a}$ and $R^{5b}$ on the same carbon atom may be taken together to form oxo, thioxo or a substituted or unsubstituted spiro ring;
$R^{5c}$ is hydrogen, substituted or unsubstituted alkyl, substituted or unsubstituted alkylcarbonyl, substituted or unsubstituted alkyloxycarbonyl, substituted or unsubstituted carbamoyl, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocyclyloxycarbonyl, substituted or unsubstituted non-aromatic carbocyclyloxycarbonyl, substituted or unsubstituted aromatic heterocyclyloxycarbonyl, or substituted or unsubstituted non-aromatic heterocyclyloxycarbonyl; and
$R^3$ and $R^4$, or $R^3$ and a substituent on $Z^1$ may be taken together with the adjacent atoms to form a substituted or unsubstituted heterocycle.

[3'] The compound according to [1'] or a pharmaceutically acceptable salt thereof, wherein ring A is any of the following rings:

[Chemical Formula 9]

(a1)

(b1)

(c1)

(d1)

(e1)

(f1)

(g1)

-continued

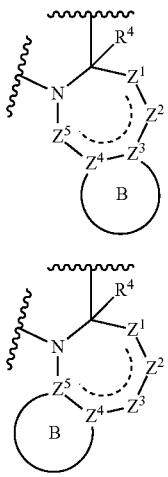

(h1)

(i1)

wherein
R⁴ is hydrogen, or substituted or unsubstituted alkyl;
the broken line represents the presence or absence of a bond;
ring B is a substituted or unsubstituted carbocycle or a substituted or unsubstituted heterocycle;
$Z^1$, $Z^2$, $Z^3$, $Z^4$ and $Z^5$ are each independently $CR^{5a}R^{5b}$, $CR^{5a}$, C, O, N, $NR^{5c}$, S, S(=O), S(=O)$_2$, or S(=O)=$NR^{5d}$ (provided that an atom constituting ring B is $CR^{5a}$, C or N);
$Z^1$ and $Z^3$, $Z^1$ and $Z^4$, $Z^1$ and $Z^5$, $Z^2$ and $Z^4$, $Z^2$ and $Z^5$, $Z^3$ and $Z^5$, $R^4$ and $Z^2$, $R^4$ and $Z^3$, $R^4$ and $Z^4$ or $R^4$ and $Z^5$ may be taken together to form a substituted or unsubstituted C2-C4 cross-link;
$R^{5a}$ and $R^{5b}$ are each independently hydrogen, halogen, hydroxy, substituted or unsubstituted alkyl, substituted or unsubstituted alkyloxy, substituted or unsubstituted alkyloxycarbonyl, substituted or unsubstituted amino, substituted or unsubstituted carbamoyl, substituted or unsubstituted ureido, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, or substituted or unsubstituted non-aromatic heterocyclyloxy;
$R^{5a}$ and $R^{5b}$ on the same carbon atom may be taken together to form oxo, thioxo or a substituted or unsubstituted spiro ring;
$R^{5c}$ is hydrogen, substituted or unsubstituted alkyl, substituted or unsubstituted alkylcarbonyl, substituted or unsubstituted alkyloxycarbonyl, substituted or unsubstituted carbamoyl, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocyclyloxycarbonyl, substituted or unsubstituted non-aromatic carbocyclyloxycarbonyl, substituted or unsubstituted aromatic heterocyclyloxycarbonyl, or substituted or unsubstituted non-aromatic heterocyclyloxycarbonyl;
$R^{5d}$ is hydrogen, substituted or unsubstituted alkyl, substituted or unsubstituted alkylcarbonyl, substituted or unsubstituted alkyloxycarbonyl, substituted or unsubstituted carbamoyl, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocyclyloxycarbonyl, substituted or unsubstituted non-aromatic carbocyclyloxycarbonyl, substituted or unsubstituted aromatic heterocyclyloxycarbonyl, or substituted or unsubstituted non-aromatic heterocyclyloxycarbonyl; and
$R^3$ and $R^4$, or $R^3$ and a substituent on $Z^1$ may be taken together with the adjacent atoms to form a substituted or unsubstituted heterocycle.

[4′] The compound according to any one of [1′] to [4′] or a pharmaceutically acceptable salt thereof, wherein the compound is represented by the following formula (I-2):

[Chemical Formula 10]

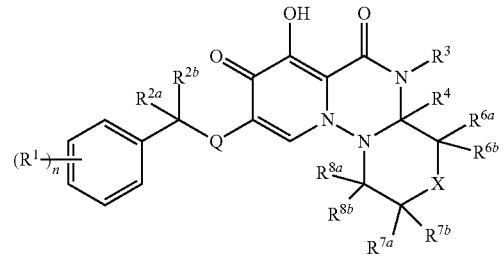

(I-2)

wherein
$R^{2a}$ and $R^{2b}$ are each independently hydrogen, alkyl, or haloalkyl;
$R^{2a}$ and $R^{2b}$ may be taken together with the adjacent carbon atom to form a carbocycle or a heterocycle;
$R^3$ is substituted or unsubstituted alkyl, substituted or unsubstituted non-aromatic carbocyclyl, or substituted or unsubstituted non-aromatic heterocyclyl;
$R^4$ is hydrogen, or substituted or unsubstituted alkyl;
X is $CR^{9a}R^{9b}$, $NR^{10}$, S, S(=O), S(=O)$_2$, or S(=O)=$NR^{11}$;
$R^{6a}$, $R^{6b}$, $R^{7a}$, $R^{7b}$, $R^{8a}$, $R^{8b}$, $R^{9a}$, and $R^{9b}$ are each independently hydrogen, halogen, hydroxy, substituted or unsubstituted alkyl, substituted or unsubstituted alkyloxy, or substituted or unsubstituted amino;
$R^{6b}$ and $R^{9b}$, $R^{9b}$ and $R^{7b}$, or $R^{7b}$ and $R^{8b}$ may be taken together with the adjacent atoms to form a substituted or unsubstituted carbocycle or a substituted or unsubstituted heterocycle;
$R^4$ and $R^{7b}$, or $R^{6b}$ and $R^{8b}$ may be taken together to form a substituted or unsubstituted C2-C4 cross-link;
$R^{6b}$ and $R^{10}$, or $R^{10}$ and $R^{7b}$ may be taken together with the adjacent atoms to form a substituted or unsubstituted heterocycle;
$R^3$ and $R^4$, or $R^3$ and $R^{6b}$ may be taken together with the adjacent atoms to form a substituted or unsubstituted heterocycle;
$R^{10}$ is substituted or unsubstituted alkyl, substituted or unsubstituted alkyl, substituted or unsubstituted alkylcarbonyl, substituted or unsubstituted alkyloxycarbonyl, substituted or unsubstituted carbamoyl, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted non-aromatic heterocyclylalkylcarbonyl, substituted or unsubstituted aromatic carbocycly-loxycarbonyl, substituted or unsubstituted non-aromatic carbocyclyloxycarbonyl, substituted or unsubstituted aromatic heterocyclyloxycarbonyl, or substituted or unsubstituted non-aromatic heterocyclyloxycarbonyl;

$R^{11}$ is substituted or unsubstituted alkyl, substituted or unsubstituted alkylcarbonyl, substituted or unsubstituted alkyloxycarbonyl, substituted or unsubstituted carbamoyl, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocyclyloxycarbonyl, substituted or unsubstituted non-aromatic carbocyclyloxycarbonyl, substituted or unsubstituted aromatic heterocyclyloxycarbonyl, or substituted or unsubstituted non-aromatic heterocyclyloxycarbonyl; and Q, $R^1$, and n are as defined in [1'].

[5'] The compound according to any one of [1'] to [4'] or a pharmaceutically acceptable salt thereof, wherein $R^3$ is alkyl or haloalkyl.

[6'] The compound according to any one of [1'] to [5'] or a pharmaceutically acceptable salt thereof, wherein $R^4$ is hydrogen.

[7'] The compound according to any one of [1'] to [6'] or a pharmaceutically acceptable salt thereof, wherein n is an integer of 2 or 3, and each $R^1$ is independently halogen, alkyl, or haloalkyl.

[8'] The compound according to any one of [4'] to [7'] or a pharmaceutically acceptable salt thereof, wherein $R^{2a}$ is hydrogen, and $R^{2b}$ is hydrogen or alkyl, or $R^{2a}$ and $R^{2b}$ are taken together with the adjacent carbon atom to form a C3-C4 carbocycle.

[9'] The compound according to any one of [1'] to [8'] or a pharmaceutically acceptable salt thereof, wherein Q is a 5- or 6-membered aromatic heterocycle optionally substituted by halogen, alkyl, haloalkyl, alkyloxy, haloalkyloxy, or alkylamino.

[10'] The compound according to any one of [1'] to [9'] or a pharmaceutically acceptable salt thereof, wherein the carbon atom adjacent to $R^4$ has the following configuration:

[Chemical Formula 11]

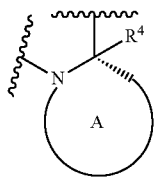

wherein ring A and $R^4$ are as defined in [1'].

[11'] The compound according to [1] or a pharmaceutically acceptable salt thereof, wherein the compound is selected from the group consisting of compounds I-2, I-4, I-5, I-6 and I-8.

[12'] A pharmaceutical composition comprising a compound according to any one of [1'] to [11'] or a pharmaceutically acceptable salt thereof.

[13'] The pharmaceutical composition according to [12'], wherein the pharmaceutical composition is an anti-HIV agent.

[14'] The pharmaceutical composition according to [12'], wherein the pharmaceutical composition is an HIV integrase inhibitor.

The present invention further provides a method for preventing or treating HIV, comprising administering an effective amount of the compound to a human.

The present invention further provides the compound for use as an anti-HIV drug.

Effect of the Invention

The compound of the present invention has integrase inhibitory activity and/or cell growth inhibitory activity against a virus, particularly, HIV or a resistant virus thereof. Accordingly, the compound of the present invention is useful in the prevention or treatment of various diseases, virus infections (e.g., AIDS), and the like involving integrase. More preferably, the compound of the present invention is useful as a long-acting integrase inhibitor. Furthermore, the compound of the present invention is also excellent in resistance profile that the compound cannot easily cause a new HIV-resistant virus, and the like. Further preferably, the compound of the present invention also has a prophylactic or therapeutic effect on an HIV drug-resistant virus. Still further preferably, the compound of the present invention has small clearance, a long in vivo half-life, and excellent solubility, metabolic stability, or bioavailability, etc. and is also useful as a medicament with less concerns about cytotoxicity or a side effect (e.g., mutagenicity, the QT interval prolongation of the electrocardiogram, and arrhythmia).

MODE FOR CARRYING OUT THE INVENTION

The meaning of each term used in the present description is explained below. Each term is used in the same sense when used alone, or when used in combination of other term, unless otherwise specified.

The term "consisting of" means having only components.

The term "comprising" means not restricting with components and not excluding undescribed factors.

The term "halogen" includes a fluorine atom, a chlorine atom, a bromine atom, and an iodine atom. Particularly, a fluorine atom and a chlorine atom are preferred.

The term "alkyl" includes a C1 to C15, preferably C1 to C10, more preferably C1 to C6 and further preferably C1 to C4 linear or branched hydrocarbon group. Examples include methyl, ethyl, n-propyl, isopropyl, n-butyl, isobutyl, sec-butyl, tert-butyl, n-pentyl, isopentyl, neopentyl, n-hexyl, isohexyl, n-heptyl, isoheptyl, n-octyl, isooctyl, n-nonyl, n-decyl and the like.

A preferred form of "alkyl" is methyl, ethyl, n-propyl, isopropyl, n-butyl, isobutyl, sec-butyl, tert-butyl or n-pentyl. A more preferred form is methyl, ethyl, n-propyl, isopropyl or tert-butyl.

The term "alkenyl" includes a C2 to C15, preferably a C2 to C10, more preferably a C2 to C6 and further preferably a C2 to C4 linear or branched hydrocarbon group having one or more double bond(s) at any position(s). Examples include vinyl, allyl, propenyl, isopropenyl, butenyl, isobutenyl, prenyl, butadienyl, pentenyl, isopentenyl, pentadienyl, hexenyl, isohexenyl, hexadienyl, heptenyl, octenyl, nonenyl, decenyl, undecenyl, dodecenyl, tridecenyl, tetradecenyl, pentadecenyl and the like.

A preferred form of "alkenyl" is vinyl, allyl, propenyl, isopropenyl or butenyl.

The term "alkylene" includes a C1 to C15, preferably a C1 to C10, more preferably a C1 to C6 and further preferably a C1 to C4 liner or branched bivalent hydrocarbon group. Examples include methylene, ethylene, trimethylene, propylene, tetramethylene, pentamethylene, hexamethylene and the like.

In addition, "alkylene" also includes a cross-linked group as follows:

[Chemical Formula 12]

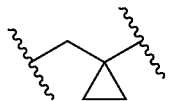

The term "Aromatic carbocyclyl" means a cyclic aromatic hydrocarbon group which is monocyclic or bicyclic or higher. For example, it includes phenyl, naphthyl, anthryl, phenanthryl and the like.

A preferred form of "aromatic carbocyclyl" is phenyl.

The term "Non-aromatic carbocyclyl" means a cyclic saturated hydrocarbon group or a cyclic non-aromatic unsaturated hydrocarbon group, which is monocyclic or bicyclic or higher. "Non-aromatic carbocyclyl", which is bicyclic or higher, includes a condensed ring group wherein a non-aromatic carbocyclyl, which is monocyclic or bicyclic or higher, is condensed with a ring of the above "aromatic carbocyclyl".

In addition, the "non-aromatic carbocyclyl" also includes a cross-linked group or a group forming a spiro ring as follows:

[Chemical Formula 13]

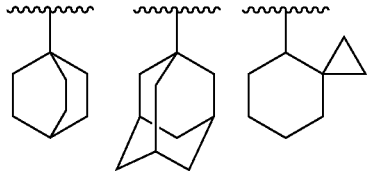

A non-aromatic carbocyclyl which is monocyclic has preferably 3 to 16 carbon atoms, more preferably 3 to 12 carbon atoms and further preferably 4 to 8 carbon atoms. Examples thereof include cyclopropyl, cyclobutyl, cyclopentyl, cyclohexyl, cycloheptyl, cyclooctyl, cyclononyl, cyclodecyl, cyclopropenyl, cyclobutenyl, cyclopentenyl, cyclohexenyl, cycloheptenyl, and cyclohexadienyl.

The bicyclic or higher non-aromatic carbocyclyl preferably has 8 to 20 carbon atoms, more preferably 8 to 16 carbon atoms. Examples thereof include indanyl, indenyl, acenaphthyl, tetrahydronaphthyl, and fluorenyl.

The term "aromatic heterocyclyl" means a monocyclic or bicyclic or higher aromatic cyclic group having one or more same or different heteroatoms arbitrarily selected from O, S and N in the ring.

The bicyclic or higher aromatic heterocyclyl also includes a monocyclic or bicyclic or higher aromatic heterocyclyl condensed with the ring of the "aromatic carbocyclyl" described above. The bond may be present on any of the rings.

The monocyclic aromatic heterocyclyl preferably has 5 to 8 members, more preferably 5 or 6 members. Examples of the 5-membered aromatic heterocyclyl include pyrrolyl, imidazolyl, pyrazolyl, triazolyl, tetrazolyl, furyl, thienyl, isoxazolyl, oxazolyl, oxadiazolyl, isothiazolyl, thiazolyl, and thiadiazolyl. Examples of the 6-membered aromatic heterocyclyl include pyridyl, pyridazinyl, pyrimidinyl, pyrazinyl, and triazinyl.

The bicyclic aromatic heterocyclyl preferably has 8 to 10 members, more preferably 9 or 10 members. Examples thereof include indolyl, isoindolyl, indazolyl, indolizinyl, quinolinyl, isoquinolinyl, cinnolinyl, phthalazinyl, quinazolinyl, naphthyridinyl, quinoxalinyl, purinyl, pteridinyl, benzimidazolyl, benzisoxazolyl, benzoxazolyl, benzoxadiazolyl, benzisothiazolyl, benzothiazolyl, benzothiadiazolyl, benzofuryl, isobenzofuryl, benzothienyl, benzotriazolyl, imidazopyridyl, triazolopyridyl, imidazothiazolyl, pyrazinopyridazinyl, oxazolopyridyl, and thiazolopyridyl.

The tricyclic or higher aromatic heterocyclyl preferably has 13 to 15 members. Examples thereof include carbazolyl, acridinyl, xanthenyl, phenothiazinyl, phenoxathiinyl, phenoxazinyl, and dibenzofuryl.

The term "non-aromatic heterocyclyl" means a monocyclic or bicyclic or higher non-aromatic cyclic group having one or more same or different heteroatoms arbitrarily selected from O, S and N in the ring. The bicyclic or higher non-aromatic heterocyclyl also includes a monocyclic or bicyclic or higher non-aromatic heterocyclyl condensed with the ring of the "aromatic carbocyclyl", the "non-aromatic carbocyclyl", and/or the "aromatic heterocyclyl" described above, and a monocyclic or bicyclic or higher non-aromatic carbocyclyl condensed with the ring of the "aromatic heterocyclyl" described above. The bond may be present on any of the rings.

The "non-aromatic heterocyclyl" further includes a cross-linked group, or a group forming a spiro ring, as shown below.

[Chemical Formula 14]

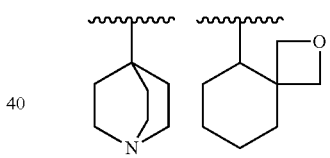

The monocyclic non-aromatic heterocyclyl preferably has 3 to 8 members, more preferably 5 or 6 members.

Examples of the 3-membered non-aromatic heterocyclyl include thiiranyl, oxiranyl, and aziridinyl. Examples of the 4-membered non-aromatic heterocyclyl include oxetanyl and azetidinyl. Examples of the 5-membered non-aromatic heterocyclyl include oxathiolanyl, thiazolidinyl, pyrrolidinyl, pyrrolinyl, imidazolidinyl, imidazolinyl, pyrazolidinyl, pyrazolinyl, tetrahydrofuryl, dihydrothiazolyl, tetrahydroisothiazolyl, dioxolanyl, dioxolyl, and thiolanyl. Examples of the 6-membered non-aromatic heterocyclyl include dioxanyl, thianyl, piperidinyl, piperazinyl, morpholinyl, morpholino, thiomorpholinyl, thiomorpholino, dihydropyridyl, tetrahydropyridyl, tetrahydropyranyl, dihydrooxazinyl, tetrahydropyridazinyl, hexahydropyrimidinyl, dioxazinyl, thiinyl, and thiazinyl. Examples of the 7-membered non-aromatic heterocyclyl include hexahydroazepinyl, tetrahydrodiazepinyl, and oxepanyl.

The bicyclic or higher non-aromatic heterocyclyl preferably has 8 to 20 members, more preferably 8 to 10 members. Examples thereof include indolinyl, isoindolinyl, chromanyl, and isochromanyl.

The terms "aromatic carbocycle", "non-aromatic carbocycle", "aromatic heterocycle" and "non-aromatic heterocycle" mean rings derived from the "aromatic carbocyclyl", the "non-aromatic carbocyclyl", the "aromatic heterocyclyl" and the "non-aromatic heterocyclyl", respectively, described above.

The term "carbocycle" means the "aromatic carbocycle" or the "non-aromatic carbocycle" described above.

The term "heterocycle" means the "aromatic heterocycle" or the "non-aromatic heterocycle" described above.

The term "spiro ring" means the "non-aromatic carbocycle" or the "non-aromatic heterocycle" described above.

In the present description, the phrase "optionally substituted by substituent group α" means "optionally substituted by one or more groups selected from substituent group α". The same holds true for the phrases "optionally substituted by substituent group β", "optionally substituted by substituent group γ", and "optionally substituted by substituent group γ'".

Examples of the substituents for the "substituted alkyl", the "substituted alkyloxy", the "substituted alkylcarbonyl", the "substituted alkyloxycarbonyl", the "substituted C1-C4 cross-link", the "substituted C2-C4 cross-link" and the "substituted alkylene" include substituent group A given below. A carbon atom at an arbitrary position may be bonded to one or more groups selected from the following substituent group A:

Substituent group A: halogen, hydroxy, carboxy, formyl, formyloxy, sulfanyl, sulfino, sulfo, thioformyl, thiocarboxy, dithiocarboxy, thiocarbamoyl, cyano, nitro, nitroso, azide, hydrazino, ureido, amidino, guanidino, alkyloxy optionally substituted by substituent group α, alkenyloxy optionally substituted by substituent group α, alkylcarbonyloxy optionally substituted by substituent group α, alkenylcarbonyloxy optionally substituted by substituent group α, alkylcarbonyl optionally substituted by substituent group α, alkenylcarbonyl optionally substituted by substituent group α, alkyloxycarbonyl optionally substituted by substituent group α, alkenyloxycarbonyl optionally substituted by substituent group α, alkylsulfanyl optionally substituted by substituent group α, alkenylsulfanyl optionally substituted by substituent group α, alkylsulfinyl optionally substituted by substituent group α, alkenylsulfinyl optionally substituted by substituent group α, alkylsulfonyl optionally substituted by substituent group α, alkenylsulfonyl optionally substituted by substituent group α, amino optionally substituted by substituent group β, imino optionally substituted by substituent group β, carbamoyl optionally substituted by substituent group β, sulfamoyl optionally substituted by substituent group β, ureido optionally substituted by substituent group β, an aromatic carbocyclyl optionally substituted by substituent group γ, a non-aromatic carbocyclyl optionally substituted by substituent group γ', an aromatic heterocyclyl optionally substituted by substituent group γ, a non-aromatic heterocyclyl optionally substituted by substituent group γ', aromatic carbocyclyloxy optionally substituted by substituent group γ, non-aromatic carbocyclyloxy optionally substituted by substituent group γ', aromatic heterocyclyloxy optionally substituted by substituent group γ, non-aromatic heterocyclyloxy optionally substituted by substituent group γ', aromatic carbocyclylcarbonyloxy optionally substituted by substituent group γ, non-aromatic carbocyclylcarbonyloxy optionally substituted by substituent group γ', aromatic heterocyclylcarbonyloxy optionally substituted by substituent group γ, non-aromatic heterocyclylcarbonyloxy optionally substituted by substituent group γ', aromatic carbocyclylcarbonyl optionally substituted by substituent group γ, non-aromatic carbocyclylcarbonyl optionally substituted by substituent group γ', aromatic heterocyclylcarbonyl optionally substituted by substituent group γ, non-aromatic heterocyclylcarbonyl optionally substituted by substituent group γ', aromatic carbocyclyloxycarbonyl optionally substituted by substituent group γ, non-aromatic carbocyclyloxycarbonyl optionally substituted by substituent group γ', aromatic heterocyclyloxycarbonyl optionally substituted by substituent group γ, non-aromatic heterocyclyloxycarbonyl optionally substituted by substituent group γ', aromatic carbocyclylalkyloxy optionally substituted by substituent group γ, non-aromatic carbocyclylalkyloxy optionally substituted by substituent group γ', aromatic heterocyclylalkyloxy optionally substituted by substituent group γ, non-aromatic heterocyclylalkyloxy optionally substituted by substituent group γ', aromatic carbocyclylalkyloxycarbonyl optionally substituted by substituent group γ, non-aromatic carbocyclylalkyloxycarbonyl optionally substituted by substituent group γ', aromatic heterocyclylalkyloxycarbonyl optionally substituted by substituent group γ, non-aromatic heterocyclylalkyloxycarbonyl optionally substituted by substituent group γ', aromatic carbocyclylsulfanyl optionally substituted by substituent group γ, non-aromatic carbocyclylsulfanyl optionally substituted by substituent group γ', aromatic heterocyclylsulfanyl optionally substituted by substituent group γ, non-aromatic heterocyclylsulfanyl optionally substituted by substituent group γ', aromatic carbocyclylsulfinyl optionally substituted by substituent group γ, non-aromatic carbocyclylsulfinyl optionally substituted by substituent group γ', aromatic heterocyclylsulfinyl optionally substituted by substituent group γ, non-aromatic heterocyclylsulfinyl optionally substituted by substituent group γ', aromatic carbocyclylsulfonyl optionally substituted by substituent group γ, non-aromatic carbocyclylsulfonyl optionally substituted by substituent group γ', aromatic heterocyclylsulfonyl optionally substituted by substituent group γ, and non-aromatic heterocyclylsulfonyl optionally substituted by substituent group γ'.

Substituent group α: halogen, hydroxy, carboxy, alkyloxy, haloalkyloxy, alkenyloxy, sulfanyl, cyano, nitro, and guanidino.

Substituent group β: alkyl optionally substituted by substituent group α, alkenyl optionally substituted by substituent group α, alkylcarbonyl optionally substituted by substituent group α, alkenylcarbonyl optionally substituted by substituent group α, alkylsulfanyl optionally substituted by substituent group α, alkenylsulfanyl optionally substituted by substituent group α, alkylsulfinyl optionally substituted by substituent group α, alkenylsulfinyl optionally substituted by substituent group α, alkylsulfonyl optionally substituted by substituent group α, alkenylsulfonyl optionally substituted by substituent group α, an aromatic carbocyclyl optionally substituted by substituent group γ, a non-aromatic carbocyclyl optionally substituted by substituent group γ', an aromatic heterocyclyl optionally substituted by substituent group γ, a non-aromatic heterocyclyl optionally substituted by substituent group γ', aromatic carbocyclylalkyl optionally substituted by substituent group γ, non-aromatic carbocyclylalkyl optionally substituted by substituent group γ', aromatic heterocyclylalkyl optionally substituted by substituent group γ, non-aromatic heterocyclylalkyl optionally substituted by substituent group γ', aromatic carbocyclylcarbonyl optionally substituted by substituent group γ, non-aromatic carbocyclylcarbonyl optionally substituted by substituent group γ', aromatic heterocyclylcarbonyl optionally substituted by substituent group γ, non-aromatic heterocyclylcarbonyl optionally substituted by substituent group γ', aromatic carbocyclyloxycarbonyl optionally substituted by substituent group γ, non-aromatic carbocyclyloxycarbonyl optionally substituted by substituent group γ', aromatic heterocyclyloxycarbonyl optionally substituted by substituent group γ, aromatic carbocyclylsulfanyl optionally substituted by substituent group γ, non-aromatic carbocyclylsulfanyl optionally substituted by substituent group γ', aromatic heterocyclylsulfanyl optionally substituted by substituent group γ, non-aromatic heterocyclylsulfanyl optionally substituted by substituent group γ', aromatic carbocyclylsulfinyl optionally substituted by substituent group γ, non-aromatic carbocyclylsulfinyl optionally substituted by substituent group γ', aromatic heterocyclylsulfinyl optionally substituted by substituent group γ, non-aromatic heterocyclylsulfinyl optionally substituted by substituent group γ', aromatic carbocyclylsulfonyl optionally substituted by substituent group γ, non-aromatic carbocyclylsulfonyl optionally substituted by substituent group γ', aromatic heterocyclylsulfonyl optionally substituted by substituent group γ, and non-aromatic heterocyclylsulfonyl optionally substituted by substituent group γ'.

Substituent group γ: substituent group α, alkyl, haloalkyl, hydroxyalkyl, alkenyl, alkylcarbonyl, haloalkylcarbonyl, and alkenylcarbonyl.

Substituent group γ': substituent group γ and oxo.

Examples of the substituents on the rings of the "aromatic carbocycle" and the "aromatic heterocycle" of the "substituted carbocycle", the "substituted heterocycle", the "substituted aromatic carbocyclyl", the "substituted aromatic heterocyclyl", the "substituted aromatic carbocyclyloxy", the "substituted aromatic heterocyclyloxy", the "substituted aromatic carbocyclylcarbonyl", the "substituted aromatic heterocyclylcarbonyl", the "substituted aromatic carbocyclyloxycarbonyl" and the "substituted aromatic heterocyclyloxycarbonyl" include substituent group B given below. An atom at an arbitrary position on the ring may be bonded to one or more groups selected from the following substituent group B:

Substituent group B: halogen, hydroxy, carboxy, formyl, formyloxy, sulfanyl, sulfino, sulfo, thioformyl, thiocarboxy, dithiocarboxy, thiocarbamoyl, cyano, nitro, nitroso, azide, hydrazino, ureido, amidino, and guanidino, alkyl optionally substituted by substituent group α, alkenyl optionally substituted by substituent group α, alkyloxy optionally substituted by substituent group α, alkenyloxy optionally substituted by substituent group α, alkylcarbonyloxy optionally substituted by substituent group α, alkenylcarbonyloxy optionally substituted by substituent group α, alkylcarbonyl optionally substituted by substituent group α, alkenylcarbonyl optionally substituted by substituent group α, alkyloxycarbonyl optionally substituted by substituent group α, alkenyloxycarbonyl optionally substituted by substituent group α, alkylsulfanyl optionally substituted by substituent group α, alkenylsulfanyl optionally substituted by substituent group α, alkylsulfinyl optionally substituted by substituent group α, alkenylsulfinyl optionally substituted by substituent group α, alkylsulfonyl optionally substituted by substituent group α, alkenylsulfonyl optionally substituted by substituent group α, amino optionally substituted by substituent group β, imino optionally substituted by substituent group β, carbamoyl optionally substituted by substituent group β, sulfamoyl optionally substituted by substituent group β, ureido optionally substituted by substituent group, an aromatic carbocyclyl optionally substituted by substituent group γ, a non-aromatic carbocyclyl optionally substituted by substituent group γ', an aromatic heterocyclyl optionally substituted by substituent group γ, a non-aromatic heterocyclyl optionally substituted by substituent group γ', aromatic carbocyclyloxy optionally substituted by substituent group γ, non-aromatic carbocyclyloxy optionally substituted by substituent group γ', aromatic heterocyclyloxy optionally substituted by substituent group γ, non-aromatic heterocyclyloxy optionally substituted by substituent group γ', aromatic carbocyclylcarbonyloxy optionally substituted by substituent group γ, non-aromatic carbocyclylcarbonyloxy optionally substituted by substituent group γ', aromatic heterocyclylcarbonyloxy optionally substituted by substituent group γ, non-aromatic heterocyclylcarbonyloxy optionally substituted by substituent group γ', aromatic carbocyclylcarbonyl optionally substituted by substituent group γ, non-aromatic carbocyclylcarbonyl optionally substituted by substituent group γ', aromatic heterocyclylcarbonyl optionally substituted by substituent group γ, non-aromatic heterocyclylcarbonyl optionally substituted by substituent group γ', aromatic carbocyclyloxycarbonyl optionally substituted by substituent group γ, non-aromatic carbocyclyloxycarbonyl optionally substituted by substituent group γ', aromatic heterocyclyloxycarbonyl optionally substituted by substituent group γ, non-aromatic heterocyclyloxycarbonyl optionally substituted by substituent group γ', aromatic carbocyclylalkyl optionally substituted by substituent group γ, non-aromatic carbocyclylalkyl optionally substituted by substituent group γ', aromatic heterocyclylalkyl optionally substituted by substituent group γ, non-aromatic heterocyclylalkyl optionally substituted by substituent group γ', aromatic carbocyclylalkyloxy optionally substituted by substituent group γ, non-aromatic carbocyclylalkyloxy optionally substituted by substituent group γ', aromatic heterocyclylalkyloxy optionally substituted by substituent group γ, non-aromatic heterocyclylalkyloxy optionally substituted by substituent group γ', aromatic carbocyclylalkyloxycarbonyl optionally substituted by substituent group γ, non-aromatic carbocyclylalkyloxycarbonyl optionally substituted by substituent group γ', aromatic heterocyclylalkyloxycarbonyl optionally substituted by substituent group γ, non-aromatic heterocyclylalkyloxycarbonyl optionally substituted by substituent group γ', aromatic carbocyclylalkyloxyalkyl optionally substituted by substituent group γ, non-aromatic carbocyclylalkyloxyalkyl optionally substituted by substituent group γ', aromatic heterocyclylalkyloxyalkyl optionally substituted by substituent group γ, non-aromatic heterocyclylalkyloxyalkyl optionally substituted by substituent group γ', aromatic carbocyclylsulfanyl optionally substituted by substituent group γ, non-aromatic carbocyclylsulfanyl optionally substituted by substituent group γ', aromatic heterocyclylsulfanyl optionally substituted by substituent group γ, non-aromatic heterocyclylsulfanyl optionally substituted by substituent group γ', aromatic carbocyclylsulfinyl optionally substituted by substituent group γ, non-aromatic carbocyclylsulfinyl optionally substituted by substituent group γ', aromatic heterocyclylsulfinyl optionally substituted by substituent group γ, non-aromatic heterocyclylsulfinyl optionally substituted by substituent group γ', aromatic carbocyclylsulfonyl optionally substituted by substituent group γ, non-aromatic carbocyclylsulfonyl optionally substituted by substituent group γ', aromatic heterocyclylsulfonyl optionally substituted by substituent group γ, and non-aromatic heterocyclylsulfonyl optionally substituted by substituent group γ'.

Examples of the substituents on the rings of the "non-aromatic carbocycle" and the "non-aromatic heterocycle" of the "substituted carbocycle", the "substituted heterocycle", the "substituted non-aromatic carbocyclyl", the "substituted non-aromatic heterocyclyl", the "substituted non-aromatic carbocyclyloxy", the "substituted non-aromatic heterocyclyloxy", the "substituted non-aromatic carbocyclylcarbonyl", the "substituted non-aromatic heterocyclylcarbonyl", the "substituted non-aromatic carbocycloxycarbonyl" and the "substituted non-aromatic heterocyclyloxycarbonyl" include substituent group C given below. An atom at an arbitrary position on the ring may be bonded to one or more groups selected from the following substituent group C.

Substituent group C: substituent group B and oxo.

Examples of the substituents for the "substituted amino", the "substituted carbamoyl", and the "substituted ureido" include substituent group D given below. The moiety is optionally substituted by 1 or 2 groups selected from substituent group D.

Substituent group D: alkyl optionally substituted by substituent group α, alkenyl optionally substituted by substituent group α, alkylcarbonyl optionally substituted by substituent group α, alkenylcarbonyl optionally substituted by substituent group α, alkylsulfanyl optionally substituted by substituent group α, alkenylsulfanyl optionally substituted by substituent group α, alkylsulfinyl optionally substituted by substituent group α, alkenylsulfinyl optionally substituted by substituent group α, alkylsulfonyl optionally substituted by substituent group α, alkenylsulfonyl optionally substituted by substituent group α, an aromatic carbocyclyl optionally substituted by substituent group γ, a non-aromatic carbocyclyl optionally substituted by substituent group γ', an aromatic heterocyclyl optionally substituted by substituent group γ, a non-aromatic heterocyclyl optionally substituted by substituent group γ', aromatic carbocyclylalkyl optionally substituted by substituent group γ, non-aromatic carbocyclylalkyl optionally substituted by substituent group γ', aromatic heterocyclylalkyl optionally substituted by substituent group γ, non-aromatic heterocyclylalkyl optionally substituted by substituent group γ', aromatic carbocyclylcarbonyl optionally substituted by substituent group γ, non-aromatic carbocyclylcarbonyl optionally substituted by substituent group γ', aromatic heterocyclylcarbonyl optionally substituted by substituent group γ, non-aromatic heterocyclylcarbonyl optionally substituted by substituent group γ', aromatic carbocycloxycarbonyl optionally substituted by substituent group γ, non-aromatic carbocycloxycarbonyl optionally substituted by substituent group γ', aromatic heterocyclyloxycarbonyl optionally substituted by substituent group γ, non-aromatic heterocyclyloxycarbonyl optionally substituted by substituent group γ', aromatic carbocyclylsulfanyl optionally substituted by substituent group γ, non-aromatic carbocyclylsulfanyl optionally substituted by substituent group γ', aromatic heterocyclylsulfanyl optionally substituted by substituent group γ, non-aromatic heterocyclylsulfanyl optionally substituted by substituent group γ', aromatic carbocyclylsulfinyl optionally substituted by substituent group γ, non-aromatic carbocyclylsulfinyl optionally substituted by substituent group γ', aromatic heterocyclylsulfinyl optionally substituted by substituent group γ, non-aromatic heterocyclylsulfinyl optionally substituted by substituent group γ', aromatic carbocyclylsulfonyl optionally substituted by substituent group γ, non-aromatic carbocyclylsulfonyl optionally substituted by substituent group γ', aromatic heterocyclylsulfonyl optionally substituted by substituent group γ, and non-aromatic heterocyclylsulfonyl optionally substituted by substituent group γ'.

A preferred form of each symbol in the compound represented by the formula (I), (I'), or (II) will be described below. Examples of the compound represented by the formula (I), (I'), or (II) include forms having all combinations of specific examples given below.

Examples of the ring A include a substituted or unsubstituted non-aromatic heterocycle;

Ring A is preferably a 5- to 7-membered ring having 1 to 3, preferably 1 or 2 O, S and/or N atoms, more preferably a ring selected from the non-aromatic heterocycles described above. One preferred embodiment of ring A is the following ring (a), (b) or (c), more preferably ring (a) or (b):

[Chemical Formula 15]

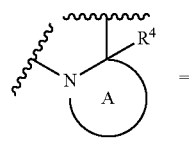

=

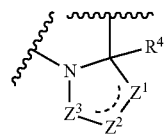

(a)

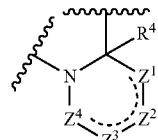

(b)

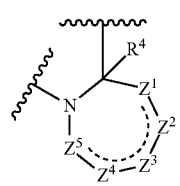

(c)

$Z^1$, $Z^2$, $Z^3$, $Z^4$ and $Z^5$ are each independently $CR^{5a}R^{5b}$, $CR^{5a}$, Q, N, $NR^{5c}$, or S, wherein the number of heteroatoms constituting the ring structure of the A ring in $Z^1$, $Z^2$, $Z^3$, $Z^4$ and $Z^5$ is 0 or 1.

One preferred embodiment of $Z^1$ is $CR^{5a}R^{5b}$, S or $NR^{5c}$, more preferably $CR^{5a}R^{5b}$.

One preferred embodiment of $Z^2$ is $CR^{5a}R^{5b}$, O, S or $NR^{5c}$, more preferably $CR^{5a}R^{5b}$, O or NRS, particularly preferably $CR^{5a}R^{5b}$ or O.

One preferred embodiment of $Z^3$ is $CR^{5a}R^{5b}$, O, S or $NR^{5c}$, more preferably $CR^{5a}R^{5b}$ or O, particularly preferably $CR^{5a}R^{5b}$.

One preferred embodiment of $Z^4$ is $CR^{5a}R^{5b}$, O, S or $NR^{5c}$, more preferably $CR^{5a}R^{5b}$.

One preferred embodiment of $Z^5$ is $CR^{5a}R^{5b}$, O, S or $NR^{5c}$, more preferably $CR^{5a}R^{5b}$.

Alternatively, $Z^1$ and $Z^3$, $Z^1$ and $Z^4$, $Z^1$ and $Z^5$, $Z^2$ and $Z^4$, $Z^2$ and $Z^5$, $Z^3$ and $Z^5$, $R^4$ and $Z^2$, $R^4$ and $Z^3$, $R^4$ and $Z^4$ or $R^4$ and $Z^5$ may be taken together to form a substituted or unsubstituted C1-C4 cross-link. Preferably, $Z^1$ and $Z^3$, $Z^1$ and $Z^4$, $Z^1$ and $Z^5$, $Z^2$ and $Z^4$, $Z^2$ and $Z^5$ or $Z^3$ and $Z^5$ may be taken together to form a substituted or unsubstituted (C1-C4) cross-link.

Ring A may further have ring B as shown below. In this case, $Z^1$, $Z^2$, $Z^3$, $Z^4$ and $Z^5$ constituting ring B are each independently $CR^{5a}$, C or N.

[Chemical Formula 16]

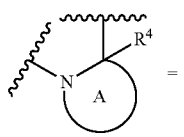
(a1)

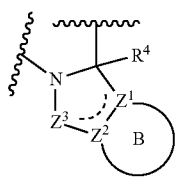
(b1)

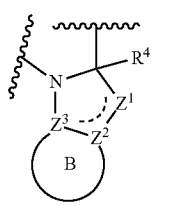
(c1)

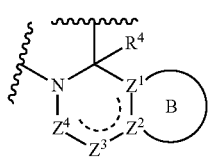
(d1)

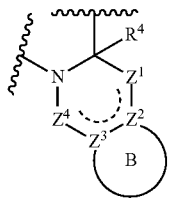
(e1)

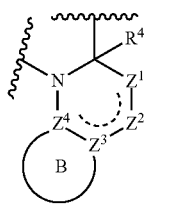
(f1)

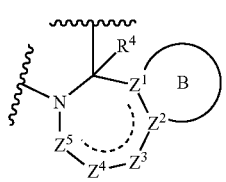
(g1)

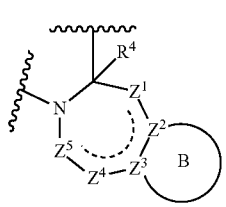

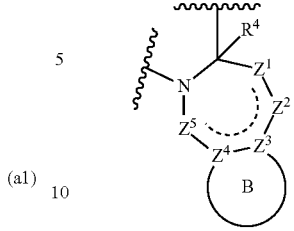
(h1)

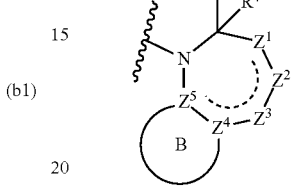
(i1)

Ring A is more preferably ring (a1), (b1), (c1), or (e1), particularly preferably ring (a1) or (b1).

Ring B is preferably a substituted or unsubstituted 3- to 7-membered carbocycle (wherein examples of the substituent include alkyl, halogen, hydroxy, or haloalkyl) or a substituted or unsubstituted 4- to 7-membered heterocycle (wherein examples of the substituent include alkyl, halogen, hydroxy, or haloalkyl), more preferably a benzene ring, a 5- or 6-membered unsubstituted carbocycle or a 5- or 6-membered unsubstituted heterocycle.

Another preferred embodiment of ring A includes the following rings

[Chemical Formula 17]

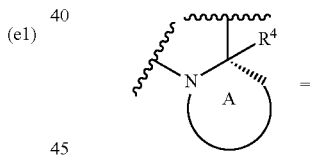

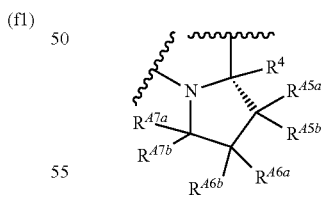
(a2)

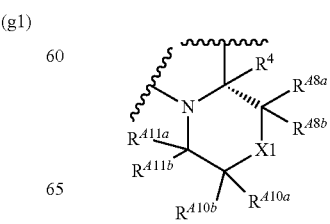
(b2)

-continued (c2)

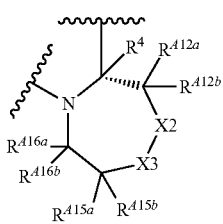

A further preferred embodiment of ring A is the following rings:

[Chemical Formula 18]

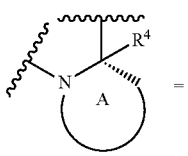
(a2)

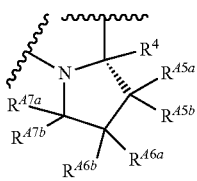
(b3)

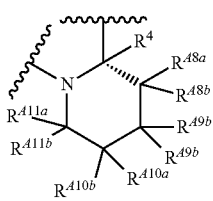
(b4)

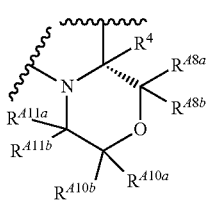

A more preferred embodiment of ring A is ring (a2) or (b3).

Examples of X1 include $CR^{A9a}R^{A9b}$, O or $NR^{A9c}$.

One preferred embodiment of X1 is $CR^{A9a}R^{A9b}$ or O.

Examples of X2 include $CR^{A13a}R^{A13b}$, O or $NR^{A13c}$.

One preferred embodiment of X2 is $CR^{A13a}R^{A13b}$ or O.

Examples of X3 include $CR^{A14a}R^{A9b}$, O or $NR^{A14c}$.

One preferred embodiment of X3 is $CR^{A14a}R^{A14b}$ or O.

Provided that when either X2 or X3 is $NR^{A13c}$, $NR^{A14c}$ or O, the other of X2 or X3 is $CR^{A13a}R^{A13b}$ or $CR^{A14a}R^{A14b}$.

Examples of $R^{A5a}$, $R^{A5b}$, $R^{A6a}$, $R^{A6b}$, $R^{A7a}$ and $R^{A7b}$ each include independently hydrogen, alkyl, alkyloxy and alkyloxyalkyl.

One preferred embodiment of $R^{A5a}$ is hydrogen or alkyl, preferably hydrogen.

One preferred embodiment of $R^{A5b}$ is hydrogen or alkyl, preferably hydrogen.

One preferred embodiment of $R^{A6a}$ is hydrogen, alkyl or alkyloxyalkyl, preferably hydrogen.

One preferred embodiment of $R^{A6b}$ is hydrogen.

One preferred embodiment of $R^{A7a}$ is hydrogen, alkyl or alkyloxyalkyl, preferably alkyloxyalkyl.

One preferred embodiment of $R^{A7b}$ is hydrogen.

$R^{A5a}$ and $R^{A6a}$, or $R^{A6a}$ and $R^{A7a}$ may be taken together with the adjacent atoms to form an aromatic carbocycle optionally substituted with halogen, a 3- to 6-membered non-aromatic carbocycle optionally substituted with halogen or a 4- to 6-membered non-aromatic heterocycle optionally substituted with halogen (provided that $R^{A5b}$ and $R^{A6b}$, or $R^{A6b}$ and $R^{A7b}$ are taken together to form a bond when forming an aromatic carbocycle).

$R^{A5b}$ and $R^{A6b}$ may be taken together to form a bond.

$R^{A6a}$ and $R^{A6b}$ may be taken together with the adjacent atom to form a 3- to 6-membered non-aromatic carbocycle or a 4- to 6-membered non-aromatic heterocycle.

Examples of $R^{A8a}$, $R^{A8b}$, $R^{A9a}$, $R^{A9b}$, $R^{A10a}$, $R^{A10b}$, $R^{A11a}$ and $R^{A11b}$ each include independently hydrogen, alkyl, haloalkyl, alkyloxy or alkyloxyalkyl.

One preferred embodiment of $R^{A8a}$ is hydrogen or alkyl, preferably hydrogen.

One preferred embodiment of $R^{A8b}$ is hydrogen or alkyl, preferably hydrogen.

One preferred embodiment of $R^{A9a}$ is hydrogen, alkyl or alkyloxyalkyl.

One preferred embodiment of $R^{A9b}$ is hydrogen or alkyl, preferably hydrogen.

One preferred embodiment of $R^{A10a}$ is hydrogen, alkyl or alkyloxy, preferably hydrogen.

One preferred embodiment of $R^{A10b}$ is hydrogen.

One preferred embodiment of $R^{A11a}$ is hydrogen or alkyl, preferably hydrogen.

One preferred embodiment of $R^{A11b}$ is hydrogen.

$R^{A8a}$ and $R^{A10a}$, or $R^{A8a}$ and $R^{A11a}$ may be taken together to form a C1-C3 cross-link.

$R^{A10a}$ and $R^{A11a}$ may be taken together with the adjacent atoms to form a 5-membered non-aromatic carbocycle.

$R^{A9a}$ and $R^{A9b}$ may be taken together with the adjacent atom to form a 4-membered non-aromatic carbocycle or a 5-membered non-aromatic heterocycle.

$R^{A8a}$ and $R^{A9a}$ may be taken together to form a bond.

$R^{A9c}$ is hydrogen, alkyl, alkyloxyalkyl, alkyloxycarbonyl, alkylcarbamoyl, aromatic carbocyclyl, aromatic heterocyclyl, aromatic carbocyclylalkyl, or aromatic heterocyclylalkyl.

$R^{A12a}$, $R^{A12b}$, $R^{A13a}$, $R^{A13b}$, $R^{A14a}$, $R^{A14b}$, $R^{A15a}$, $R^{A15b}$, $R^{A16a}$, and $R^{A16b}$ are each independently hydrogen, alkyl, alkyloxy or alkyloxyalkyl.

$R^{A13c}$ or $R^{A14c}$ is each independently alkyl, alkyloxyalkyl, alkyloxycarbonyl, alkylcarbamoyl, aromatic carbocyclyl, aromatic heterocyclyl, aromatic carbocyclylalkyl, or aromatic heterocyclylalkyl.

Examples of Q include a 5-membered aromatic heterocycle.

One preferred embodiment of Q is a 5- or 6-membered heterocycle optionally substituted by halogen, alkyl, haloalkyl, alkyloxy, haloalkyloxy, or alkylamino.

Q is preferably any of the following rings optionally substituted by halogen, alkyl, haloalkyl, alkyloxy, haloalkyloxy, or alkylamino (provided that the left bond is bonded to L):

[Chemical Formula 19]
(1)
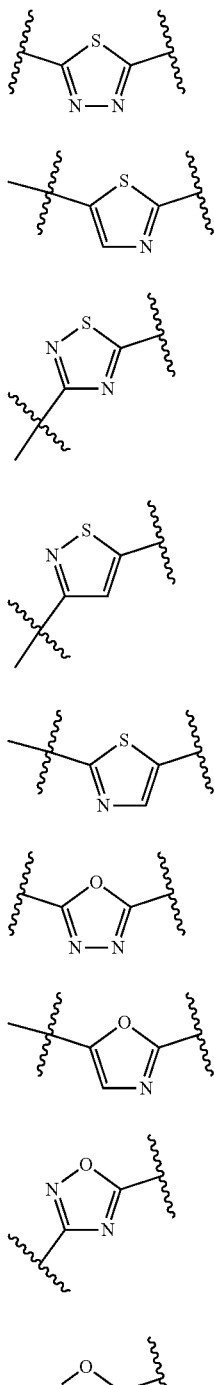
(2)
(3)
(4)
(5)
(6)
(7)
(8)
(9)
(10)
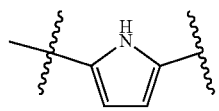 (11)
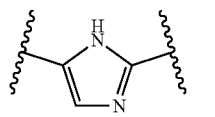 (12)
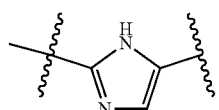 (13)
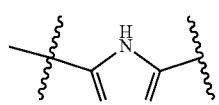 (14)
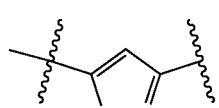 (15)
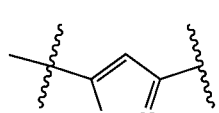 (16)
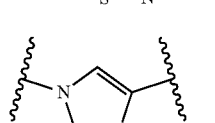 (17)
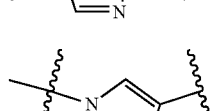 (18)
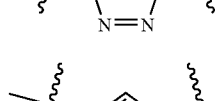 (19)
Q is more preferably any of the following rings optionally substituted by halogen, alkyl, haloalkyl, alkyloxy, haloalkyloxy, or alkylamino (provided that the left bond is bonded to L):
[Chemical Formula 20]
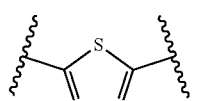 (1)
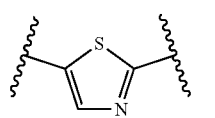 (2)

Another preferred embodiment of Q is the following rings (the left bond is bonded to L):

[Chemical Formula 21]

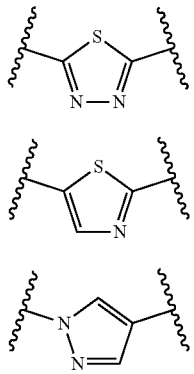

(1)

(2)

(20)

A more preferred embodiment of Q is the ring shown in (1).

Examples of $R^1$ each independently include halogen, alkyl, haloalkyl, alkyloxy, cyano, or haloalkyloxy.

One preferred embodiment of $R^1$ is halogen, alkyl or haloalkyl.

$R^1$ is preferably halogen.

L is substituted or unsubstituted alkylene (wherein the substituent is, for example, halogen), more preferably methylene.

Examples of $R^3$ include substituted or unsubstituted alkyl (wherein the substituent is, for example, halogen, alkyloxy, haloalkyloxy, non-aromatic cyclyl, or non-aromatic heterocyclyl), substituted or unsubstituted non-aromatic carbocyclyl (wherein the substituent is, for example, halogen), or substituted or unsubstituted non-aromatic heterocyclyl (wherein the substituent is, for example, halogen).

One preferred embodiment of $R^3$ is alkyl or haloalkyl.

$R^3$ is preferably alkyl.

Examples of R 4 include hydrogen and alkyl.

One preferred embodiment of $R^4$ is hydrogen or methyl, and a more preferred form is hydrogen.

Examples of $R^{5a}$ and $R^{5b}$ each independently include hydrogen, halogen, substituted or unsubstituted alkyl (wherein the substituent is, for example, halogen or alkyloxy) and substituted or unsubstituted alkyloxy (wherein the substituent is, for example, halogen), and $R^{5a}$ and $R^{5b}$ on the same carbon atom may be taken together to form a substituted or unsubstituted non-aromatic carbocycle (wherein the substituent is, for example, halogen) or a substituted or unsubstituted non-aromatic heterocycle (wherein the substituent is, for example, halogen).

One preferred embodiment of $R^{5a}$ and $R^{5b}$ is each independently hydrogen, alkyl, or alkyloxyalkyl.

Examples of $R^{5c}$ each independently include hydrogen, substituted or unsubstituted alkyl (wherein the substituent is, for example, alkyloxy, aromatic carbocyclyl, aromatic heterocyclyl), substituted or unsubstituted alkylcarbonyl, substituted or unsubstituted alkyloxycarbonyl, substituted or unsubstituted carbamoyl (wherein the substituent is, for example, alkyl), substituted or unsubstituted aromatic carbocyclyl, substituted or unsubstituted non-aromatic carbocyclyl, substituted or unsubstituted aromatic heterocyclyl, or a substituted and unsubstituted non-aromatic heterocyclyl.

One preferred embodiment of $R^{5c}$ is each independently hydrogen, or substituted or unsubstituted alkyl (wherein the substituent is, for example, alkyloxy).

Examples of n include integers of 1 to 3.

One preferred embodiment of n is an integer of 2 or 3.

A more preferred embodiment of n is an integer of 1 or 2.

The carbon atom adjacent to $R^4$ preferably has the following configuration:

[Chemical Formula 22]

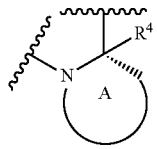

wherein each symbol is as defined above.

Examples of the C ring include a benzene ring and a pyridine ring.

One preferred embodiment of the C ring is a benzene ring.

The compound represented by the formula (I') is preferably a compound represented by the following formula (I-2):

[Chemical Formula 23]

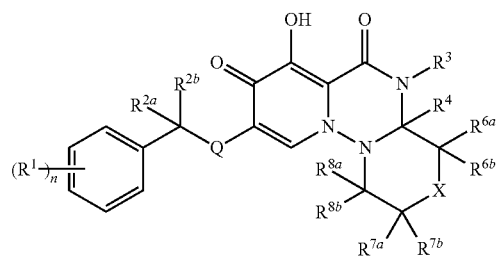

(I-2)

A preferred embodiment of each symbol in the compound represented by the formula (I-2) will be described below. Examples of the compound represented by the formula (I-2) include embodiments having all combinations of specific examples given below.

$R^1$, $R^3$, $R^4$, Q, n and the configuration of the carbon atom adjacent to $R^4$ are the same as the preferred embodiments in the compound represented by the formula (I').

One preferred embodiment of each of $R^{2a}$ and $R^{2b}$ is hydrogen.

Another preferred embodiment of $R^{2a}$ and $R^{2b}$ is a carbocycle together with the adjacent carbon atom.

$R^{2a}$ is preferably hydrogen.

$R^{2b}$ is preferably hydrogen or methyl.

$R^{2a}$ and $R^{2b}$ are preferably a C3-C4 non-aromatic carbocycle together with the adjacent carbon atom.

One preferred embodiment of X is $CR^{9a}R^{9b}$, $NR^{10}$, or O, more preferably $CR^{9a}R^{9b}$ or $NR^{10}$, particularly preferably $CR^{9a}R^{9b}$.

One preferred embodiment of $R^{6a}$, $R^{6b}$, $R^{7a}$, $R^{7b}$, $R^{8a}$, $R^{8b}$, $R^{9a}$, and $R^{9b}$ is each independently hydrogen, or substituted or unsubstituted alkyl.

$R^{6a}$, $R^{6b}$, $R^{7a}$, $R^{7b}$, $R^{8a}$, $R^{8b}$, $R^{9a}$, and $R^{9b}$ are preferably, each independently, hydrogen, or substituted or unsubstituted alkyl (wherein the substituent is, for example, halogen), particularly preferably hydrogen or methyl.

One preferred embodiment of $R^{1a}$ is substituted or unsubstituted alkyl.

A feature of the compound of the present invention is that ring A is formed in the formula (I), (I'), (I-2) or (II) to attain excellent resistance profile, in vivo kinetics and safety. Another feature of the compound of the present invention is that the configuration of ring A is defined to attain excellent resistance profile.

The compound of the present invention is not limited to a specific isomer and includes all possible isomers (e.g., keto-enol isomers, imine-enamine isomers, diastereomers, optical isomers, and rotational isomers), racemates or mixtures thereof, unless otherwise specified.

The pharmaceutically acceptable salts of the compounds of the present invention include, for example, salts of the compounds of the present invention with alkaline metals (e.g., lithium, sodium, potassium), alkaline earth metals (e.g., calcium, barium), magnesium, transition metals (e.g., zinc, iron), ammonia, organic bases (e.g., trimethylamine, triethylamine, dicyclohexylamine, ethanolamine, diethanolamine, triethanolamine, meglumine, ethylenediamine, pyridine, picoline, quinoline) or amino acids, or salts of the compounds of the present invention with inorganic acids (e.g., hydrochloric acid, sulfuric acid, nitric acid, carbonic acid, hydrobromic acid, phosphoric acid, hydroiodic acid) or organic acids (e.g., formic acid, acetic acid, propionic acid, trifluoroacetic acid, citric acid, lactic acid, tartaric acid, oxalic acid, maleic acid, fumaric acid, mandelic acid, glutaric acid, malic acid, benzoic acid, phthalic acid, ascorbic acid, benzenesulfonic acid, p-toluenesulfonic acid, methanesulfonic acid, ethanesulfonic acid). These salts can be formed by the usual methods.

The compound of the present invention or the pharmaceutically acceptable salt thereof may form a solvate (e.g., a hydrate), cocrystals and/or a crystal polymorph. The present invention also encompasses such various solvates, cocrystals and crystal polymorphs. The "solvate" may coordinate the compound of the present invention with an arbitrary number of solvent molecules (e.g., water molecules). The compound of the present invention or the pharmaceutically acceptable salt thereof, when left in the atmosphere, may attach adsorbed water or may form a hydrate, by absorbing moisture. The compound of the present invention or the pharmaceutically acceptable salt thereof may form a crystal polymorph by recrystallization. The "cocrystals" mean that the compound of the present invention or the salt and a counter molecule coexist in the same crystal lattice, and may be formed with an arbitrary number of counter molecules.

The compound of the present invention or the pharmaceutically acceptable salt thereof may form a prodrug. The present invention also encompasses such various prodrugs. The prodrug is a derivative of the compound of the present invention having a chemically or metabolically decomposable group, and is a compound that becomes the pharmaceutically active compound of the present invention by solvolysis or under physiological conditions in vivo. The prodrug includes, for example, a compound that is converted to the compound represented by the formula (I), (I'), (I-2) or (II) through enzymatic oxidation, reduction, hydrolysis, or the like under physiological conditions in vivo, and a compound that is converted to the compound represented by the formula (I), (I'), (I-2) or (II) through hydrolysis by gastric juice or the like. Methods for selecting and preparing suitable prodrug derivatives are described in, for example, "Design of Prodrugs, Elsevier, Amsterdam, 1985". Prodrugs themselves may have some activity.

When the compound represented by the formula (I), (I'), (I-2) or (II) or the pharmaceutically acceptable salt thereof has a hydroxyl group, examples of the prodrug include prodrugs such as acyloxy derivatives and sulfonyloxy derivatives produced by reacting the compound having a hydroxyl group with an appropriate acyl halide, an appropriate acid anhydride, an appropriate sulfonyl chloride, an appropriate sulfonyl anhydride and a mixed anhydride, or using a condensing agent. For example, they include $CH_3COO$—, $C_2H_5COO$—, tert-BuCOO—, $C_{15}H_{31}COO$—, PhCOO—, (m-NaOOCPh)COO—, $NaOOCCH_2CH_2COO$—, $CH_3CH(NH_2)COO$—, $CH_2N(CH_3)_2COO$—, $CH_3SO_3$—, $CH_3CH_2SO_3$—, $CF_3SO_3$—, $CH_2FSO_3$—, $CF_3CH_2SO_3$—, $p$-$CH_3O$-$PhSO_3$—, $PhSO_3$— and $p$-$CH_3PhSO_3$.

(Method for Producing Compound of Present Invention)

The compound of the present invention can be produced by, for example, general synthesis methods shown below. Extraction, purification, and the like can be performed by treatment performed in usual experiments of organic chemistry.

The compound of the present invention can be synthesized with reference to an approach known in the art.

(Process 1)

[Chemical Formula 24]

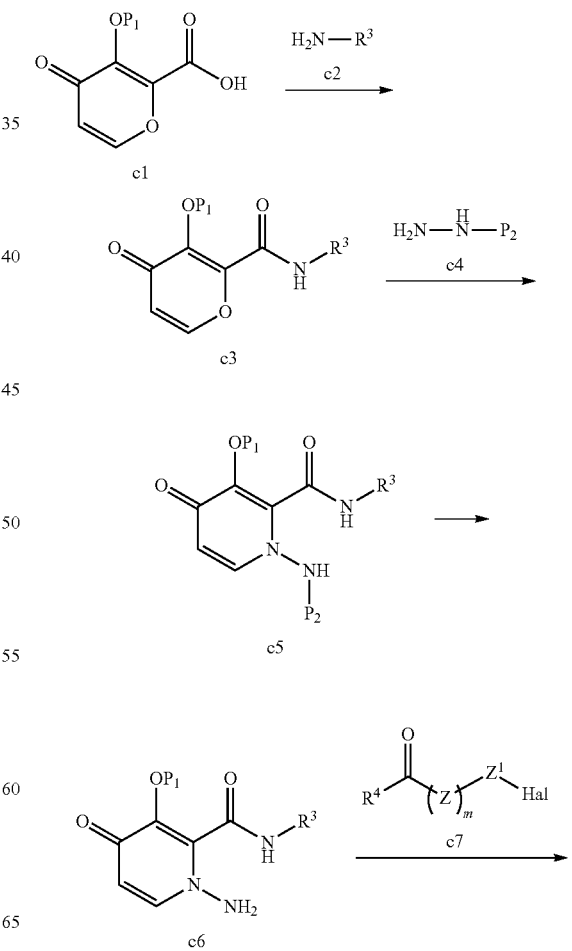

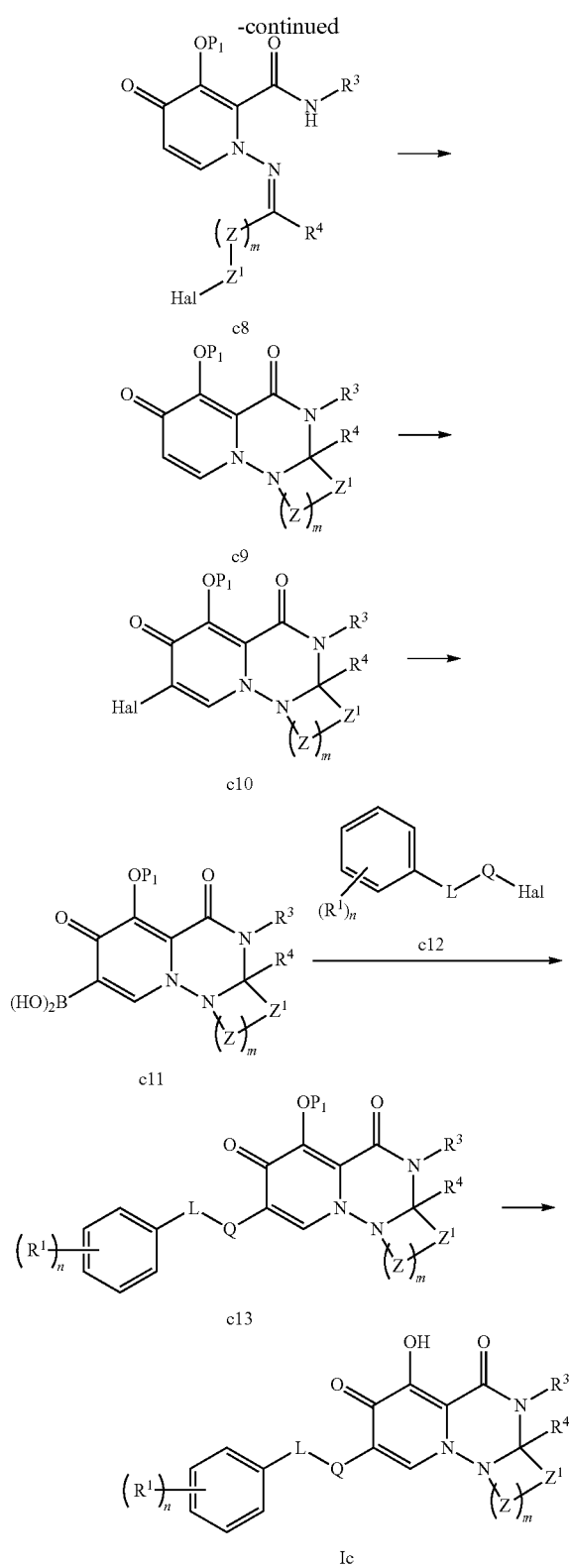

example, $P^1$ is aromatic carbocyclylalkyl or the like, and $P^2$ is alkyloxycarbonyl or the like; and the other symbols are as defined above.

Step 1

Compound c3 can be obtained by adding a condensing agent such as HATU, WSC-HCl, or PyBOP to compound c1 which can be commercially available or prepared by a known method in the presence of a solvent such as DMF, DMA, NMP, THF, chloroform, or dichloromethane, adding thereto compound c2 which can be commercially available or prepared by a known method, and a tertiary amine such as triethylamine, N-methylmorpholine, pyridine, or diisopropylethylamine, and reacting the mixture at 10° C. to 60° C., preferably 20° C. to 40° C., for 0.1 hours to 24 hours, preferably 1 hour to 12 hours.

Step 2

Compound c5 can be obtained by adding compound c4 which can be commercially available or prepared by a known method, and an acid such as acetic acid, pyridinium p-toluenesulfonate, p-toluenesulfonic acid, or methanesulfonic acid to compound c3 in the presence of a solvent such as DMF, DMA, or NMP, and reacting the mixture at 20° C. to 120° C., preferably 60° C. to 100° C., for 0.1 hours to 24 hours, preferably 1 hour to 12 hours.

Step 3

Compound c6 can be obtained by subjecting compound c5 to the known general deprotection reaction of amino-protective groups.

Step 4

Compound c8 can be obtained by adding compound c7 which can be commercially available or prepared by a known method, and an acid such as acetic acid, p-toluenesulfonic acid, or methanesulfonic acid to compound c6 in the presence of a solvent such as dichloromethane, dichloroethane, chloroform, methanol, ethanol, toluene, DMF, DMA, or THF, and reacting the mixture at 20° C. to 130° C., preferably 20° C. to 100° C., for 0.1 hours to 24 hours, preferably 1 hour to 12 hours.

Step 5

Compound c9 can be obtained by adding a base such as cesium carbonate or potassium carbonate and a salt such as sodium iodide or potassium iodide to compound c8 in the presence of a solvent such as DMF, DMA, NMP, or THF, and reacting the mixture at 0° C. to 60° C., preferably 0° C. to 40° C., for 0.1 hours to 24 hours, preferably 1 hour to 12 hours.

Step 6

J can be obtained by adding a halogenation reagent such as bromine, NBS, NCS, or NIS to compound c9 in a solvent such as dichloromethane, dichloroethane, acetonitrile or DMF, and, when Hal is bromo, reacting the mixture at −30° C. to 50° C., preferably −10° C. to 20° C., for 0.1 hours to 10 hours, preferably 0.5 hours to 2 hours. When Hal is chloro or iodo, compound c10 can be obtained by reacting the mixture at 10° C. to 150° C., preferably 60° C. to 120° C., for 0.5 hours to 24 hours, preferably 1 hour to 6 hours.

Step 7

Compound c1 can be obtained by adding a palladium catalyst such as $Pd(PPh_3)_4$, $Pd(OAc)_2$, $Pd(PPh_3)_2Cl_2$, $Pd(dppf)_2Cl_2$ or Pd(dtbpf), a base such as potassium acetate, sodium acetate, potassium carbonate, or potassium phosphate, and bis(pinacolato)diboron to compound c10 in a solvent such as dioxane, DMF, DME, THF, or DMSO, or a mixed solvent, and reacting the mixture at 0° C. to 150° C., preferably 60° C. to 120° C., for 0.5 hours to 24 hours, preferably 1 hour to 12 hours, in a nitrogen atmosphere.

wherein $P^1$ is a hydroxy-protective group; $P^2$ is an amino-protective group; Z is $Z^2$, $Z^3$, $Z^4$ or $Z^5$; m is an integer of 1 to 4; Hal is halogen; each of $P^1$ and $P^2$ can be a group that can be protected and/or deprotected by a method described in, for example, Protective Groups in Organic Synthesis, Theodora W Greene (John Wiley & Sons Inc.), and, for Step 8

Compound c13 can be obtained by adding a palladium catalyst such as $Pd(PPh_3)_4$, $Pd(OAc)_2$, $Pd(PPh_3)_2Cl_2$, $Pd(dppf)_2Cl_2$ or $Pd(dtbpf)$, a base such as potassium carbonate, sodium carbonate, cesium carbonate or potassium phosphate, and compound c12 which is commercially available or prepared by a known method to compound c1 in a solvent such as dioxane, DMF, DME, THF, or water, or a mixed solvent, and reacting the mixture at 0° C. to 150° C., preferably 60° C. to 120° C., for 0.5 hours to 24 hours, preferably 1 hour to 12 hours, in a nitrogen atmosphere.

Step 9

Compound Ic can be obtained by subjecting compound c13 to the known general deprotection reaction of hydroxy-protective groups.

(Process 2)

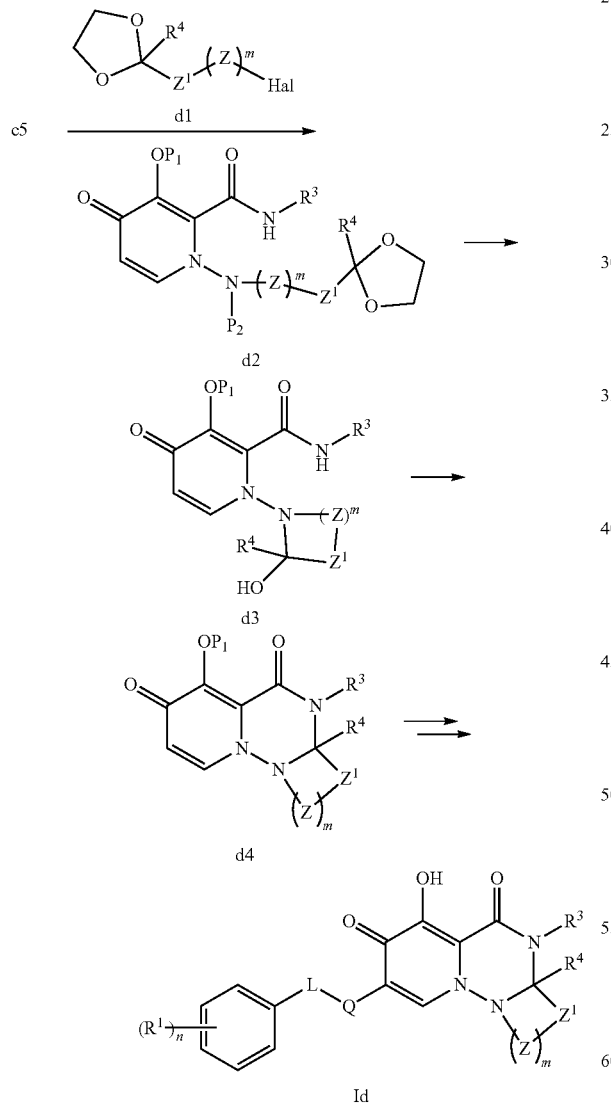

wherein each symbol is as defined above.

Step 1

Compound d2 can be obtained by adding a base such as cesium carbonate, potassium carbonate, or triethylamine and compound d1 which can be commercially available or prepared by a known method to compound c5 in the presence of a solvent such as DMF, DMA, NMP, or THF, further adding, when Hal is chloro, a salt such as sodium iodide or potassium iodide thereto, and reacting the mixture at 0° C. to 60° C., preferably 20° C. to 40° C., for 0.1 hours to 24 hours, preferably 1 hour to 12 hours.

Step 2

Compound d3 can be obtained by subjecting compound d2 to the known general deprotection reaction of acetals.

Step 3

Compound d4 can be obtained by adding an acid such as acetic acid, p-toluenesulfonic acid, or mesylic acid to compound d3 in the presence of a solvent such as dichloromethane, dichloroethane, chloroform, methanol, ethanol, toluene, DMF, DMA, or THF, and reacting the mixture at 20° C. to 130° C., preferably 80° C. to 120° C., for 0.1 hours to 24 hours, preferably 1 hour to 12 hours.

Step 4

Compound Id can be synthesized according to steps 6 to 9 of process 1 described above.

(Process 3)

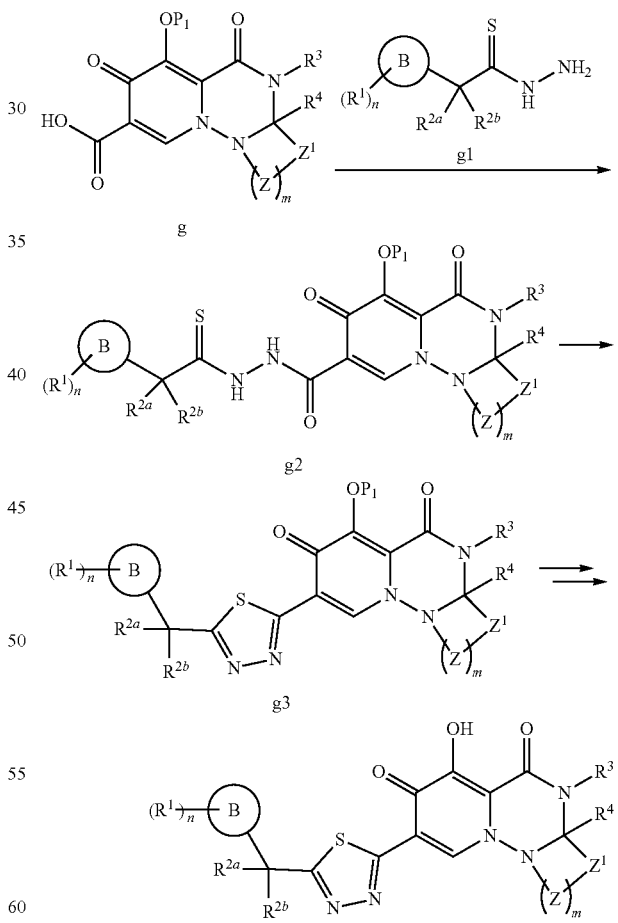

wherein the other symbols are as defined above.

Step 1

Compound g2 can be obtained by adding a base such as triethylamine or diisopropylethylamine and ethyl chloroformate to form an acid chloride, then adding compound g1, which can be commercially available or prepared by a known method, to compound g in the presence of a solvent such as dichloromethane, dichloroethane, chloroform, DMF, DMA, NMP, or THF, and reacting the mixture at 0° C. to 60° C., preferably 0° C. to 20° C., for 0.1 hours to 24 hours, preferably 1 hour to 12 hours.

Step 2

Compound g3 can be obtained by allowing an acid such as T3P, trifluoroacetic acid, phosphoric acid, hydrochloric acid, sulfuric acid or hydrobromic acid to act on compound g2 in the presence of a solvent such as ethyl acetate, dichloromethane, dichloroethane, chloroform, dioxane, DMF, DMA, or THF, and reacting the mixture at 20° C. to 130° C., preferably 60° C. to 100° C., for 0.1 hours to 24 hours, preferably 1 hour to 12 hours.

Step 3

Compound Ic can be synthesized according to step 9 of process 1.

The compound of the present invention thus obtained may be further chemically modified to synthesize another compound. When a reactive functional group (e.g., OH, COOH, and $NH_2$) is present at a side chain moiety or the like during the reaction, this functional group may be protected before the reaction and deprotected after the reaction, if desired.

Examples of the protective groups (amino-protective group, hydroxy-protective group, etc.) can include protective groups described in, for example, Protective Groups in Organic Synthesis, T. W. Greene, John Wiley & Sons Inc. (1991), such as ethoxycarbonyl, tert-butoxycarbonyl, acetyl, and benzyl. Methods for introducing and eliminating the protective groups can be performed by methods routinely used in organic synthetic chemistry [see, for example, Protective Groups in Organic Synthesis, T. W. Greene, John Wiley & Sons Inc. (1991)] or methods equivalent thereto. The conversion of a functional group contained in each substituent can also be performed by a known method [e.g., Comprehensive Organic Transformations, R. C. Larock (1989)] other than the production methods described above. Some compounds of the present invention can be further converted to novel derivatives with the compounds as intermediates for synthesis. The intermediate and the compound of interest in each production method described above can be subjected to a purification method routinely used in organic synthetic chemistry, for example, neutralization, filtration, extraction, washing, drying, concentration, recrystallization, or various chromatography techniques, and thereby isolated or purified. Alternatively, the intermediate may be subjected to next reaction without further purification in particular.

The compound of the present invention is useful as a medicament, for example, an antiviral drug. The compound of the present invention has a marked inhibitory effect on virus integrase. Accordingly, the compound of the present invention can be expected to have a prophylactic or therapeutic effect on various diseases caused by viruses that grow by producing at least integrase at the time of infection in animal cells, and is useful as, for example, a retrovirus (e.g., HIV-1, HIV-2, HTLV-1, SIV, and FIV) integrase inhibitor and useful as an anti-HIV drug. A preferred compound also has the following characteristics as pharmacokinetics in the body: the blood concentration is high; the duration of an effect is long; the transitivity to tissue is remarkable; and/or the like. In addition, a preferred compound is safe with regard to a side effect (e.g., inhibition of CYP enzymes, mutagenicity, the QT interval prolongation of the electrocardiogram, and arrhythmia).

The compound of the present invention can also be used in combination therapy with an anti-HIV drug having the different action mechanism, such as a reverse transcriptase inhibitor, a protease inhibitor and/or an entry inhibitor.

The use described above includes not only use as an anti-HIV combination but use as a concomitant agent that elevates the anti-HIV activity of another anti-HIV drug, as in cocktail therapy or the like.

The compound of the present invention can be used for preventing infection with a retrovirus vector from spreading to tissues other than a tissue of interest when a retrovirus vector based on HIV or MLV is used in the field of gene therapy. Particularly, when cells or the like are infected with the vector in vitro and brought back to the body, the administration of the compound of the present invention beforehand can prevent the unnecessary infection of the body.

A pharmaceutical composition of the present invention can be administered orally or parenterally. Methods for parenteral administration include dermal, subcutaneous, intravenous, intraarterial, intramuscular, intraperitoneal, transmucosal, inhalation, transnasal, ophthalmic, inner ear or vaginal administration and the like.

In case of oral administration, any formulations, which are usually used, such as oral solid formulations (e.g., tablets, powders, granules, capsules, pills, films or the like), oral liquid formulations (e.g., suspension, emulsion, elixir, syrup, lemonade, spirit, aromatic water, extract, decoction, tincture or the like) and the like may prepared according to the usual method and administered. The tablets can be sugar-coated tablets, film-coated tablets, enteric-coating tablets, sustained-release tablets, troche tablets, sublingual tablets, buccal tablets, chewable tablets or orally dispersing tablets. Powders and granules can be dry syrups. Capsules can be soft capsules, micro capsules or sustained-release capsules.

In case of parenteral administration, any formulations, which are usually used, such as injections, drips, external preparations (e.g., ophthalmic drops, nasal drops, ear drops, aerosols, inhalations, lotion, infusion, liniment, mouthwash, enema, ointment, plaster, jelly, cream, patch, cataplasm, external powder, suppository or the like) and the like can be suitably administered. Injections can be emulsions whose type is O/W, W/O, O/W/O, W/O/W or the like.

The pharmaceutical composition may be manufactured by mixing an effective amount of the compound of the present invention with various pharmaceutical additives suitable for the formulation, such as excipients, binders, disintegrants, lubricants and the like, if necessary. Furthermore, the pharmaceutical composition can be for pediatric patients, geriatric patients, serious cases or operations by appropriately changing the effective amount of the compound of the present invention, formulation and/or various pharmaceutical additives. For example, a pediatric pharmaceutical composition can be administered to newborns (under 4 weeks after birth), infants (4 weeks after birth to under 1 year old), young children (1 or more and under 7 years old), children (7 or more and under 15 years old) or patients who are 15 to 18 years old. For example, a geriatric pharmaceutical composition can be administered to patients who are 65 or more years old.

Although the dose of a pharmaceutical composition of the present invention should be determined in consideration of the patient's age and body weight, the type and degree of diseases, the administration route and the like, a usual oral dose is within the range of 0.05 to 100 mg/kg/day and preferably 0.1 to 10 mg/kg/day. For parenteral administration, the dose differs largely depending on an administration route and is within the range of usually 0.005 to 10 mg/kg/day, preferably 0.01 to 1 mg/kg/day. This dose can be administered once a day to once a month or once three months.

EXAMPLES

Hereinafter, Examples will be described.

Abbreviation

Bn: benzyl
DMA: dimethylacetamide
DME: dimethoxyethane
DMF: dimethylformamide
DMSO: dimethyl sulfoxide
HATU: O-(7-azabenzotriazol-1-yl)-N,N,N',N'-tetramethyl-uronium hexafluorophosphate
NBS: N-bromosuccinimide
NCS: N-Chlorosuccinimide
NIS: N-Iodosuccinimide
NMP: N-methylpyrrolidone
PyBOP: (benzotriazol-1-yloxy)tripyrrolidinophosphonium hexafluorophosphate
THF: tetrahydrofuran
WSC-HCl: 1-ethyl-3-(3-dimethylaminopropyl)carbodiimide hydrochloride NMR analysis obtained in each Example was conducted at 300 MHz or 400 MHz, and the measurement was performed using DMSO-$d_6$ or CDCl$_3$. NMR data indicated herein may not describe all measured peaks.

In Examples, "No." represents compound number, "Structure" means a chemical structure, and "MS" represents a molecular weight in LC/MS (liquid chromatography/mass spectrometry).

(Measurement conditions)
(A) Column: ACQUITY UPLC® BEH C18 (1.7 μm i.d. 2.1×50 mm) (Waters Corp.)
Flow rate: 0.8 mL/min; UV detection wavelength: 254 nm;
Mobile phase: [A]: an aqueous solution containing 0.1% formic acid, [B]: an acetonitrile solution containing 0.1% formic acid
Linear gradient of 5% to 100% solvent [B] was performed in 3.5 minutes, and then 100% solvent [B] was kept for 0.5 minutes.
(B) Column: Shim-pack XR-ODS (2.2 μm, i.d. 50×3.0 mm) (Shimadzu Corp.)
Flow rate: 1.6 mL/min; UV detection wavelength: 254 nm;
Mobile phase: [A]: an aqueous solution containing 0.1% formic acid, [B]: an acetonitrile solution containing 0.1% formic acid
Gradient: linear gradient of 10% to 100% solvent [B] in 3 minutes was performed, and 100% solvent [B] was kept for 0.5 minute.

Example 1

[Chemical Formula 27]

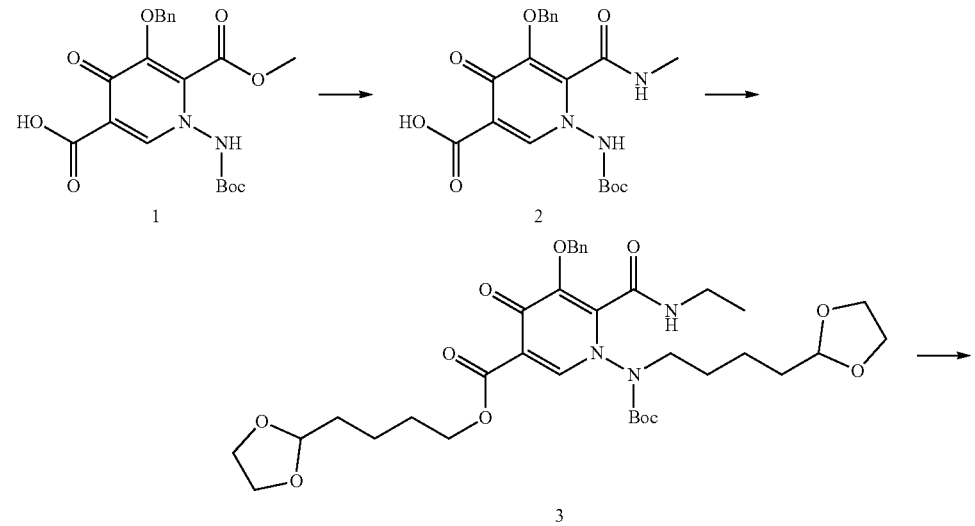

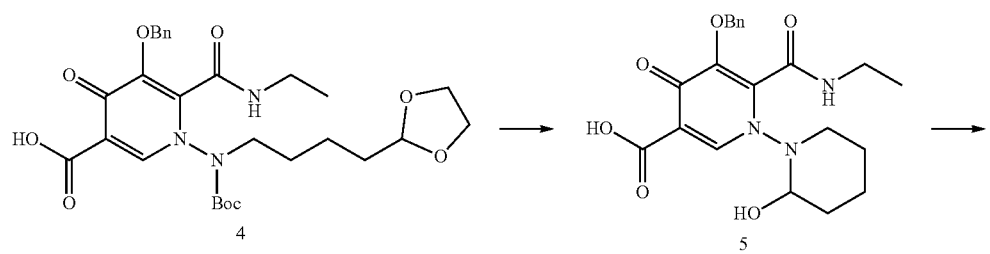

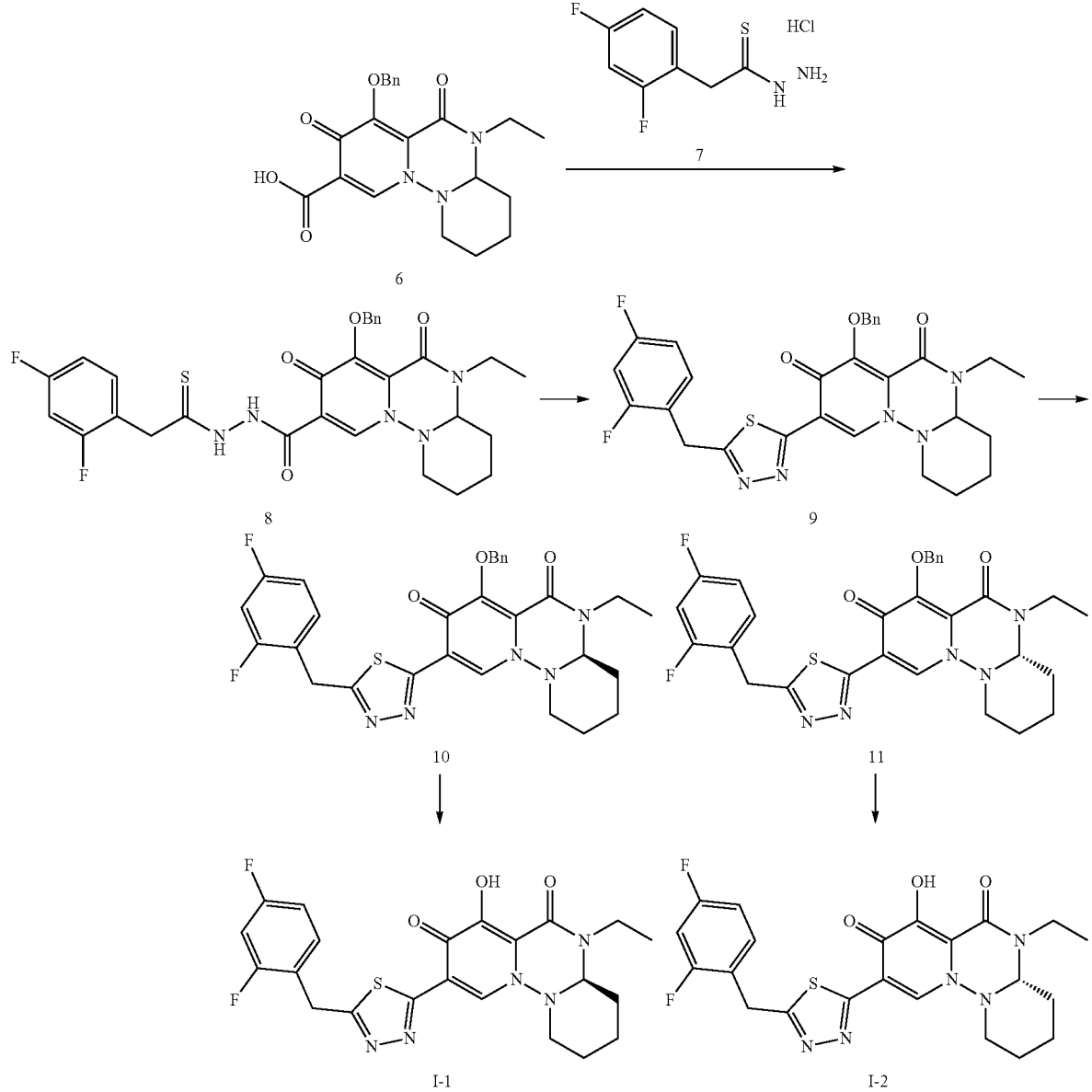

Step 1

To compound 1 (1.50 g, 3.59 mmol), a 2 mol/L solution of ethylamine in methanol (17.9 ml, 35.9 mmol) was added, and the mixture was stirred at 100° C. for 1 hour under microwave irradiation. The solvent in the reaction solution was distilled off under reduced pressure. Then, the residue was rendered acidic by the addition of dilute hydrochloric acid, followed by extraction with ethyl acetate. The organic layer was dried over sodium sulfate, and the solvent was then distilled off. The obtained residue was purified by silica gel column chromatography (chloroform-methanol) to give compound 2 (1.15 g, yield: 74%).

1H-NMR (CDCl$_3$) δ: 14.53 (s, 1H), 8.64 (brs, 1H), 8.46 (s, 1H), 7.37 (m, 5H), 6.57 (brs, 1H), 5.38 (s, 2H), 3.24 (dt, J=14.0, 6.6 Hz, 2H), 1.45 (s, 9H), 1.02 (t, J=7.3 Hz, 4H).

Step 2

To a solution of compound 2 (3 g, 6.95 mmol) in DMF (60 ml), potassium carbonate (2.02 g, 14.6 mmol) and 2-(4-bromobutyl)-1,3-dioxolane (2.53 ml, 16.7 mmol) were added, and the mixture was reacted overnight at room temperature. The reaction solution was neutralized with 1 mol/L hydrochloric acid, followed by extraction with ethyl acetate. The organic layer was washed with water and brine, dried over sodium sulfate, then the solvent was distilled off to give compound 3.

MS: m/z=688 [M+H]+

Step 3

To a solution of compound 3 in THF (47.8 mL), a 2 mol/L aqueous sodium hydroxide solution (17.38 ml, 139 mmol) was added, and the mixture was stirred at room temperature for 2 hours. The reaction solution was neutralized by the addition of 2 mol/L hydrochloric acid in small portions, followed by extraction with ethyl acetate. The organic layer was washed with brine, dried over sodium sulfate, then the solvent was distilled off under reduced pressure to give compound 4.

MS: m/z=560 [M+H]+

Step 4

To a solution of compound 4 in 1,4-dioxane (5 mL), 4 mol/L hydrogen chloride (1,4-dioxane solution, 34.8 ml, 139 mmol) was added, and the mixture was stirred at room temperature for 1 hour. The solvent in the reaction solution was distilled off. Toluene was added to the residue, and the solvent was distilled off again to give compound 5.

MS: m/z=416 [M+H]+

Step 5

To a solution of compound 5 in toluene (50 mL), a few drops of acetic acid were added, and the mixture was stirred at 110° C. for 30 minutes. The solvent in the reaction solution was distilled off, and the obtained residue was solidified from ethanol/isopropyl ether to give compound 6 (2.44 g, yield of 4 steps: 88%).

$^1$H-NMR (CDCl$_3$) δ: 15.1 (s, 1H), 8.48 (s, 1H), 7.57-7.55 (m, 2H), 7.36-7.29 (m, 3H), 5.53 (d, J=10.4 Hz, 1H), 5.36 (d, J=10.4 Hz 1H), 4.93-4.91 (m, 1H), 4.20 (td, J=21.6, 7.2 Hz, 1H), 3.24-3.02 (m, 3H), 2.28-1.73 (m, 5H), 1.41-1.31 (m, 1H), 1.18 (t, J=7.2 Hz, 3H).

Step 6

To a solution of compound 6 (300 mg, 0.755 mmol) in dichloromethane (3 ml), triethylamine (0.419 ml, 3.02 mmol) and ethyl chloroformate (90.0 mg, 0.830 mmol) were added at 0° C., and the mixture was stirred at room temperature for 30 minutes. Compound 7 (216 mg, 0.906 mmol) was added to the reaction solution, and the mixture was stirred at room temperature for 1 hour. The reaction solution was concentrated, and the obtained residue was purified by silica gel column chromatography (chloroform-methanol) to give compound 8 (466 mg, yield: 100%).

MS: m/z=582 [M+H]+

Step 7

To a solution of compound 8 (439 mg, 0.755 mmol) in ethyl acetate (6 ml), a 50% solution of T3P in ethyl acetate (2.25 ml, 7.55 mmol) was added, and the mixture was stirred at 100° C. for 1 hour. A saturated aqueous solution of sodium bicarbonate was added to the reaction solution, followed by extraction with ethyl acetate. The organic layer was washed with water and dried over sodium sulfate, and the solvent was then distilled off. The obtained residue was purified by silica gel column chromatography (chloroform-methanol) to give compound 9 (300 mg, yield: 71%) which was a racemic mixture.

1H-NMR (CDCl$_3$) δ: 8.80 (s, 1H), 7.60 (m, 2H), 7.34-7.27 (m, 4H), 6.85 (t, J=8.9 Hz, 2H), 5.55 (d, J=10.3 Hz, 1H), 5.33 (d, J=10.4 Hz, 1H), 4.97 (m, 1H), 4.46 (s, 2H), 4.40 (m, 1H), 3.23 (m, 1H), 3.10-3.03 (m, 2H), 2.24 (m, 1H), 2.02 (m, 1H), 1.89 (m, 2H), 1.72 (m, 1H), 1.42 (m, 1H), 1.17 (t, J=7.2 Hz, 3H).

Step 8

Compound 9 was optically resolved by SFC to give compounds 10 and 11.
Column: CHIRALPAK IA/SFC (5 μm, i.d. 250×20 mm)
Flow rate: 20 mL/min
UV detection wavelength: 220 nm
Fractionation conditions: a compositional ratio of MeOH/CO2=65/35 was kept, and the solution was sent for 25 minutes.

Step 9

Compound 11 (110 mg, 0.195 mmol) was dissolved in DMF (1.1 ml). To the solution, lithium chloride (83.0 mg, 1.95 mmol) was added, and the mixture was stirred at 90° C. for 2 hours. Water was added to the reaction solution, and the mixture was rendered acidic with a 10% aqueous citric acid solution, followed by extraction with ethyl acetate. The organic layer was washed with water and dried over sodium sulfate, and the solvent was then distilled off. The obtained crude product was solidified from diethyl ether to give compound I-2 (63 mg, yield: 68%).

MS: m/z=474 [M+H]+

1H-NMR (CDCl$_3$) δ: 12.04 (s, 1H), 8.73 (s, 1H), 7.31 (m, 1H), 6.84 (t, J=8.6 Hz, 2H), 5.14 (s, 1H), 4.45 (s, 2H), 4.36 (m, 1H), 3.26-3.04 (m, 3H), 2.33 (d, J=14.9 Hz, 1H), 2.08 (t, J=14.7 Hz, 1H), 1.91 (m, 3H), 1.42 (m, 1H), 1.24 (t, J=7.2 Hz, 3H).

Compound 10 was also subjected to the same reaction conditions as above to give compound I-1.

MS: m/z=474 [M+H]+

Example 2

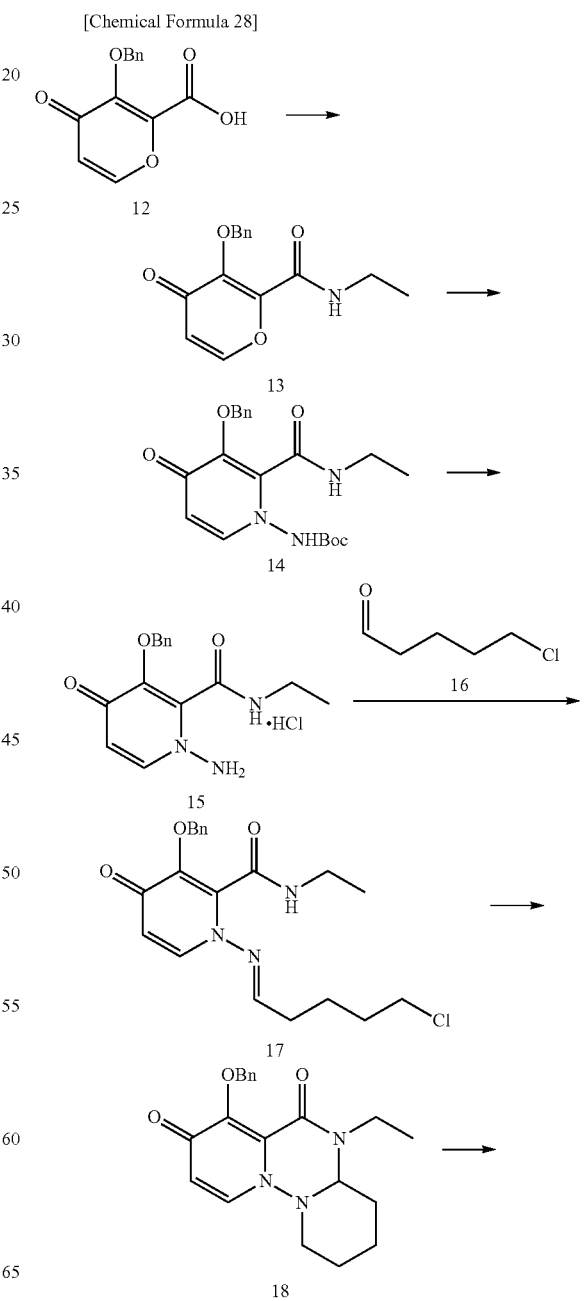

[Chemical Formula 28]

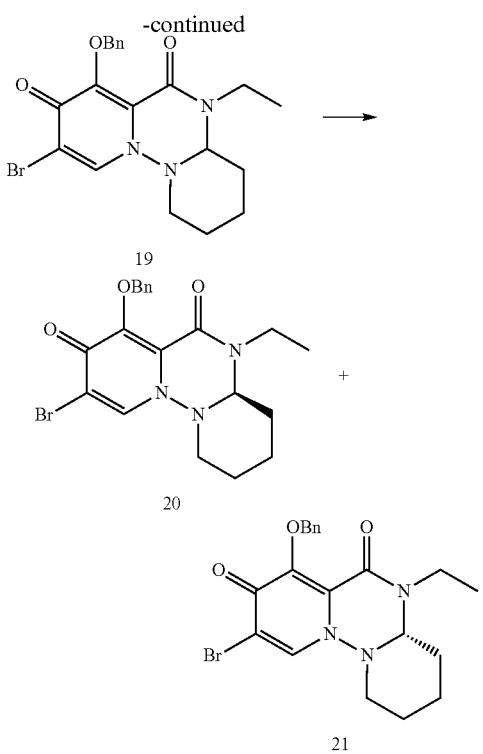

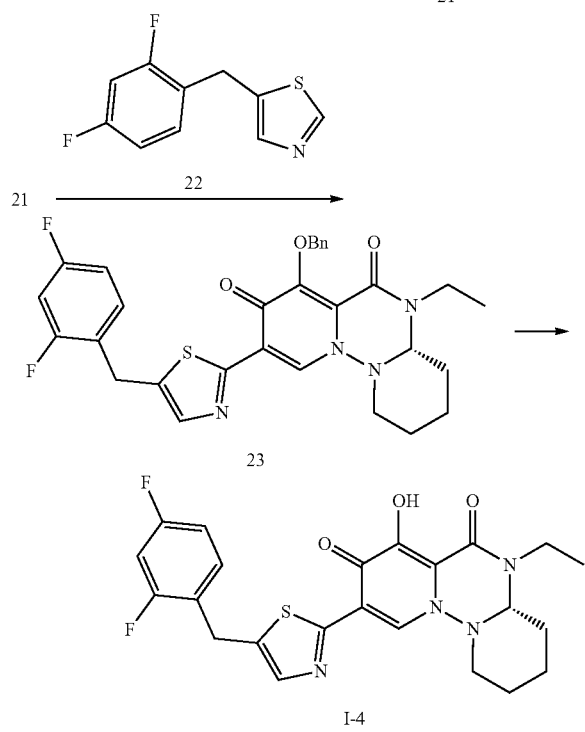

The obtained solid was suspended in isopropyl ether and collected by filtration to give compound 13 (10.7 g, yield: 80%).

1H-NMR (CDCl$_3$) δ: 7.84 (d, J=5.8 Hz, 1H), 7.69 (s, 1H), 7.41-7.39 (m, 5H), 6.49 (d, J=5.5 Hz, 1H), 5.41 (s, 2H), 3.29-3.26 (m, 2H), 0.97 (t, J=7.3 Hz, 3H).

Step 2

Compound 13 (10 g, 36.6 mmol) was dissolved in DMA (100 mL). To the solution, pyridinium p-toluenesulfonate (27.6 g, 109.8 mmol) was added, and the mixture was then heated to 60° C. t-Bu carbazate (8.7 g, 65.9 mmol) was added in 6 divided portions at 1-hour intervals to the reaction solution. The reaction solution was allowed to cool to room temperature, then rendered basic by the addition of a 1 mol/L aqueous sodium hydroxide solution, and washed with diethyl ether. The aqueous layer was rendered acidic by the addition of 2 mol/L hydrochloric acid, followed by extraction with ethyl acetate. The organic layer was washed with brine and dried over anhydrous sodium sulfate, and the solvent was then distilled off under reduced pressure. The obtained solid was washed with ethyl acetate/diisopropyl ether to give compound 14 (6.3 g, yield: 44%).

1H-NMR (CDCl$_3$) δ: 8.31 (br s, 1H), 7.36-7.34 (m, 6H), 6.59 (s, 1H), 6.40 (d, J=8.0 Hz, 1H), 5.32 (s, 2H), 3.21-3.17 (m, 2H), 1.43 (s, 9H), 0.99 (t, J=7.3 Hz, 3H).

Step 3

Compound 14 (0.5 g, 1.3 mmol) was dissolved in a 4 mol/L solution of hydrogen chloride in ethyl acetate (5 mL), and the solution was stirred at room temperature for 30 minutes. The solvent was evaporated under reduced pressure to give the crude product of the compound 15.

MS: m/z=288 [M+H]+

Step 4 The crude product (0.13 g) of compound 15 was dissolved in dichloromethane (1 mL). To the solution, compound 16 (46.2 mg, 0.38 mmol) was added, and the mixture was stirred at room temperature for 1 hour. The solvent in the reaction solution was distilled off under reduced pressure. The obtained residue was purified by silica gel column chromatography (chloroform-methanol) to give compound 17 (0.13 g, yield: 96%).

MS: m/z=390 [M+H]+

Step 5

Compound 17 (0.13 g, 33.3 mmol) was dissolved in DMF (1.0 mL). To the solution, cesium carbonate (0.34 g, 1.0 mmol) and sodium iodide (0.16 g, 1.0 mmol) were added, and the mixture was stirred overnight at 50° C. Ethyl acetate was added to the reaction solution. The resulting solid was filtered off, and the solvent was distilled off under reduced pressure. The obtained partially purified product was purified by silica gel column chromatography (chloroform-methanol) to give compound 18 (52 mg, yield: 44%).

1H-NMR (CDCl$_3$) δ: 7.60 (d, J=7.0 Hz, 2H), 7.32-7.28 (m, 4H), 6.40 (d, J=7.5 Hz, 1H), 5.48 (d, J=10.5 Hz, 1H), 5.27 (d, J=10.5 Hz, 1H), 4.88-4.90 (m, 1H), 4.43-4.39 (m, 1H), 3.12-2.97 (m, 3H), 2.24-2.20 (m, 1H), 1.98-1.91 (m, 1H), 1.83-1.80 (m, 2H), 1.71-1.67 (m, 1H), 1.40-1.38 (m, 1H), 1.14 (t, J=7.0 Hz, 3H).

Step 6

A solution of compound 18 (1.0 g, 2.8 mmol) in dichloromethane (10 mL) was cooled to 0° C. NBS (0.56 g, 3.1 mmol) was added thereto, and the mixture was stirred overnight at room temperature. The solvent in the reaction solution was distilled off under reduced pressure. The obtained residue was purified by silica gel column chromatography (chloroform-methanol) to give compound 19 (1.4 g, yield: 93%).

Step 1

A solution of compound 12 (12 g, 48.7 mmol) in DMF (60 mL) was cooled to 0° C. HOBt (7.9 g, 58.5 mmol), EDC (11.2 g, 58.5 mmol), triethylamine (8.1 mL, 58.5 mmol) and ethylamine hydrochloride (4.8 g, 58.5 mmol) were added thereto, and the mixture was stirred at room temperature for 1 hour. Water was added to the reaction solution, followed by extraction with ethyl acetate. The organic layer was washed with brine and dried over anhydrous sodium sulfate, and the solvent was then distilled off under reduced pressure.

1H-NMR (CDCl₃) δ: 7.83 (s, 1H), 7.64 (d, J=7.0 Hz, 2H), 7.34-7.27 (m, 3H), 5.48 (d, J=10.3 Hz, 1H), 5.26 (d, J=10.3 Hz, 1H), 4.92-4.90 (m, 1H), 4.43-4.39 (m, 1H), 3.20-3.14 (m, 1H), 3.05-2.98 (m, 2H), 2.26-2.22 (m, 1H), 1.97-1.94 (m, 1H), 1.84-1.82 (m, 2H), 1.73-1.69 (m, 1H), 1.41-1.39 (m, 1H), 1.16 (t, J=7.2 Hz, 3H).

Step 7

Compound 19 was optically resolved by SFC to give compounds 20 and 21.

Column: CHIRALPAK IB/SFC (5 μm, i.d. 250×20 mm)

Flow rate: 30 mL/min

UV detection wavelength: 220 nm

Fractionation conditions: a compositional ratio of MeOH/CO2=35/65 was kept, and the solution was sent for 21 minutes.

Step 8

Compound 21 (250 mg, 0.58 mmol) was dissolved in toluene. To the solution, compound 22 (183 mg, 0.87 mmol), Pd(OAc)₂ (13.0 mg, 0.06 mmol), 2-dicyclohexylphosphino-2'-(N,N-diamino)biphenyl (46 mg, 0.12 mmol) and cesium carbonate (565 mg, 1.7 mmol) were added, and after sealing, the mixture was stirred at 140° C. for 2 hours. The reaction mixture was allowed to cool to room temperature, and the insoluble material was removed by filtration through celite. The solvent was distilled off under reduced pressure. The obtained residue was partially purified by silica gel column chromatography (hexane-ethyl acetate) and purified in a reverse phase to give compound 23 (40 mg, yield: 12%).

1H-NMR (CDCl₃) δ: 8.63 (s, 1H), 7.64-7.61 (m, 3H), 7.34-7.19 (m, 4H), 6.83-6.79 (m, 2H), 5.58 (d, J=10.3 Hz, 1H), 5.33 (d, J=10.3 Hz, 1H), 4.96-4.94 (m, 1H), 4.44-4.40 (m, 1H), 4.19 (s, 2H), 3.22-3.18 (m, 1H), 3.09-3.02 (m, 2H), 2.27-2.23 (m, 1H), 2.01-1.97 (m, 1H), 1.86-1.84 (m, 2H), 1.74-1.70 (m, 1H), 1.43-1.40 (m, 1H), 1.17 (t, J=7.0 Hz, 3H).

Step 9

Compound 23 (40 mg, 0.071 mmol) was subjected to the same reaction conditions as in step 9 of Example 1 to give compound I-4 (22 mg, yield: 67%).

1H-NMR (CDCl₃) δ: 11.81 (br s, 1H), 8.59 (s, 1H), 7.54 (s, 1H), 7.20-7.18 (m, 1H), 6.83-6.78 (m, 2H), 5.11-5.09 (m, 1H), 4.40-4.31 (m, 1H), 4.18 (s, 2H), 3.24-3.02 (m, 3H), 2.34-2.29 (m, 1H), 2.09-2.01 (m, 1H), 1.90-1.85 (m, 2H), 1.78-1.74 (m, 1H), 1.46-1.36 (m, 1H), 1.23 (t, J=7.0 Hz, 3H).

Example 3

[Chemical Formula 29]

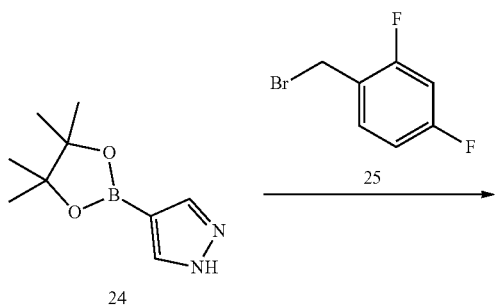

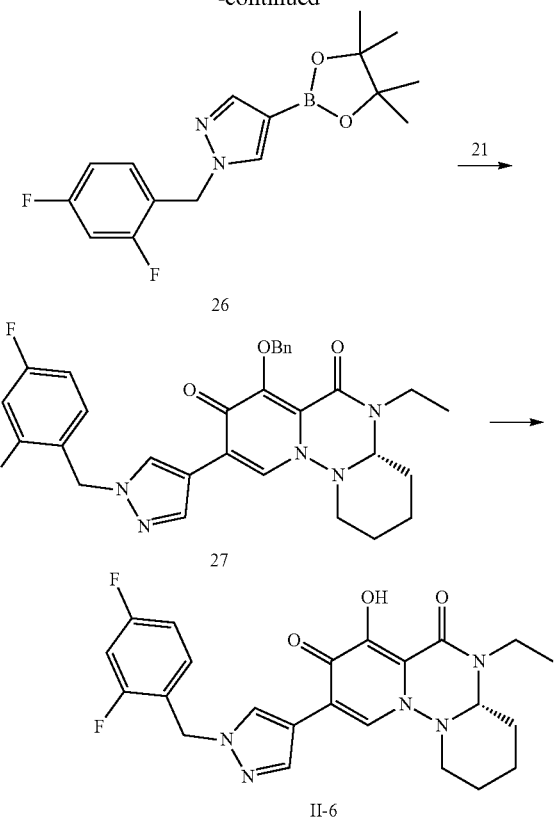

Step 1

To a solution of compound 24 (528 mg, 2.10 mmol) in THF (5.0 mL), sodium hydride (60 wt %, 135 mg, 3.38 mmol) was added at 0° C., and the mixture was stirred at 0° C. for 10 minutes. Compound 25 (500 mg, 2.415 mmol) was added to the reaction solution, and the mixture was raised to room temperature and reacted overnight. Water was added to the reaction solution, followed by extraction with ethyl acetate. The organic layer was washed with brine and dried over anhydrous sodium sulfate, and the solvent was then distilled off. The obtained residue was purified by silica gel column chromatography (hexane-ethyl acetate) to give compound 26 (517 mg, yield: 67%).

MS: m/z=321 [M+H]+

Step 2

Compound 26 (89 mg, 0.278 mmol), compound 21 (60 mg, 0.139 mmol), cesium carbonate (68 mg, 0.208 mmol), and tetrakistriphenylphosphinepalladium (16 mg, 0.014 mmol) were dissolved in dioxane (1.8 mL), and the mixture was reacted at 90° C. for 7 hours. Water was added to the reaction solution, followed by extraction with ethyl acetate. The organic layer was washed with brine and dried over anhydrous sodium sulfate, and the solvent was then distilled off. The obtained residue was partially purified by silica gel column chromatography (ethyl acetate-methanol).

MS: m/z=546 [M+H]+

Step 3

A compound II-6 was obtained by the similar method of Step 9 of Example 1. 1H-NMR (CDCl₃) δ: 8.66 (s, 1H), 7.77 (s, 1H), 7.72 (s, 1H), 7.20-7.15 (m, 1H), 6.86-6.80 (m, 2H), 5.35 (s, 2H), 5.08 (s, 1H), 4.40-4.30 (m, 1H), 3.20-2.95 (m, 3H), 2.35-2.25 (m, 1H), 2.01-1.40 (m, 6H), 1.22 (t, J=7.2 Hz, 3H).

The following compounds were also synthesized in the same way as above.
TABLE 1
| No. | Structure |
|---|---|
| I-003 | 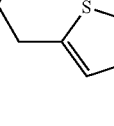 |
| I-005 | 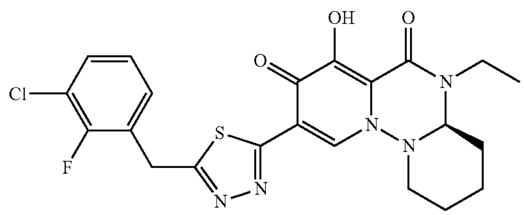 [SMILES: CCN1C(=O)c2c(O)c(=O)c(-c3nnc(Cc4cccc(Cl)c4F)s3)cn2N2CCCC[C@H]12] |
| I-006 | 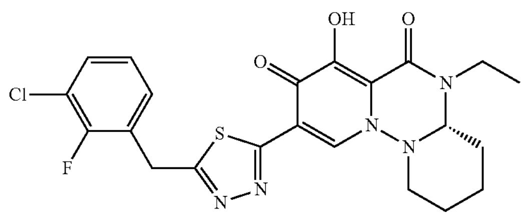 [SMILES: CCN1C(=O)c2c(O)c(=O)c(-c3nnc(Cc4cccc(Cl)c4F)s3)cn2N2CCCC[C@@H]12] |
| I-007 | 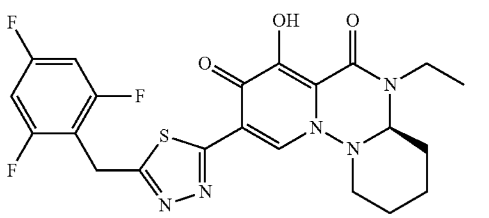 |
| I-008 | 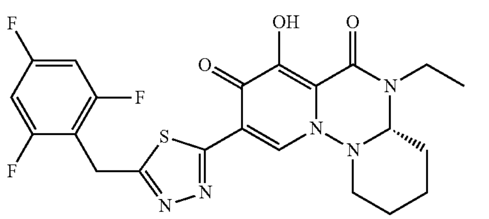 [SMILES: CCN1C(=O)c2c(O)c(=O)c(-c3nnc(Cc4c(F)cc(F)cc4F)s3)cn2N2CCCC[C@@H]12] |
| I-009 | 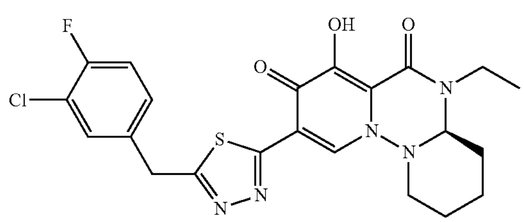 [SMILES: CCN1C(=O)c2c(O)c(=O)c(-c3nnc(Cc4ccc(F)c(Cl)c4)s3)cn2N2CCCC[C@H]12] |
| I-010 | 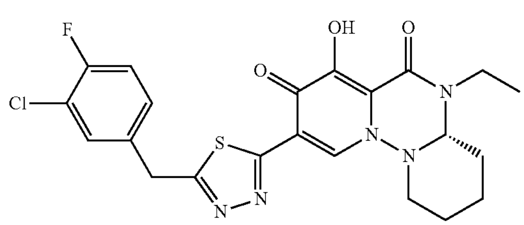 [SMILES: CCN1C(=O)c2c(O)c(=O)c(-c3nnc(Cc4ccc(F)c(Cl)c4)s3)cn2N2CCCC[C@@H]12] |
TABLE 1-continued
| No. | Structure |
|---|---|
| I-011 | 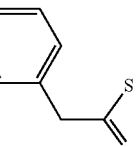 |
| I-012 | 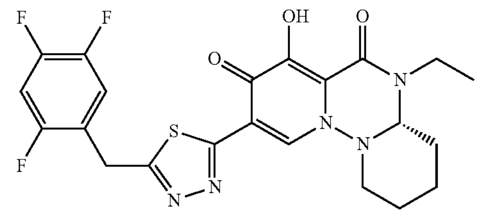 [SMILES: CCN1C(=O)c2c(O)c(=O)c(-c3nnc(Cc4cc(F)c(F)cc4F)s3)cn2N2CCCC[C@@H]12] |
| I-013 | 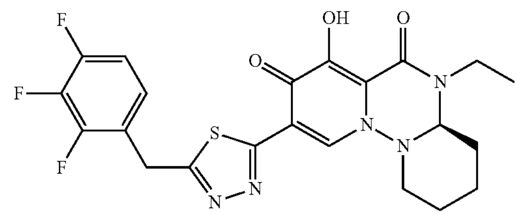 [SMILES: CCN1C(=O)c2c(O)c(=O)c(-c3nnc(Cc4ccc(F)c(F)c4F)s3)cn2N2CCCC[C@H]12] |
| I-014 | 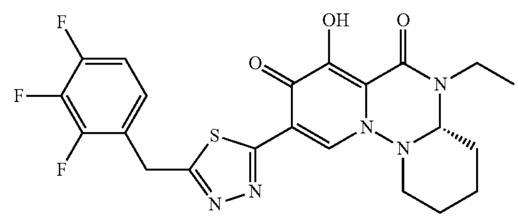 [SMILES: CCN1C(=O)c2c(O)c(=O)c(-c3nnc(Cc4ccc(F)c(F)c4F)s3)cn2N2CCCC[C@@H]12] |
| II-001 | 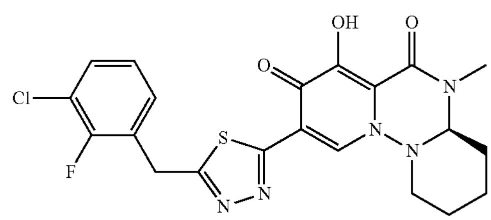 [SMILES: CN1C(=O)c2c(O)c(=O)c(-c3nnc(Cc4cccc(Cl)c4F)s3)cn2N2CCCC[C@H]12] |
| II-002 | 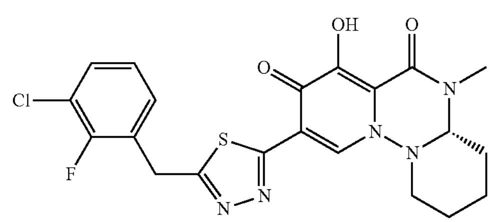 [SMILES: CN1C(=O)c2c(O)c(=O)c(-c3nnc(Cc4cccc(Cl)c4F)s3)cn2N2CCCC[C@@H]12] |
| II-003 | 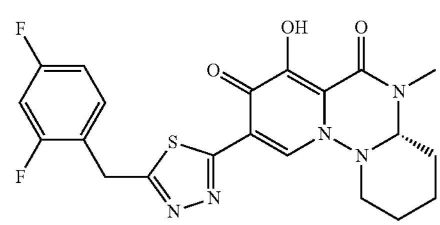 [SMILES: CN1C(=O)c2c(O)c(=O)c(-c3nnc(Cc4ccc(F)cc4F)s3)cn2N2CCCC[C@@H]12] |

TABLE 1-continued

| No. | Structure |
| --- | --- |
| II-004 | 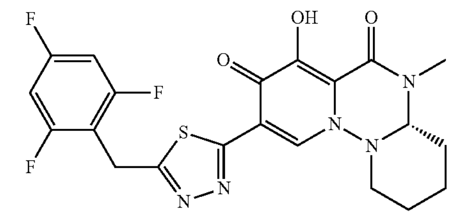 [SMILES: CN1C(=O)c2c(O)c(=O)c(-c3nnc(Cc4c(F)cc(F)cc4F)s3)cn2N2CCCC[C@@H]12] |
| II-005 | 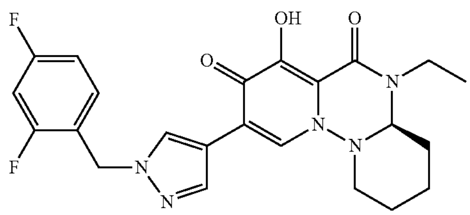 [SMILES: CCN1C(=O)c2c(O)c(=O)c(-c3cnn(Cc4ccc(F)cc4F)c3)cn2N2CCCC[C@H]12] |
| II-007 | 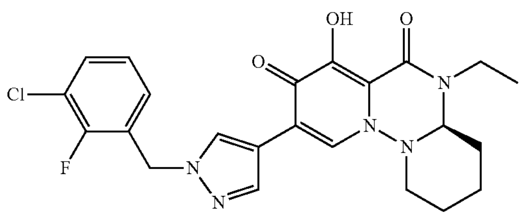 [SMILES: CCN1C(=O)c2c(O)c(=O)c(-c3cnn(Cc4cccc(Cl)c4F)c3)cn2N2CCCC[C@H]12] |
| II-008 | 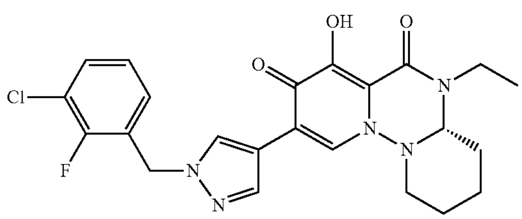 [SMILES: CCN1C(=O)c2c(O)c(=O)c(-c3cnn(Cc4cccc(Cl)c4F)c3)cn2N2CCCC[C@@H]12] |

TABLE 2

| No. | Structure |
| --- | --- |
| II-009 | 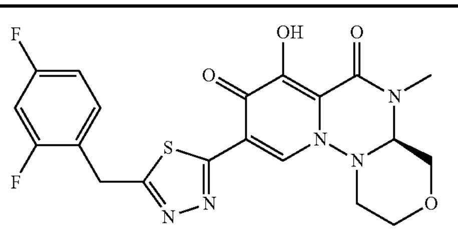 |
| II-010 | 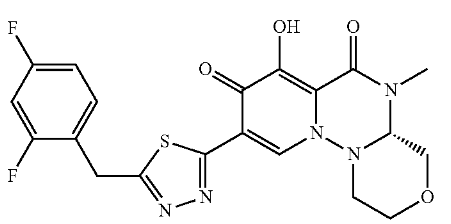 [SMILES: CN1C(=O)c2c(O)c(=O)c(-c3nnc(Cc4ccc(F)cc4F)s3)cn2N2CCOC[C@@H]12] |

TABLE 2-continued

| No. | Structure |
| --- | --- |
| II-011 | 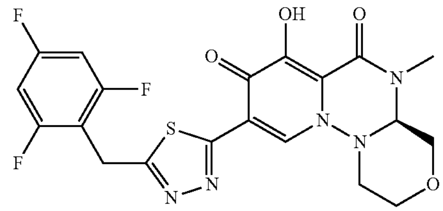 [SMILES: CN1C(=O)c2c(O)c(=O)c(-c3nnc(Cc4c(F)cc(F)cc4F)s3)cn2N2CCOC[C@H]12] |
| II-012 | 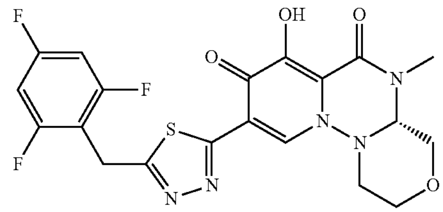 [SMILES: CN1C(=O)c2c(O)c(=O)c(-c3nnc(Cc4c(F)cc(F)cc4F)s3)cn2N2CCOC[C@@H]12] |
| II-013 | 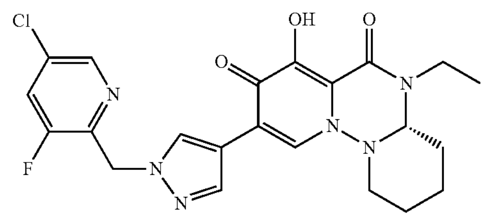 [SMILES: CCN1C(=O)c2c(O)c(=O)c(-c3cnn(Cc4ncc(Cl)cc4F)c3)cn2N2CCCC[C@@H]12] |
| II-014 | 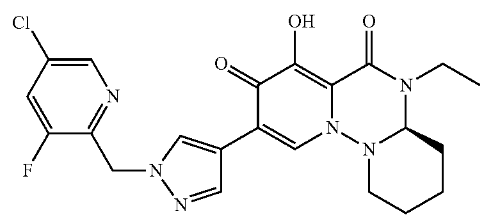 [SMILES: CCN1C(=O)c2c(O)c(=O)c(-c3cnn(Cc4ncc(Cl)cc4F)c3)cn2N2CCCC[C@H]12] |
| II-015 | 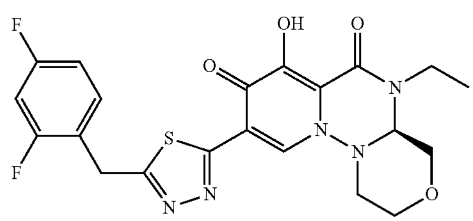 [SMILES: CCN1C(=O)c2c(O)c(=O)c(-c3nnc(Cc4ccc(F)cc4F)s3)cn2N2CCOC[C@H]12] |
| II-016 | 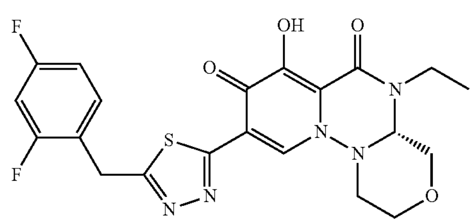 [SMILES: CCN1C(=O)c2c(O)c(=O)c(-c3nnc(Cc4ccc(F)cc4F)s3)cn2N2CCOC[C@@H]12] |
| II-017 | 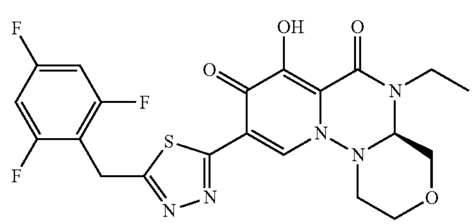 |

TABLE 2-continued

| No. | Structure |
|---|---|
| II-018 | 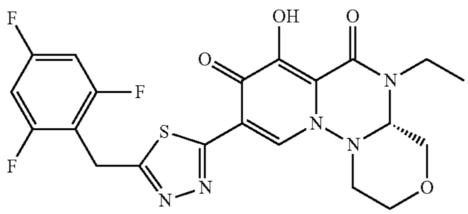 [SMILES: CCN1C(=O)c2c(O)c(=O)c(-c3nnc(Cc4c(F)cc(F)cc4F)s3)cn2N2CCOC[C@@H]12] |
| II-019 | 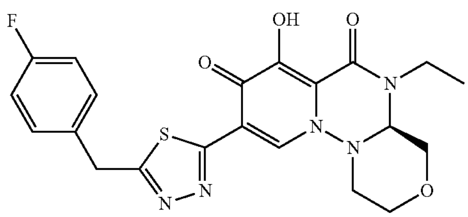 |
| II-020 | 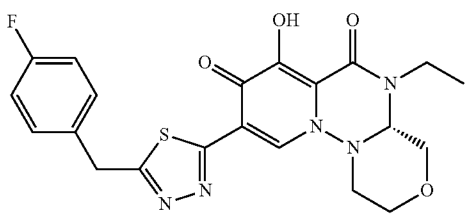 [SMILES: CCN1C(=O)c2c(O)c(=O)c(-c3nnc(Cc4ccc(F)cc4)s3)cn2N2CCOC[C@@H]12] |
| II-021 | 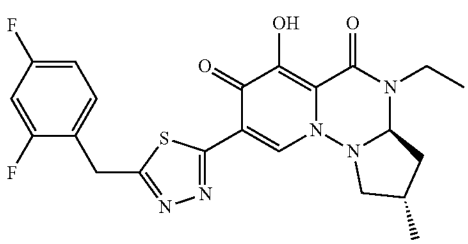 [SMILES: CCN1C(=O)c2c(O)c(=O)c(-c3nnc(Cc4ccc(F)cc4F)s3)cn2N2C[C@@H](C)C[C@H]12] |
| II-022 | 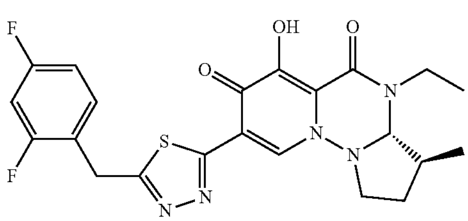 [SMILES: CCN1C(=O)c2c(O)c(=O)c(-c3nnc(Cc4ccc(F)cc4F)s3)cn2N2CC[C@H](C)[C@@H]12] |
| II-023 | 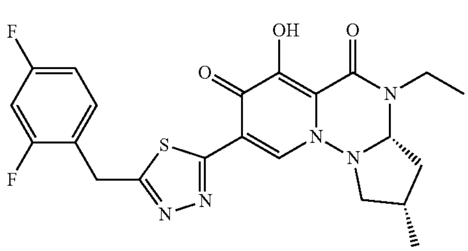 [SMILES: CCN1C(=O)c2c(O)c(=O)c(-c3nnc(Cc4ccc(F)cc4F)s3)cn2N2C[C@@H](C)C[C@@H]12] |

TABLE 2-continued

| No. | Structure |
|---|---|
| II-024 | |

TABLE 3

| No. | Structure |
|---|---|
| II-025 | 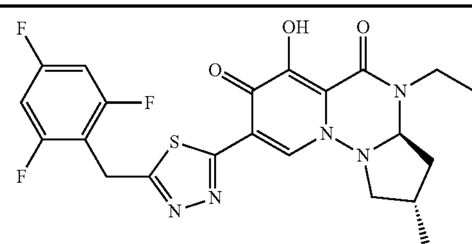 |
| II-026 | 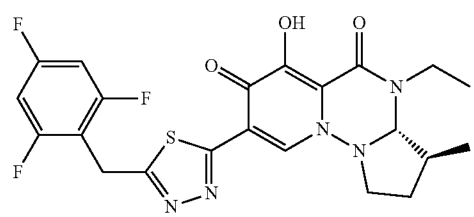 [SMILES: CCN1C(=O)c2c(O)c(=O)c(-c3nnc(Cc4c(F)cc(F)cc4F)s3)cn2N2CC[C@H](C)[C@@H]12] |
| II-027 | 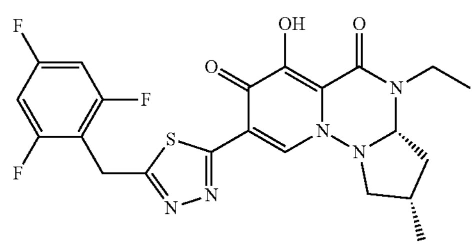 [SMILES: CCN1C(=O)c2c(O)c(=O)c(-c3nnc(Cc4c(F)cc(F)cc4F)s3)cn2N2C[C@@H](C)C[C@@H]12] |
| II-028 | 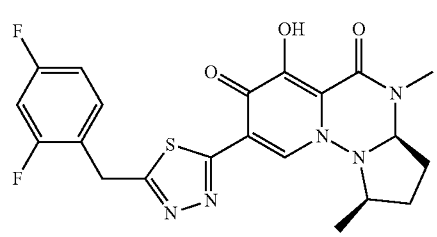 [SMILES: C[C@@H]1CC[C@@H]2N(C)C(=O)c3c(O)c(=O)c(-c4nnc(Cc5ccc(F)cc5F)s4)cn3N12] |
| II-029 | 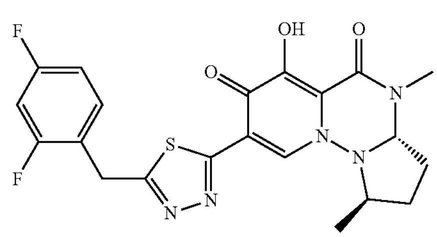 [SMILES: C[C@@H]1CC[C@H]2N(C)C(=O)c3c(O)c(=O)c(-c4nnc(Cc5ccc(F)cc5F)s4)cn3N12] |

TABLE 3-continued

| No. | Structure |
|---|---|
| II-030 | 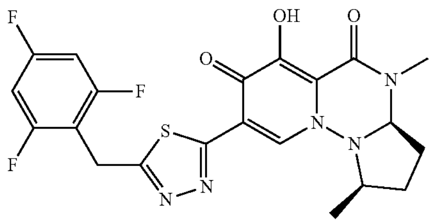 [SMILES: C[C@@H]1CC[C@@H]2N(C)C(=O)c3c(O)c(=O)c(-c4nnc(Cc5c(F)cc(F)cc5F)s4)cn3N12] |
| II-031 | 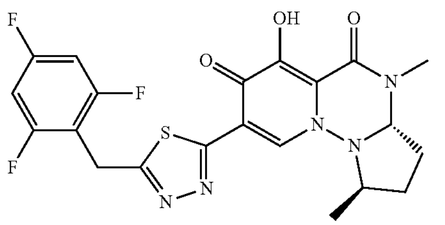 [SMILES: C[C@@H]1CC[C@H]2N(C)C(=O)c3c(O)c(=O)c(-c4nnc(Cc5c(F)cc(F)cc5F)s4)cn3N12] |
| II-032 | 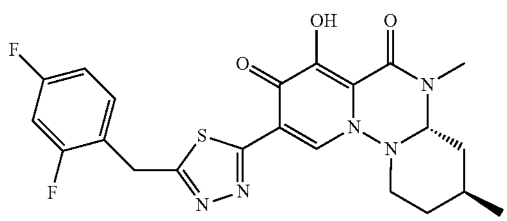 [SMILES: C[C@H]1CCN2[C@@H](C1)N(C)C(=O)c1c(O)c(=O)c(-c3nnc(Cc4ccc(F)cc4F)s3)cn12] |
| II-033 | 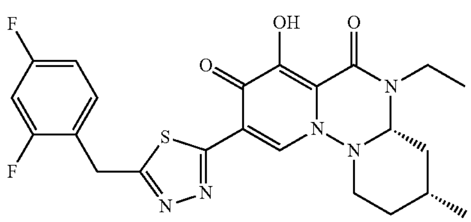 [SMILES: CCN1C(=O)c2c(O)c(=O)c(-c3nnc(Cc4ccc(F)cc4F)s3)cn2N2CC[C@@H](C)C[C@@H]12] |
| II-034 | 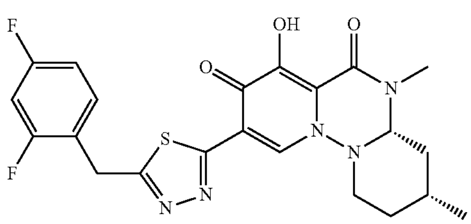 [SMILES: C[C@@H]1CCN2[C@@H](C1)N(C)C(=O)c1c(O)c(=O)c(-c3nnc(Cc4ccc(F)cc4F)s3)cn12] |
| II-035 | 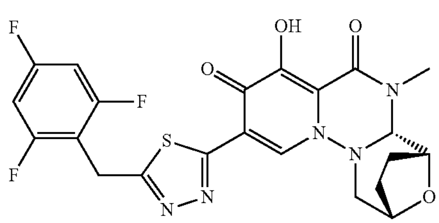 [SMILES: CN1C(=O)c2c(O)c(=O)c(-c3nnc(Cc4c(F)cc(F)cc4F)s3)cn2N2C[C@@H]3CC[C@@H](O3)[C@@H]12] |
| II-036 | 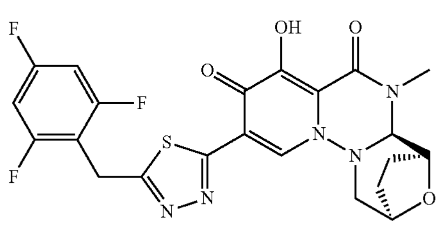 [SMILES: CN1C(=O)c2c(O)c(=O)c(-c3nnc(Cc4c(F)cc(F)cc4F)s3)cn2N2C[C@H]3CC[C@H](O3)[C@H]12] |

TABLE 3-continued

| No. | Structure |
|---|---|
| II-037 | |
| II-038 | |
| II-039 | |
| II-040 | |

TABLE 4

| No. | Structure |
|---|---|
| II-041 | 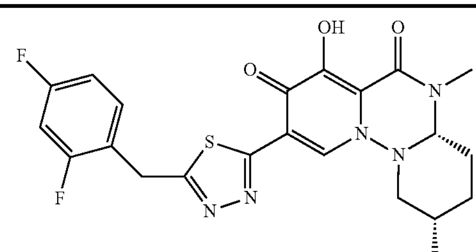 |
| II-042 | 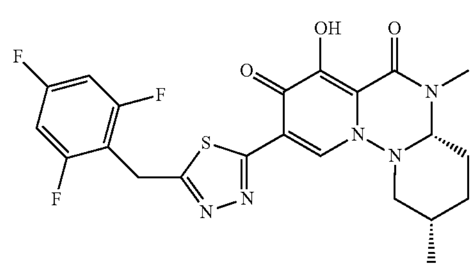 [SMILES: C[C@H]1CC[C@H]2N(C)C(=O)c3c(O)c(=O)c(-c4nnc(Cc5c(F)cc(F)cc5F)s4)cn3N2C1] |

TABLE 4-continued

| No. | Structure |
|---|---|
| II-043 | 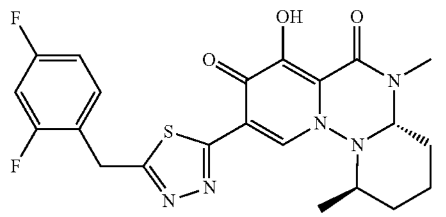 [SMILES: C[C@@H]1CCC[C@H]2N(C)C(=O)c3c(O)c(=O)c(-c4nnc(Cc5ccc(F)cc5F)s4)cn3N12] |
| II-044 | 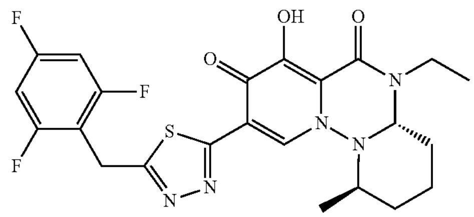 [SMILES: CCN1C(=O)c2c(O)c(=O)c(-c3nnc(Cc4c(F)cc(F)cc4F)s3)cn2N2[C@H](C)CCC[C@@H]12] |
| II-045 | 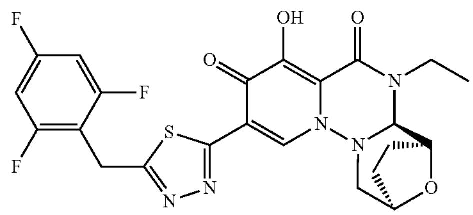 [SMILES: CCN1C(=O)c2c(O)c(=O)c(-c3nnc(Cc4c(F)cc(F)cc4F)s3)cn2N2C[C@H]3CC[C@H](O3)[C@H]12] |
| II-046 | 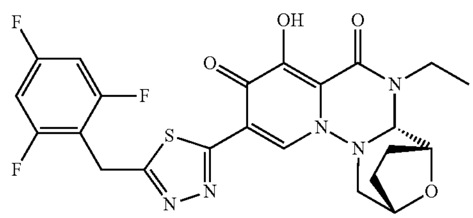 [SMILES: CCN1C(=O)c2c(O)c(=O)c(-c3nnc(Cc4c(F)cc(F)cc4F)s3)cn2N2C[C@@H]3CC[C@@H](O3)[C@@H]12] |
| II-047 | 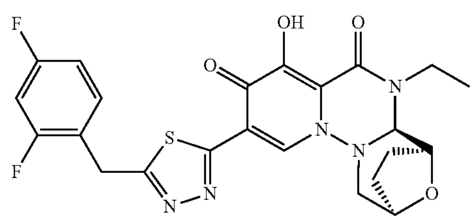 [SMILES: CCN1C(=O)c2c(O)c(=O)c(-c3nnc(Cc4ccc(F)cc4F)s3)cn2N2C[C@H]3CC[C@H](O3)[C@H]12] |
| II-048 | 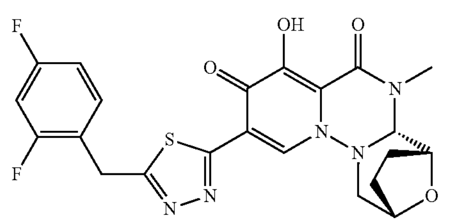 [SMILES: CN1C(=O)c2c(O)c(=O)c(-c3nnc(Cc4ccc(F)cc4F)s3)cn2N2C[C@@H]3CC[C@@H](O3)[C@@H]12] |
| II-049 | 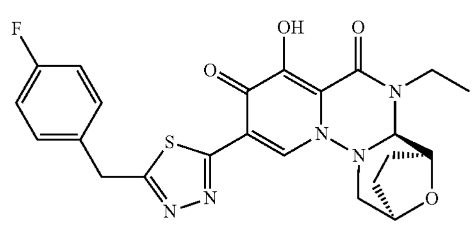 [SMILES: CCN1C(=O)c2c(O)c(=O)c(-c3nnc(Cc4ccc(F)cc4)s3)cn2N2C[C@H]3CC[C@H](O3)[C@H]12] |
| II-050 | |
| II-051 | |
| II-052 | |
| II-053 | |
| II-054 | |
| II-055 | |
| II-056 | |

TABLE 5

| No. | Structure |
|---|---|
| II-057 | 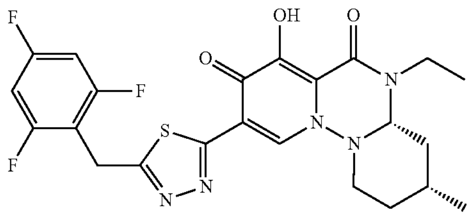 [SMILES: CCN1C(=O)c2c(O)c(=O)c(-c3nnc(Cc4c(F)cc(F)cc4F)s3)cn2N2CC[C@@H](C)C[C@@H]12] |
| II-058 | 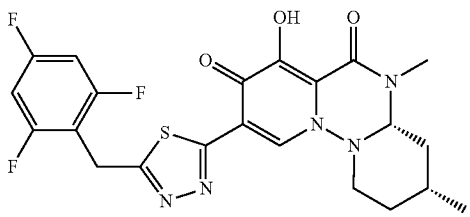 [SMILES: C[C@@H]1CCN2[C@@H](C1)N(C)C(=O)c1c(O)c(=O)c(-c3nnc(Cc4c(F)cc(F)cc4F)s3)cn12] |
| II-059 | 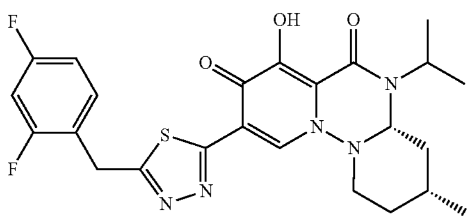 [SMILES: CC(C)N1C(=O)c2c(O)c(=O)c(-c3nnc(Cc4ccc(F)cc4F)s3)cn2N2CC[C@@H](C)C[C@@H]12] |
| II-060 | 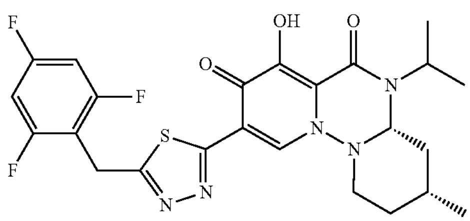 [SMILES: CC(C)N1C(=O)c2c(O)c(=O)c(-c3nnc(Cc4c(F)cc(F)cc4F)s3)cn2N2CC[C@@H](C)C[C@@H]12] |
| II-061 | 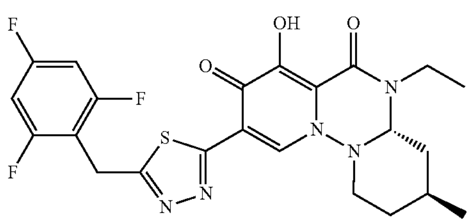 [SMILES: CCN1C(=O)c2c(O)c(=O)c(-c3nnc(Cc4c(F)cc(F)cc4F)s3)cn2N2CC[C@H](C)C[C@@H]12] |
| II-062 | 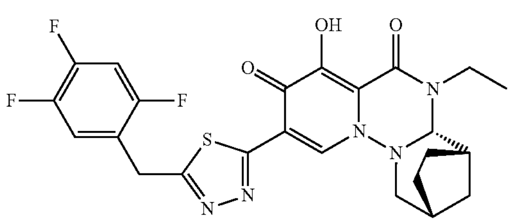 [SMILES: CCN1C(=O)c2c(O)c(=O)c(-c3nnc(Cc4cc(F)c(F)cc4F)s3)cn2N2C[C@@H]3CC[C@@H](C3)[C@@H]12] |
| II-063 | 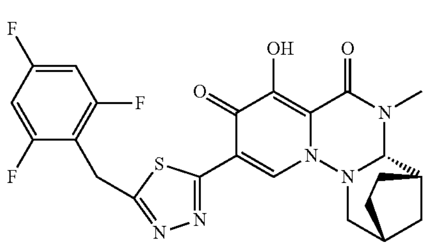 [SMILES: CN1C(=O)c2c(O)c(=O)c(-c3nnc(Cc4c(F)cc(F)cc4F)s3)cn2N2C[C@@H]3CC[C@@H](C3)[C@@H]12] |

TABLE 5-continued

| No. | Structure |
|---|---|
| II-064 | 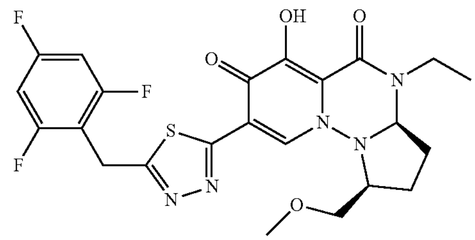 [SMILES: CCN1C(=O)c2c(O)c(=O)c(-c3nnc(Cc4c(F)cc(F)cc4F)s3)cn2N2[C@H](COC)CC[C@H]12] |
| II-065 | 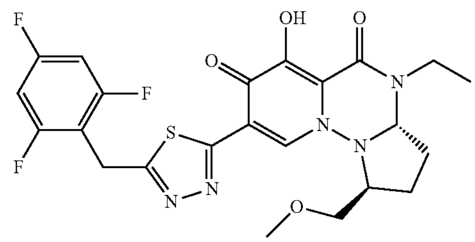 [SMILES: CCN1C(=O)c2c(O)c(=O)c(-c3nnc(Cc4c(F)cc(F)cc4F)s3)cn2N2[C@H](COC)CC[C@@H]12] |
| II-066 | 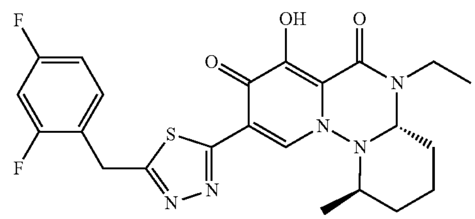 [SMILES: CCN1C(=O)c2c(O)c(=O)c(-c3nnc(Cc4ccc(F)cc4F)s3)cn2N2[C@H](C)CCC[C@@H]12] |
| II-067 | 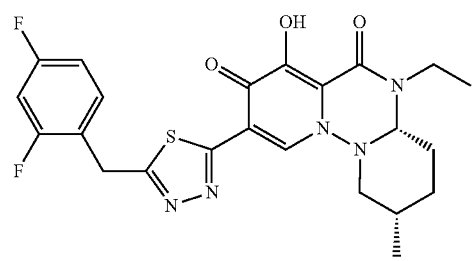 [SMILES: CCN1C(=O)c2c(O)c(=O)c(-c3nnc(Cc4ccc(F)cc4F)s3)cn2N2C[C@@H](C)CC[C@@H]12] |
| II-068 | 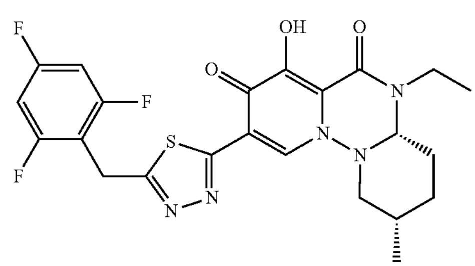 [SMILES: CCN1C(=O)c2c(O)c(=O)c(-c3nnc(Cc4c(F)cc(F)cc4F)s3)cn2N2C[C@@H](C)CC[C@@H]12] |
| II-069 | 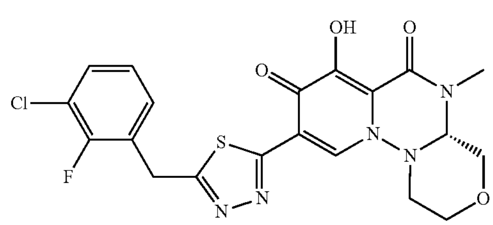 [SMILES: CN1C(=O)c2c(O)c(=O)c(-c3nnc(Cc4cccc(Cl)c4F)s3)cn2N2CCOC[C@@H]12] |

Physical data on each compound will be shown below.

TABLE 6

| No. | MS | Charge |
|---|---|---|
| I-001 | 474 | M + H |
| I-002 | 474 | M + H |
| I-003 | 473 | M + H |
| I-004 | 473 | M + H |
| I-005 | 490 | M + H |
| I-006 | 490 | M + H |
| I-007 | 492 | M + H |
| I-008 | 492 | M + H |
| I-009 | 490 | M + H |
| I-010 | 490 | M + H |
| I-011 | 492 | M + H |
| I-012 | 492 | M + H |
| I-013 | 492 | M + H |
| I-014 | 492 | M + H |
| II-001 | 476 | M + H |
| II-002 | 476 | M + H |
| II-003 | 460 | M + H |
| II-004 | 478 | M + H |
| II-005 | 456 | M + H |
| II-006 | 456 | M + H |
| II-007 | 472 | M + H |
| II-008 | 472 | M + H |
| II-009 | 462 | M + H |
| II-010 | 462 | M + H |
| II-011 | 480 | M + H |
| II-012 | 480 | M + H |
| II-013 | 473 | M + H |
| II-014 | 473 | M + H |
| II-015 | 476 | M + H |
| II-016 | 476 | M + H |
| II-017 | 494 | M + H |
| II-018 | 494 | M + H |
| II-019 | 458 | M + H |
| II-020 | 458 | M + H |
| II-021 | 474 | M + H |
| II-022 | 474 | M + H |
| II-023 | 474 | M + H |
| II-024 | 504 | M + H |
| II-025 | 492 | M + H |
| II-026 | 492 | M + H |
| II-027 | 492 | M + H |
| II-028 | 460 | M + H |
| II-029 | 460 | M + H |
| II-030 | 478 | M + H |
| II-031 | 478 | M + H |
| II-032 | 474 | M + H |
| II-033 | 531 | M + H |
| II-034 | 474 | M + H |
| II-035 | 506 | M + H |
| II-036 | 506 | M + H |
| II-037 | 522 | M + H |
| II-038 | 486 | M + H |
| II-039 | 494 | M + H |
| II-040 | 494 | M + H |
| II-041 | 474 | M + H |
| II-042 | 492 | M + H |
| II-043 | 474 | M + H |
| II-044 | 506 | M + H |
| II-045 | 520 | M + H |
| II-046 | 520 | M + H |
| II-047 | 502 | M + H |
| II-048 | 502 | M + H |
| II-049 | 484 | M + H |
| II-050 | 484 | M + H |
| II-051 | 500 | M + H |
| II-052 | 518 | M + H |
| II-053 | 534 | M + H |
| II-054 | 534 | M + H |
| II-055 | 486 | M + H |
| II-056 | 489 | M + H |
| II-057 | 506 | M + H |
| II-058 | 492 | M + H |
| II-059 | 502 | M + H |
| II-060 | 520 | M + H |
| II-061 | 506 | M + H |
| II-062 | 518 | M + H |
| II-063 | 504 | M + H |
| II-064 | 508 | M + H |
| II-065 | 508 | M + H |
| II-066 | 488 | M + H |
| II-067 | 488 | M + H |
| II-068 | 506 | M + H |
| II-069 | 478 | M + H |

Biological test examples for compounds of the present invention were described below.

The compound of the present invention may be any compound that significantly inhibits virus integrase.

Specifically, in the evaluation methods described below, EC50 is preferably 100 nM or less, more preferably 10 nM or less, further preferably 5 nM.

Test Example 1 (Anti-HIV Activity)

Serial dilutions of a test sample were prepared in a 96-well microplate (50 μL/well). $2.5 \times 10^5$ cells/mL of an MT-4 cell suspension was dispensed at 100 μL/well to the plate containing the test sample. Then, an HIV virus solution was dispensed at 50 μL/well. The plate was mixed with a plate mixer and cultured for 4 days in a $CO_2$ incubator. An MTT (3-(4,5-dimethylthiazol-2-yl)-2,5-diphenyltetrazolium bromide) solution was dispensed at 30 μL/well. The plate was reacted for 1 hour in a $CO_2$ incubator. 150 μL of the supernatant was removed from each well so as not to take up the cells. 150 μL of a cell lysis solution was added to each well and well mixed with a plate mixer until the cells were completely lysed. The absorbance of the mixed plate was measured at two wavelengths of 560 nm and 690 nm using a microplate reader. A 50% HIV inhibitory concentration (EC50) was determined from a concentration-dependent curve using the following 4 parameter logistic curve fitting model.

$$y = A + ((B \cdot A)/(1 + (C/x)^D))$$

A=minimum rate of inhibition (negative control, 0%)
B=maximum rate of inhibition (positive control, 100%)
C=compound concentration at an inflection point
D=slope coefficient
x=compound concentration
y=rate of inhibition (%)
(Results)

TABLE 7

| No. | EC50_nM |
|---|---|
| I-001 | 3.40 |
| I-002 | 3.20 |
| I-003 | 7.10 |
| I-004 | 3.20 |
| I-005 | 3.20 |
| I-006 | 2.70 |
| I-007 | 2.20 |
| I-008 | 1.60 |
| I-009 | 7.20 |
| I-010 | 3.80 |
| I-011 | 5.00 |
| I-012 | 4.80 |
| I-013 | 3.00 |
| I-014 | 1.30 |
| II-001 | 4.30 |
| II-002 | 1.60 |
| II-003 | 0.62 |
| II-004 | 0.70 |
| II-005 | 9.70 |
| II-006 | 3.70 |

TABLE 7-continued

| No. | EC50_nM |
|---|---|
| II-007 | 14.00 |
| II-008 | 4.50 |
| II-009 | 1.30 |
| II-010 | 1.30 |
| II-011 | 0.50 |
| II-012 | 0.25 |
| II-013 | 32.00 |
| II-014 | 61.00 |
| II-015 | 1.60 |
| II-016 | 0.19 |
| II-017 | 1.10 |
| II-018 | 0.52 |
| II-019 | 2.10 |
| II-020 | 0.70 |
| II-021 | 2.60 |
| II-022 | 0.67 |
| II-023 | 1.20 |
| II-024 | 0.13 |
| II-025 | 0.90 |
| II-026 | 0.39 |
| II-027 | 1.90 |
| II-028 | 0.13 |
| II-029 | 0.66 |
| II-030 | 1.40 |
| II-031 | 0.13 |
| II-032 | 0.13 |
| II-033 | 1.70 |
| II-034 | 0.13 |
| II-035 | 0.28 |
| II-036 | 2.00 |
| II-037 | 0.62 |
| II-038 | 0.13 |
| II-039 | 3.80 |
| II-040 | 1.30 |
| II-041 | 0.25 |
| II-042 | 0.20 |
| II-043 | 3.50 |
| II-044 | 1.40 |
| II-045 | 2.00 |
| II-046 | 0.60 |
| II-047 | 1.40 |
| II-048 | 0.74 |
| II-049 | 1.60 |
| II-050 | 0.66 |
| II-051 | 0.66 |
| II-052 | 0.66 |
| II-053 | 1.30 |
| II-054 | 1.00 |
| II-055 | 0.14 |
| II-056 | 0.76 |
| II-057 | 1.70 |
| II-058 | 0.69 |
| II-059 | 1.00 |
| II-060 | 2.70 |
| II-061 | 1.80 |
| II-062 | 5.20 |
| II-063 | 0.60 |
| II-064 | 0.73 |
| II-065 | 0.37 |
| II-066 | 1.10 |
| II-067 | 0.30 |
| II-068 | 1.20 |
| II-069 | 0.24 |

The above test results revealed that the compound of the present invention has a high anti-HIV activity, and therefore is useful as an HIV drug.

Test Example 2: Resistance Evaluation Test

Serial dilutions of a test sample were prepared in a 96-well microplate (50 μL/well). 2.5×10$^5$ cells/mL of a HeLa-CD4 cell suspension was dispensed at 100 μL/well to the plate containing the test sample. Then, an HIV virus solution (wild strain and mutant strain) was dispensed at 50 μL/well. The plate was mixed with a plate mixer and cultured for 3 days in a $CO_2$ incubator. The culture supernatant in each well was removed by suction. A cell lysis buffer in a reporter assay kit was dispensed at 100 μL/well, and the plate was frozen in a freezer (−80° C.). The plate frozen in a freezer was thawed at room temperature, then mixed with a plate mixer, and centrifuged at 1,200 rpm for 5 minutes. The supernatant of each well was dispensed at 20 μL/well to a 96-well microplate (BLACK). A chemiluminescent in the reporter assay kit reagent was dispensed at 100 μL/well and reacted at room temperature for approximately 1 hour. Then, luminescence intensity was measured using MicroBeta TRILUX. A 50% HIV inhibitory concentration (EC50) was determined from a concentration-dependent curve using the following 4 parameter logistic curve fitting model.

$$y = A + ((B \cdot A)/(1+(C/x)^D))$$

A=minimum rate of inhibition (negative control, 0%)
B=maximum rate of inhibition (positive control, 100%)
C=compound concentration at an inflection point
D=slope coefficient
x=compound concentration
y=rate of inhibition (%)

The degree of resistance (fold change (FC)) of each mutant strain was calculated according to the following expression.

FC=EC50 of the mutant strain/EC50 of the wild strain (Results)

The FC for mutant strain 1 (E138K/G140S/Q148H/N155H) and the FC for mutant strain 2 (E92Q/E138T/G140S/Q148H) are shown in the table.

TABLE 8

| NO. | mutant strain 1 | mutant strain 2 |
|---|---|---|
| I-002 | 5.6 | 7.5 |
| I-008 | 3.8 | 6.9 |
| I-012 | 23 | 46 |
| II-003 | 8.8 | 12 |
| II-010 | 25 | 22 |
| II-018 | 15 | 20 |
| II-023 | 4.1 | 2.5 |
| II-024 | 8.2 | 11 |
| II-027 | 4.7 | 7 |
| II-029 | 7.2 | 6.5 |
| II-033 | 2 | 4.8 |
| II-037 | 10 | 11 |
| II-038 | 20 | 31 |
| II-041 | 5.8 | 8 |
| II-043 | 6.8 | 11 |
| II-044 | 11 | 26 |
| II-046 | 17 | 20 |
| II-048 | 7.9 | 19 |
| II-050 | 20 | 29 |
| II-051 | 2.5 | 3.9 |
| II-052 | 2.3 | 3.5 |
| II-054 | 3.5 | 8.2 |
| II-055 | 15 | 11 |
| II-056 | 5.9 | 8.8 |
| II-057 | 3 | 3.6 |
| II-058 | 6.1 | 6.1 |
| II-061 | 5.1 | 7.3 |
| II-062 | 8.3 | 6.6 |
| II-063 | 14 | 12 |
| II-065 | 27 | 17 |
| II-067 | 5.2 | 5.1 |
| II-068 | 3.5 | 4.6 |
| II-069 | 30 | 25 |

FC for mutant strain 3 (E92Q/E138K/G140S/Q148H)
Compound I-2: 7.7
FC for mutant strain 4 (T97A/E138T/G140S/Q148H)
Compound I-2: 3.2

The above test results revealed that the compound of the present invention has a high resistance barrier and is less likely to generate an HIV resistant virus.

Test Example 3: CYP Inhibition Test

The degrees at which the amounts of respective metabolites produced were inhibited by the compound of the present invention were evaluated in commercially available pooled human liver microsomes by using the O-deethylation of 7-ethoxyresorufin (CYP1A2), the methyl-hydroxylation of tolbutamide (CYP2C9), 4'-hydroxylation of mephenytoin (CYP2C19), the O-demethylation of dextromethorphan (CYP2D6), and the hydroxylation of terfenadine (CYP3A4), which are the typical substrate metabolism reactions of five human major CYP molecular species (CYP1A2, CYP2C9, CYP2C19, CYP2D6, and CYP3A4), as indexes.

The reaction conditions were as follows: substrate, 0.5 µmol/L ethoxyresorufin (CYP1A2), 100 µmol/L tolbutamide (CYP2C9), 50 µmol/L S-mephenytoin (CYP2C19), 5 µmol/L dextromethorphan (CYP2D6), 1 µmol/L terfenedine (CYP3A4); reaction time, 15 minutes; reaction temperature, 37° C.; enzyme, pooled human liver microsome 0.2 mg protein/mL; concentration of a compound of the present invention, 1, 5, 10, 20 µmol/L (four points).

Each of the five substrates, the human liver microsomes, and the compound of the present invention were added according to the recipe described above into a 50 mmol/L Hepes buffer solution in a 96-well plate, and a coenzyme NADPH was added thereto to initiate the metabolism reactions as a marker reaction. After reaction at 37° C. for 15 minutes, a methanol/acetonitrile=1/1 (v/v) solution was added to stop the reaction. After centrifugation at 3000 rpm for 15 minutes, resorufin (CYP1A2 metabolite) in the centrifugation supernatant was quantified using a fluorescence multilabel counter or LC/MS/MS, and tolbutamide hydroxide (CYP2C9 metabolite), mephenytoin 4'-hydroxide (CYP2C19 metabolite), dextrorphan (CYP2D6 metabolite), and terfenadine alcohol (CYP3A4 metabolite) in the centrifugation supernatants were quantified by LC/MS/MS.

Only a solvent DMSO used for dissolving the compound was added to the reaction solution instead of the compound of the present invention, and the mixture was used as a control (100%). Remaining activity (%) was calculated, and ICs was calculated by inverse estimation based on a logistic model using the concentrations and the rates of suppression.

Test Example 4: CYP3A4 (MDZ) MBI Test

This test as to the inhibition of CYP3A4 by the compound of the present invention is to evaluate mechanism based inhibition (MBI) ability from enhancement in inhibitory effect, caused by a metabolism reaction, of the compound of the present invention. CYP3A4 inhibition was evaluated using pooled human liver microsomes by 1-hydroxylation reaction of midazolam (MDZ) as a marker reaction.

The reaction conditions are as follows: substrate, 10 µmol/L MDZ; pre-reaction time, 0 or 30 minutes; substrate metabolic reaction time, 2 minutes; reaction temperature, 37° C.; pooled human liver microsomes, at pre-reaction 0.5 mg/mL, at reaction 0.05 pmg/mL (at 10-fold dilution); concentrations of the compound of the present invention at pre-reaction, 1, 5, 10, 20 µmol/L (four points), or 0.83, 5, 10, 20 µmol/L (four points).

Pooled human liver microsomes and a solution of the compound of the present invention in K-Pi buffer solution (pH 7.4) as a pre-reaction solution were added to a 96-well plate at the composition of the pre-reaction. A part of pre-reaction solution was transferred to another 96-well plate, and 1/10 diluted by K-Pi buffer solution containing a substrate. NADPH as a coenzyme was added to initiate a reaction as a marker reaction (no pre-reaction: preincubation 0 min). After a predetermined time of a reaction, a solution of methanol/acetonitrile=1/1 (V/V) was added to stop the reaction. In addition, NADPH was added to a remaining pre-reaction solution to initiate a pre-reaction (pre-reaction: preincubation 30 min). After a predetermined time of a pre-reaction, a part was transferred to another plate, and 1/10 diluted by K-Pi buffer solution containing a substrate to initiate a reaction as a marker reaction. After a predetermined time of a reaction, a solution of methanol/acetonitrile=1/1 (V/V) was added to stop the reaction. After each plate where the marker reaction has been performed was centrifuged at 3000 rpm for 15 minutes, 1-hydroxymidazolam in the centrifugation supernatant was quantified by LC/MS/MS.

Only a solvent DMSO used for dissolving the compound was added to the reaction solution instead of the compound of the present invention, and the mixture was used as a control (100%). Remaining activity (%) was calculated at the time of the addition of the compound of the present invention at each concentration, and IC value was calculated by inverse estimation based on a logistic model using the concentrations and the rates of inhibition. A shifted IC value is calculated from IC from the 0 min preincubation/IC from the 30-min preincubation. Shifted IC of 1.5 or more is graded as positive (+), and shifted IC of 1.0 or less is graded as negative (−).
(Results)
Compound II-37: (−)
Compound II-51: (−)

Test Example 5: BA Test

Materials and Methods for experiments to evaluate oral absorption
(1) Animals used: rats were used.
(2) Rearing conditions: the rats were allowed to freely take solid feed and sterilized tap water.
(3) Dose and grouping setting: a given dose was orally administered and intravenously administered. Groups were set as follows (dose was changed on a compound basis):
  Oral administration: 2 to 60 µmol/kg or 1 to 30 mg/kg (n=2 to 3)
  Intravenous administration: 1 to 30 µmol/kg or 0.5 to 10 mg/kg (n=2 or 3)
(4) Preparation of dosing solution: the test sample was administered as a solution or a suspension for the oral administration. Intravenous administration was performed after solubilization.
(5) Administration method: Oral administration was performed mandatory into the stomach by oral sonde. Intravenous administration was performed from the tail vein through a syringe with an injection needle.
(6) Evaluation item: blood was collected over time, and the concentration of the compound of the present invention in plasma was measured using LC/MS/MS.

(7) Statistical analysis: an area under concentration in plasma-time curve (AUC) was calculated as to change in the concentration of the compound of the present invention in plasma by the moment analysis method, and the bioavailability (BA) of the compound of the present invention was calculated from the dose ratio and AUC ratio between the oral administration group and the intravenous administration group.

Test Example 6: Clearance Evaluation Test

Experimental Material and Method
(1) Animals used: rats were used.
(2) Rearing conditions: the rats were allowed to freely take solid feed and sterilized tap water.
(3) Dose and grouping setting: a given dose was intravenously administered. Groups were set as follows:
Intravenous administration: 1 μmol/kg (n=2)
(4) Preparation of dosing solution: the test sample was solubilized using a solvent of dimethyl sulfoxide/propylene glycol=1/1 and administered.
(5) Administration method: the test sample was administered to the tail vein through a syringe with an injection needle.
(6) Evaluation item: blood was collected over time, and the concentration of the compound of the present invention in plasma was measured using LC/MS/MS.
(7) Statistical analysis: total body clearance (CLtot) and elimination half-life (t½) were calculated as to change in the concentration of the compound of the present invention in plasma by the moment analysis method.
(Results)
Compound II-13: 0.0226 mL/min/kg, 35.4 hr
Compound II-24: 0.0364 mL/min/kg, 23.6 hr Based on the above results, it was found that the compound of the present invention has a small clearance and a long elimination half-life, and is therefore useful as a long-acting integrase inhibitor.

Test Example 7: Metabolism Stability Test

Using commercially available pooled human liver microsomes, a compound of the present invention was reacted for a constant time, and a remaining rate was calculated by comparing a reacted sample and an unreacted sample, thereby, a degree at which the compound of the present invention was metabolized in liver was assessed.

A reaction was performed (oxidative reaction) at 37° C. for 0 minute or 30 minutes in the presence of 1 mmol/L NADPH in 0.2 mL of a buffer solution (50 mmol/L Tris-HCl pH 7.4, 150 mmol/L potassium chloride, 10 mmol/L magnesium chloride) containing 0.5 mg protein/mL of human liver microsomes. After the reaction, 50 μL of the reaction solution was added to 100 μL of a solution of methanol/acetonitrile=1/1 (v/v), and the mixture was mixed and centrifuged at 3000 rpm for 15 minutes. The compound of the present invention in the centrifugation supernatant was quantified by LC/MS/MS or solid-phase extraction (SPE)/MS. The amount of the compound of the present invention remaining after the reaction was calculated with the amount of the compound at 0 minutes of the reaction defined as 100%.
(Results) The residual rate of the compound at a concentration of 0.5 μmol/L is shown in the following table.

TABLE 9

| NO. | residual rate |
| --- | --- |
| I-002 | 93 |
| I-008 | 97.7 |
| I-012 | 72.2 |
| II-003 | 109 |
| II-010 | 106 |
| II-018 | 95.3 |
| II-023 | 98.3 |
| II-024 | 96.5 |
| II-027 | 90.5 |
| II-029 | 85.3 |
| II-033 | 81.3 |
| II-037 | 93.4 |
| II-038 | 92.4 |
| II-041 | 95.5 |
| II-043 | 103 |
| II-044 | 88.5 |
| II-046 | 97.2 |
| II-048 | 100 |
| II-050 | 103 |
| II-051 | 92.9 |
| II-052 | 83.4 |
| II-054 | 98.8 |
| II-055 | 93.9 |
| II-056 | 102 |
| II-057 | 82.5 |
| II-058 | 94.2 |
| II-061 | 91.5 |
| II-062 | 71.7 |
| II-063 | 96.5 |
| II-065 | 94.6 |
| II-067 | 93 |
| II-068 | 91.3 |
| II-069 | 102 |

Test Example 8: Fluctuation Ames Test

Mutagenicity of compounds of the present invention was evaluated. 20 μL of freezing-stored rat typhoid bacillus (Salmonella typhimurium TA98 strain, TA100 strain) was inoculated on 10 mL of a liquid nutrient medium (2.5% Oxoid nutrient broth No. 2), and this was cultured before shaking at 37° C. for 10 hours. 7.70 to 8.00 mL of a bacterial solution of the TA98 strain was centrifuged (2000×g, 10 minutes) to remove a culturing solution. Bacteria were suspended in a Micro F buffer solution ($K_2HPO_4$: 3.5 g/L, $KH_2PO_4$: 1 g/L, $(NH_4)_2SO_4$: 1 g/L, trisodium citrate dihydrate: 0.25 g/L, and $MgSO_4 \cdot 7H_2O$: 0.1 g/L) with the same volume as that of the bacterial solution used for centrifugation. The suspension was added to 120 mL of Exposure medium (Micro F buffer solution containing biotin: 8 μg/mL, histidine: 0.2 μg/mL, and glucose: 8 mg/mL). 3.10 to 3.42 mL of a bacterial solution of the TA100 strain was added to 120 to 130 mL of Exposure medium to prepare a test bacterial solution. Each 12 μL of DMSO solution of a compound of the present invention (several serial dilution from maximum dose 50 mg/mL at 2 to 3 fold ratio), DMSO as a negative control, and 50 μg/mL of 4-nitroquinoline-1-oxide DMSO solution for the TA98 strain, 0.25 μg/mL of 2-(2-furyl)-3-(5-nitro-2-furyl)acrylamide DMSO solution for the TA100 strain under the non-metabolism activating condition, 40 μg/mL of 2-aminoanthracene DMSO solution for the TA98 strain, 20 μg/mL of 2-aminoanthracene DMSO solution for the TA100 strain under the metabolism activating condition as a positive control, and 588 μL of the test bacterial solution (a mixed solution of 498 μl of the test bacterial solution and 90 μL of S9 mix under the metabolism activating condition) were mixed, and this was shaking-cultured at 37° C. for 90 minutes. 460 μL of the bacterial solution exposed to a compound of the present invention was mixed with 2300 μL of an Indicator medium (Micro F buffer solution containing biotin: 8 μg/mL, histidine: 0.2 μg/mL, glucose: 8 mg/mL, Bromo Cresol Purple: 37.5 μg/mL), each 50 μL was dispensed into microplate 48 wells/dose, and this was subjected to stationary culturing at 37° C. for 3 days. Since a well containing a bacterium which has obtained the proliferation ability by mutation of an amino acid (histidine) synthesizing enzyme gene turns from purple to yellow due to a pH change, the bacterium proliferation well which has turned to yellow in 48 wells per dose is counted, and was assessed by comparing with a negative control group. (−) means that mutagenicity is negative and (+) is positive.

Test Example 9: hERG Test

For the purpose of assessing risk of an electrocardiogram QT interval prolongation of the compound of the present invention, effects of the compound of the present invention on delayed rectifier K+ current ($I_{Kr}$), which plays an important role in the ventricular repolarization process, was studied using CHO cells expressing human ether-a-go-go related gene (hERG) channel.

After a cell was retained at a membrane potential of −80 mV by whole cell patch clamp method using a fully automated patch clamp system (QPatch; Sophion Bioscience A/S) and given a leak potential of −50 mV, $I_{Kr}$ induced by depolarization stimulation at +20 mV for 2 seconds and, further, repolarization stimulation at −50 mV for 2 seconds, was recorded. Extracellular solution (NaCl: 145 mmol/L, KCl: 4 mmol/L, $CaCl_2$): 2 mmol/L, MgCl2: 1 mmol/L, glucose: 10 mmol/L, HEPES (4-(2-hydroxyethyl)-1-piperazineethanesulfonic acid, 4-(2-hydroxyethyl)-1-piperazineethanesulfonic acid): 10 mmol/L, pH=7.4) adjusted to contain 0.1% dimethylsulfoxide is used as a medium. The extracellular solution in which the medium and the compound of the present invention had been dissolved at each objective concentration is applied to the cell for 7 minutes or more under conditions of room temperature. From the recording $I_{Kr}$, an absolute value of the tail peak current was measured based on the current value at the resting membrane potential using analysis software (QPatch Assay software; Sophion Bioscience A/S). Further, the tail peak current after application of the compound of the present invention relative to the tail peak current after application of the medium was calculated as a rate of inhibition to assess the influence of the compound of the present invention on $I_{Kr}$.

Test Example 10: Solubility Test

The solubility of the compound of the present invention was determined under conditions of 1% DMSO addition. A 10 mmol/L solution of the compound was prepared with DMSO. 2 μL of the solution of the compound of the present invention was added to 198 μL each of a JP-1 fluid and a JP-2 fluid. After shaking at room temperature for 1 hour, the mixed solutions were filtered by suction. The filtrates were diluted 10- or 100-fold with methanol/water=1/1 (V/V) or acetonitrile/methanol/water=1/1/2 (V/V/V), and concentrations in the filtrates were measured by the absolute calibration curve method using LC/MS or solid-phase extraction (SPE)/MS.

The composition of the JP-1 fluid is as below.

Water is added to 2.0 g of sodium chloride and 7.0 mL of hydrochloric acid to bring the amount to 1000 mL.

The composition of the JP-2 fluid is as below.

1 volume of water is added to 1 volume of the solution in which 3.40 g of potassium dihydrogen phosphate and 3.55 g of anhydrous disodium hydrogen phosphate are dissolved in water to bring the amount to 1000 mL.

Test Example 11: Powder Solubility Test

An appropriate amount of the compound of the present invention is placed in appropriate containers, and 200 μL of a JP-1 fluid (water is added to 2.0 g of sodium chloride and 7.0 mL of hydrochloric acid to bring the amount to 1000 mL), a JP-2 fluid (3.40 g of potassium dihydrogen phosphate and 3.55 g of dibasic sodium phosphate anhydrous are dissolved in water to bring the amount to 1000 mL, and to 1 volume of the resultant, 1 volume of water is added), or 20 mmol/L sodium taurocholate (TCA) in a JP-2 fluid (a JP-2 fluid is added to 1.08 g of TCA to bring the amount to 100 mL) was added to each container. When the whole amount was dissolved after the test solution addition, the compound of the present invention was appropriately further added. After the container was hermetically sealed and shaken for 1 hour at 37° C., the mixture was filtered and 100 μL of methanol was added to 100 μL of each filtrate (double dilution). The dilution ratio was changed according to the need. The absence of air bubbles and deposits was confirmed, and the containers were hermetically sealed and shaken. The compound of the present invention was quantified by the absolute calibration curve method using HPLC.

Test Example 12: Ames Test

The compound of the present invention is evaluated for its mutagenicity by the Ames test with *Salmonella typhimurium* TA98, TA100, TA1535 and TA1537 strains and an *Escherichia coli* WP2uvrA strain as test bacterial strains. 0.1 mL of a DMSO solution of the compound of the present invention is mixed with 0.5 mL of S9 mix under metabolic activation conditions or 0.5 mL of a phosphate buffer solution and 0.1 mL of each test bacterial solution under non-metabolic activation conditions, and the mixture is overlaid on a minimum glucose agar plate together with 2 mL of soft agar for overlay containing histidine and biotin, or tryptophan. At the same time therewith, a similar test is also conducted as to a negative control substance (DMSO) and a positive control substance (2-(2-furyl)-3-(5-nitro-2-furyl)acrylamide, sodium azide, 9-aminoacridine, or 2-aminoanthracene). After culture at 37° C. for 48 hours, revertant colonies that have appeared are counted and evaluated by comparison with the negative control group. When the number of revertant colonies increases in a concentration-dependent manner and becomes twice or more the number of colonies of the negative control group, positivity (+) is determined.

Test Example 13: Nav Test

For the purpose of assessing risk of proarrhythmia of the compound of the present invention, effects of the compound of the present invention on Na+ current ($I_{Na}$), which plays an important role in the myocardial depolarization process, was studied using HEK cells expressing Voltage gated sodium channel (Nav1.5 channel) encoded by SCN5A gene.

A cell was retained at a membrane potential of −100 mV by whole cell patch clamp method using a fully automated patch clamp system (QPatch; Sophion Bioscience A/S), and $I_{Na}$ induced by depolarization pulse stimulation at −10 mV for 20 ms was recorded. Extracellular solution (NaCl: 145 mmol/L, KCl: 4 mmol/L, $CaCl_2$) 2 mmol/L, MgCl2: 1 mmol/L, glucose: 10 mmol/L, HEPES (4-(2-hydroxyethyl)-1-piperazineethanesulfonic acid, 4-(2-hydroxyethyl)-1-piperazineethanesulfonic acid): 10 mmol/L, TEA (Tetraethylammonium Hydroxide): 10 mmol/L, pH=7.4) adjusted to contain 0.3% dimethylsulfoxide was used as a medium. The extracellular solution in which the medium and the compound of the present invention had been dissolved at each objective concentration was applied to the cell for 5 minutes or more under conditions of room temperature. From the recording $I_{Na}$, an absolute value of the maximum peak current was measured based on the current value at the resting membrane potential using analysis software (QPatch Assay software; Sophion Bioscience A/S). Further, the ratio of the maximum peak current when applying the compound of the present invention relative to the maximum peak current when applying the medium was calculated to assess the influence of the compound of the present invention on $I_{Na}$.

(Results)
Compound I-8: 103%
Compound I-2: 102%
Compound I-12: 97.1%
Compound II-3: 96.7%
Compound II-18: 109%
Compound II-23: 93.3%
Compound II-24: 89.3%
Compound II-37: 88.8%
Compound II-38: 86.2%
Compound II-41: 78.8%
Compound II-33: 90.7%

Based on the above results, no clear increase in current was observed, and it was found that the compound of the present invention is less likely to cause arrhythmia due to an increase in Na current.

Test Example 14: Anti-HIV Activity Evaluation Test Using Peripheral Blood Mononuclear Cells (PBMC) of a Healthy Subject Serial dilutions of a test sample were prepared in a 96-well microplate (50 μL/well). PBMC stimulated with $1.0 \times 10^5$ cells/well of Phytohemagglutinin (PHA) and an HIV virus solution were mixed for the required number of wells, and the mixture was reacted at 37° C. for 1 hour. After the reaction, the cell suspension was centrifuged and the supernatant discarded. The infected cells were dispersed in a culture solution for the required number of wells at 150 μL/well, and 150 μL/well was dispensed to a 96-well microplate containing a test sample. The plate was mixed with a plate mixer and cultured for 4 days in a C02 incubator. The reverse transcriptase activity in the culture solution was measured. A 90% HIV inhibitory concentration (EC90) was determined from a concentration-dependent curve using the following 4 parameter logistic curve fitting model.

$$y=A+((B\cdot A)/(1+(C/x)^D))$$

A=minimum rate of inhibition (negative control, 0%)
B=maximum rate of inhibition (positive control, 100%)
C=compound concentration at an inflection point
D=slope coefficient
x=compound concentration
y=rate of inhibition (%)
(Results)
Compound I-8: 1.0 nM
Compound II-23: 1.7 nM Test Example 15: Anti-HIV Activity Evaluation Test in the Presence of Human Serum Protein Serial dilutions of a test sample were prepared in a 96-well microplate (50 μL/well). A human serum protein solution (human serum protein concentration: 50%) was dispensed into a 96-well microplate containing a test sample in an amount of 100 μL/well, and left standing at room temperature for 1 hour. 100 μL/well of the culture solution was dispensed to a plate without serum. $3.0 \times 10^5$ cells/well of MT-4 cells and 3 μL/well of HIV virus solution were mixed for the required number of wells and the mixture was reacted at 37° C. for 1 hour. After the reaction, the cell suspension was centrifuged and the supernatant discarded. The infected cells were dispersed in a culture solution for the required number of wells at 50 μL/well, and 50 μL/well was dispensed to a 96-well microplate containing the test sample and human serum protein (human serum protein final concentration: 25%). The plate was mixed with a plate mixer and cultured for 4 days in a $CO_2$ incubator. An MTT (3-(4,5-dimethylthiazol-2-yl)-2,5-diphenyltetrazolium bromide) solution was dispensed at 30 μL/well. The plate was reacted for 1 hour in a $CO_2$ incubator. 150 μL of the supernatant was removed from each well so as not to take up the cells. 150 μL of a cell lysis solution was added to each well and well mixed with a plate mixer until the cells were completely lysed. The absorbance of the mixed plate was measured at two wavelengths of 560 nm and 690 nm using a microplate reader. A 50% HIV inhibitory concentration (EC50) was determined from a concentration-dependent curve using the following 4 parameter logistic curve fitting model.

$$y=A+((B\cdot A)/(1+(C/x)^D))$$

A=minimum rate of inhibition (negative control, 0%)
B=maximum rate of inhibition (positive control, 100%)
C=compound concentration at an inflection point
D=slope coefficient
x=compound concentration
y=rate of inhibition (%)
In addition, the potency shift (PS) was calculated based on the following calculation equation. Note that PS is an extrapolated value of a human serum protein concentration of 100%.

PS=4×(EC50 in the presence of 25% human serum protein/EC50 in the absence of human serum protein)

(Results)
The PS in the presence of human serum protein is shown in the table (100% extrapolated value).
Compound I-8: 116
Compound II-23: 56

Preparation Example

The compound of the present invention can be administered as a pharmaceutical composition through an arbitrary conventional route, particularly, enterally, for example, orally, in the form of, for example, a tablet or a capsule, parenterally in the form of, for example, an injection or a suspension, locally in the form of, for example, a lotion, a gel, an ointment or a cream, or in a transnasal form or a suppository form. A pharmaceutical composition comprising the compound of the present invention in a free form or in a pharmaceutically acceptable salt form together with at least one pharmaceutically acceptable carrier or diluent can be produced by a mixing, granulation or coating method according to a conventional method. For example, an oral composition can be prepared as a tablet, granules, or a capsule containing an excipient, a disintegrant, a binder, a lubricant, or the like and the active ingredient, etc. Also, an injectable composition can be prepared as a solution or a suspension and may be sterilized. The injectable composition may also contain a preservative, a stabilizer, a buffering agent, or the like.

INDUSTRIAL APPLICABILITY

The compound of the present invention has integrase inhibitory activity and/or cell growth inhibitory activity against a virus, particularly, HIV. Accordingly, the compound of the present invention is useful in the prevention or treatment of various diseases, virus infections (e.g., AIDS), and the like involving integrase.

The invention claimed is:

1. A compound represented by the following formula (I) or a pharmaceutically acceptable salt thereof:

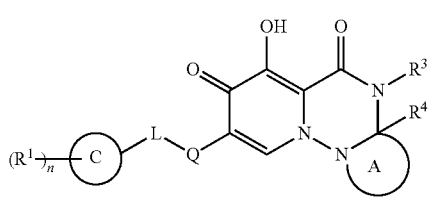

(I)

wherein
ring A is a substituted or unsubstituted non-aromatic heterocycle;
ring C is a benzene ring or a pyridine ring;
Q is a 5- or 6-membered aromatic heterocycle optionally substituted with one or more substituents selected from the group consisting of halogen, alkyl, haloalkyl, alkyloxy, haloalkyloxy, and alkylamino;
each $R^1$ is independently halogen, alkyl, haloalkyl, alkyloxy, cyano, or haloalkyloxy;
L is substituted or unsubstituted alkylene;
$R^3$ is substituted or unsubstituted alkyl, substituted or unsubstituted non-aromatic carbocyclyl, or substituted or unsubstituted non-aromatic heterocyclyl;
$R^4$ is hydrogen, or substituted or unsubstituted alkyl;
$R^3$ and $R^4$, or $R^3$ and a substituent on ring A may be taken together with the adjacent atoms to form a substituted or unsubstituted non-aromatic heterocycle; and
n is an integer of 1 to 3.

2. The compound according to claim 1 or a pharmaceutically acceptable salt thereof, wherein ring A is any of the following rings:

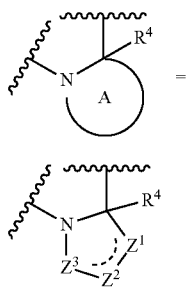

(a)

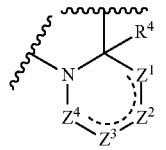

(b)

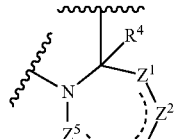

(c)

wherein
$R^4$ is hydrogen, or substituted or unsubstituted alkyl;
the broken line represents the presence or absence of a bond;
$Z^1$, $Z^2$, $Z^3$, $Z^4$ and $Z^5$ are each independently $CR^{5a}R^{5b}$, $CR^{5a}$, O, N, $NR^{5c}$, or S, wherein the number of heteroatoms forming the ring structure of the A ring in $Z^1$, $Z^2$, $Z^3$, $Z^4$ and $Z^5$ is 0 or 1;
$Z^1$ and $Z^3$, $Z^1$ and $Z^4$, $Z^1$ and $Z^5$, $Z^2$ and $Z^4$, $Z^2$ and $Z^5$, $Z^3$ and $Z^5$, $R^4$ and $Z^2$, $R^4$ and $Z^3$, $R^4$ and $Z^4$ or $R^4$ and $Z^5$ may be taken together to form a substituted or unsubstituted C1-C4 cross-link optionally interrupted by one heteroatom selected from the group consisting of $NR^{5c}$, O and S;
$R^{5a}$ and $R^{5b}$ are each independently hydrogen, halogen, hydroxy, substituted or unsubstituted alkyl, or substituted or unsubstituted alkyloxy;
$R^{5a}$ and $R^{5b}$ on the same carbon atom may be taken together to form a substituted or unsubstituted non-aromatic carbocycle, or a substituted or unsubstituted non-aromatic heterocycle;
$R^{5c}$ is hydrogen, substituted or unsubstituted alkyl, substituted or unsubstituted alkylcarbonyl, substituted or unsubstituted alkyloxycarbonyl, substituted or unsubstituted carbamoyl, substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl; and
$R^3$ and $R^4$ may be taken together with the adjacent atoms to form a substituted or unsubstituted non-aromatic heterocycle.

3. The compound according to claim 1 or a pharmaceutically acceptable salt thereof, wherein ring A is any of the following rings:

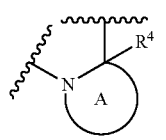

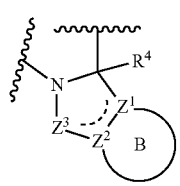

(a1)

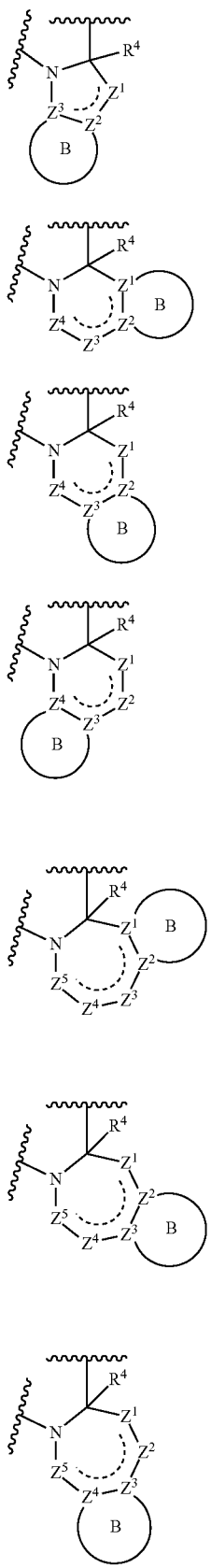

wherein
R⁴ is hydrogen, or substituted or unsubstituted alkyl;
the broken line represents the presence or absence of a bond;
ring B is a substituted or unsubstituted carbocycle or a substituted or unsubstituted heterocycle;
$Z^1$, $Z^2$, $Z^3$, $Z^4$ and $Z^5$ are each independently $CR^{5a}R^{5b}$, $CR^{5a}$, C, O, N, $NR^{5c}$, or S (provided that an atom constituting ring B is $CR^{5a}$, C or N);
$Z^1$ and $Z^3$, $Z^1$ and $Z^4$, $Z^1$ and $Z^5$, $Z^2$ and $Z^4$, $Z^2$ and $Z^5$, $Z^3$ and $Z^5$, $R^4$ and $Z^2$, $R^4$ and $Z^3$, $R^4$ and $Z^4$ or $R^4$ and $Z^5$ may be taken together to form a substituted or unsubstituted C2-C4 cross-link optionally interrupted by one heteroatom selected from the group consisting of $NR^{5c}$, O and S;
$R^{5a}$ and $R^{5b}$ are each independently hydrogen, halogen, substituted or unsubstituted alkyl, or substituted or unsubstituted alkyloxy;
$R^{5a}$ and $R^{5b}$ on the same carbon atom may be taken together to form a substituted or unsubstituted non-aromatic carbocycle, or a substituted or unsubstituted non-aromatic heterocycle;
$R^{5c}$ is hydrogen, substituted or unsubstituted alkyl, substituted or unsubstituted alkylcarbonyl, substituted or unsubstituted alkyloxycarbonyl, substituted or unsubstituted carbamoyl, substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl; and
$R^3$ and $R^4$ may be taken together with the adjacent atoms to form a substituted or unsubstituted non-aromatic heterocycle.

4. The compound according to claim 1 or a pharmaceutically acceptable salt thereof, wherein the compound is represented by the following formula (II):

wherein
ring A is any of the following rings;

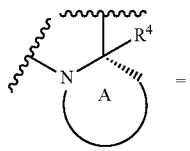

(a2)

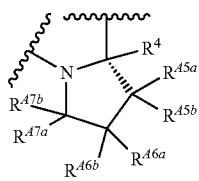

(b2)

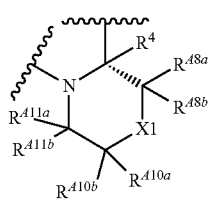

X1 is $CR^{A9a}R^{A9b}$ or O;
$R^{A5a}$, $R^{A5b}$, $R^{A6a}$, $R^{A6b}$, $R^{A7a}$ and $R^{A7b}$ are each independently hydrogen, alkyl, alkyloxy or alkyloxyalkyl;
$R^{A5a}$ and $R^{A6a}$, or $R^{A6a}$ and $R^{A7a}$ may be taken together with the adjacent atoms to form an aromatic carbocycle optionally substituted with halogen, a 3- to 6-membered non-aromatic carbocycle optionally substituted with halogen or a 4- to 6-membered non-aromatic heterocycle optionally substituted with halogen (provided that $R^{A5b}$ and $R^{A6b}$, or $R^{A6b}$ and $R^{A7b}$ are taken together to form a bond when forming an aromatic carbocycle);
$R^{A5b}$ and $R^{A6b}$ may be taken together to form a bond;
$R^{A8a}$, $R^{A8b}$, $R^{A9a}$, $R^{A9b}$, $R^{A10a}$, $R^{A10b}$, $R^{A11a}$ and $R^{A11b}$ are each independently hydrogen, alkyl, alkyloxy or alkyloxyalkyl;
$R^{A8a}$ and $R^{A10a}$ may be taken together to form a C1-C3 cross-link;
$R^{A10a}$ and $R^{A11a}$ may be taken together with the adjacent atoms to form a 5-membered non-aromatic carbocycle;
$R^{A9a}$ and $R^{A9b}$ may be taken together with the adjacent atoms to form a 4-membered non-aromatic carbocycle or a 5-membered non-aromatic heterocycle;
$R^{A8a}$ s a and $R^{A9a}$ may be taken together to form a bond;
ring C is a benzene ring or a pyridine ring;
Q is a 5-membered aromatic heterocycle;
each $R^1$ is independently halogen, alkyl, haloalkyl, alkyloxy, cyano, or haloalkyloxy;
$R^{2a}$ and $R^{2b}$ are each independently hydrogen, alkyl, or haloalkyl;
$R^3$ is alkyl or haloalkyl;
$R^4$ is hydrogen or alkyl; and
n is an integer of 1 to 3.

5. The compound according to claim 1 or a pharmaceutically acceptable salt thereof, wherein $R^3$ is alkyl or haloalkyl.

6. The compound according to claim 1 or a pharmaceutically acceptable salt thereof, wherein $R^3$ is alkyl.

7. The compound according to claim 1 or a pharmaceutically acceptable salt thereof, wherein $R^4$ is hydrogen or alkyl.

8. The compound according to claim 1 or a pharmaceutically acceptable salt thereof, wherein each $R^1$ is independently halogen, alkyl, or haloalkyl.

9. The compound according to claim 1 or a pharmaceutically acceptable salt thereof, wherein each $R^1$ is independently halogen.

10. The compound according to claim 1 or a pharmaceutically acceptable salt thereof, wherein —L— is —$CR^{2a}R^{2a}$—, $R^{2a}$ is hydrogen and $R^{2b}$ is hydrogen or alkyl, or $R^{2a}$ and $R^{2b}$ are taken together with the adjacent carbon atom to form a C3-C4 carbocycle.

11. The compound according to claim 4 or a pharmaceutically acceptable salt thereof, wherein $R^{2a}$ is hydrogen, and $R^{2b}$ is hydrogen or alkyl.

12. The compound according to claim 1 or a pharmaceutically acceptable salt thereof, wherein Q is a 5-membered aromatic heterocycle.

13. The compound according to claim 1 or a pharmaceutically acceptable salt thereof, wherein the carbon atom adjacent to $R^4$ has the following configuration:

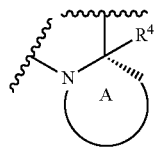

wherein ring A and $R^4$ are as defined in claim 1.

14. The compound according to claim 1 or a pharmaceutically acceptable salt thereof, wherein the compound is selected from the group consisting of compounds I-2, I-6 and I-8

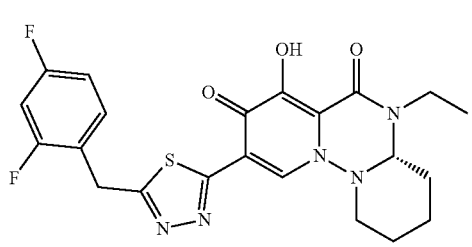

I-2

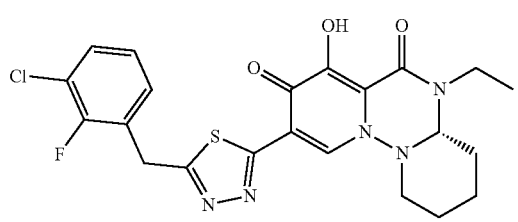

I-6 and

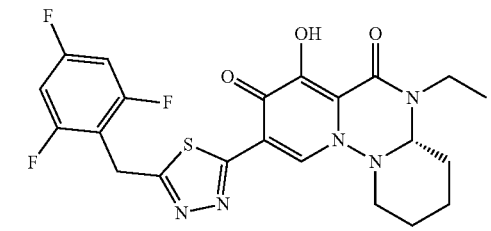

I-8

.

15. The compound according to claim 1 or a pharmaceutically acceptable salt thereof, wherein the compound is selected from the group consisting of compounds II-3, II-18, II-23, II-24, II-27, II-29, II-33, II-37, II-38, II-44, II-48, II-50, II-51, II-52, II-54, II-55, II-56, II-57, II-58, II-61, II-62, II-63, II-65, II-67 and II-68:
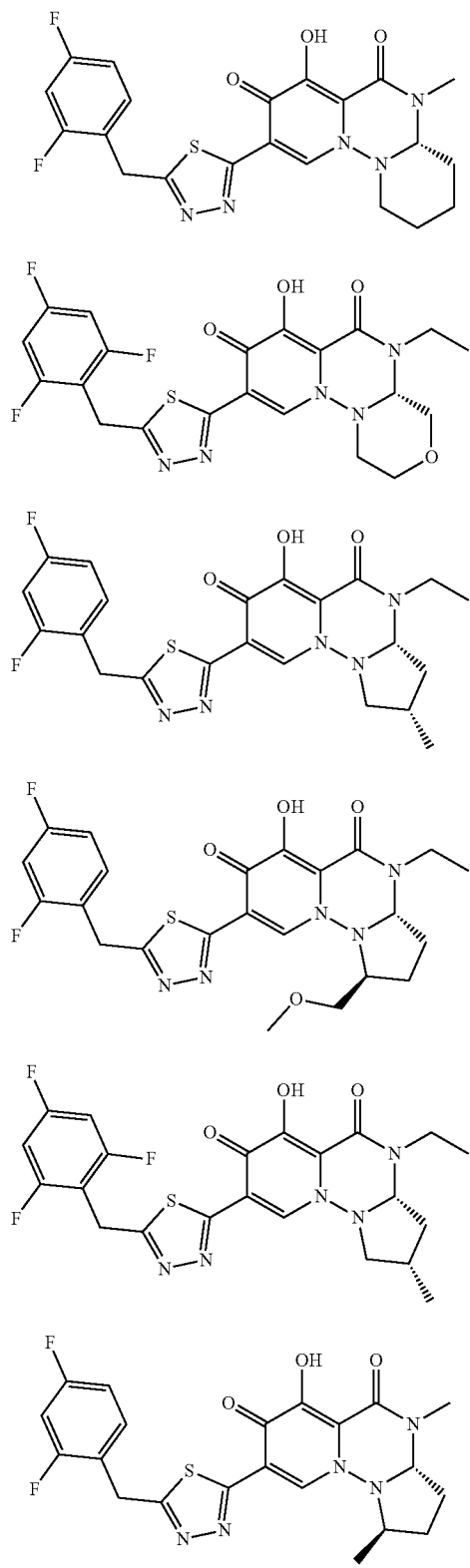
-continued
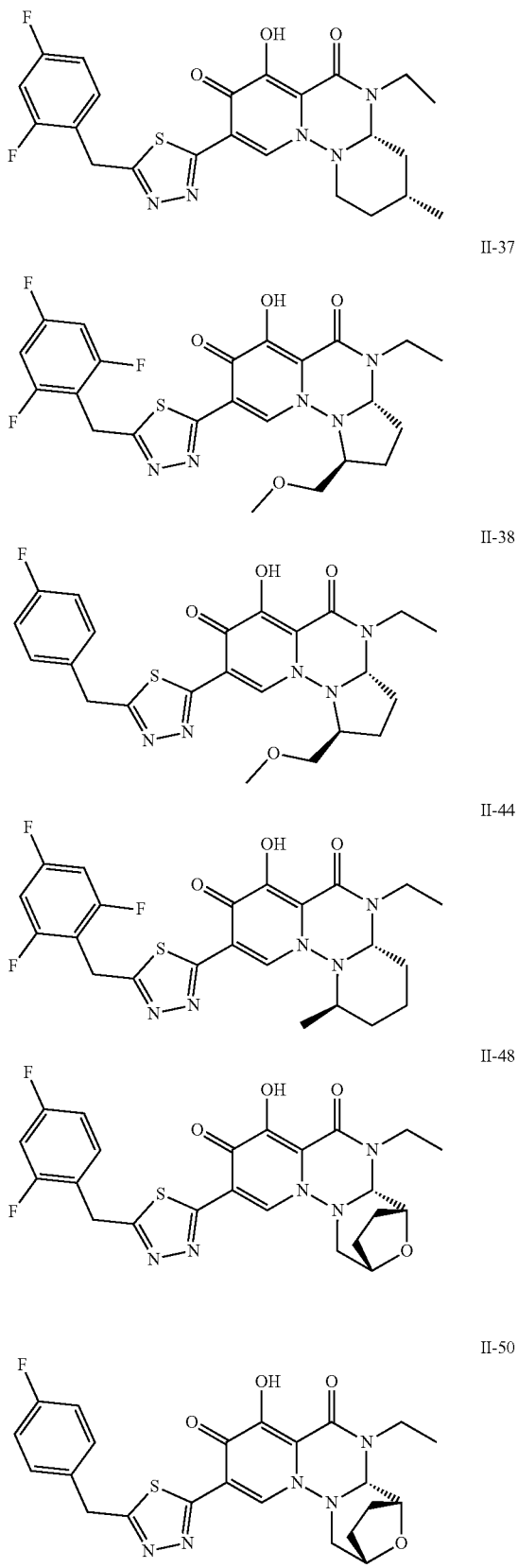

II-51
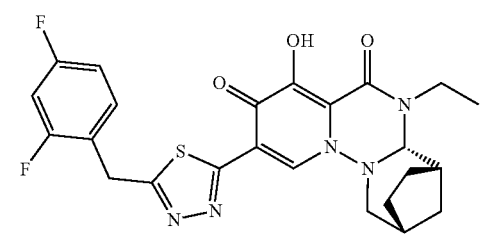
II-52
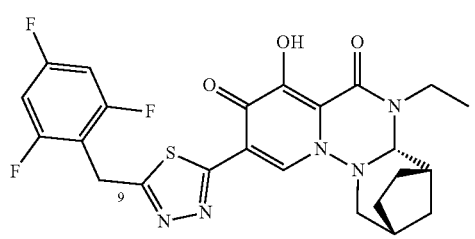
II-54
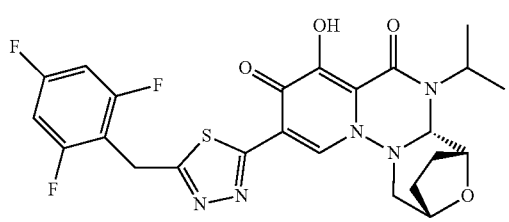
II-55
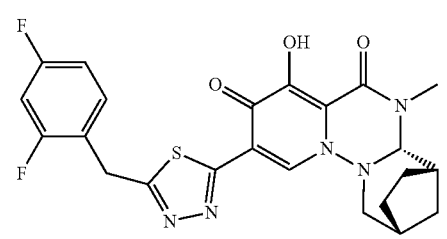
II-56
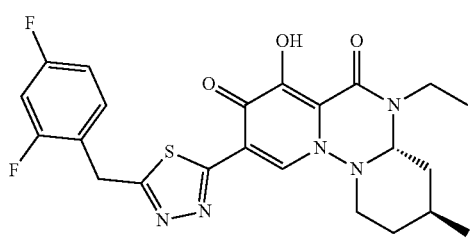
II-57
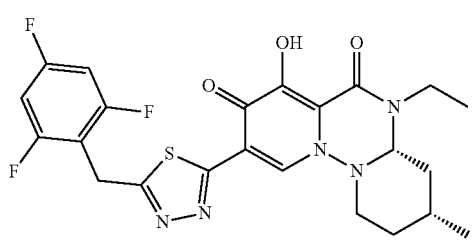
II-58
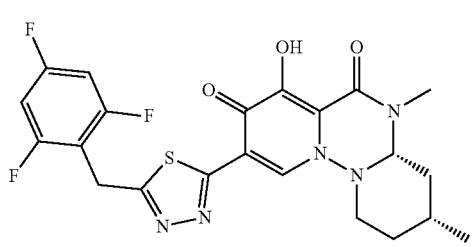
II-61
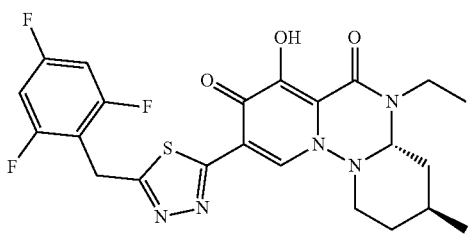
II-62
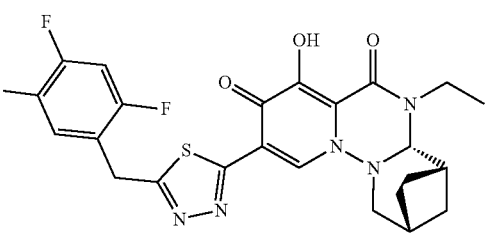
II-63
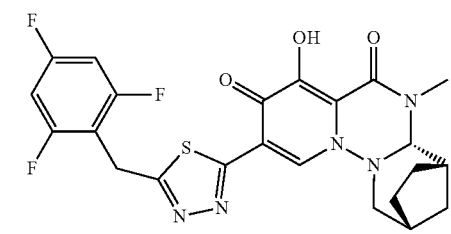
II-65
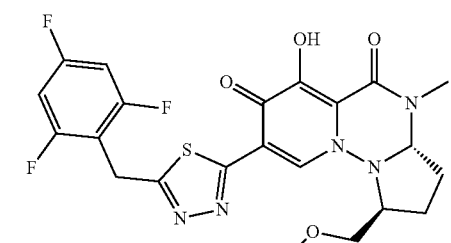
II-67
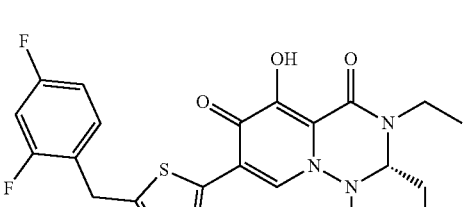
and
II-68
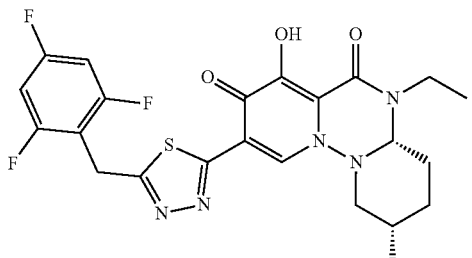
16. A pharmaceutical composition comprising the compound according to claim 1 or a pharmaceutically acceptable salt thereof, and a pharmaceutically acceptable additive, carrier or diluent.

17. The pharmaceutical composition according to claim 16, wherein the pharmaceutical composition is an anti-HIV agent.

18. A method for treating HIV infection comprising administering an effective amount of the compound according to claim 1, or a pharmaceutically acceptable salt thereof.

* * * * *

UNITED STATES PATENT AND TRADEMARK OFFICE
CERTIFICATE OF CORRECTION

PATENT NO. : 11,453,669 B2  
APPLICATION NO. : 17/058260  
DATED : September 27, 2022  
INVENTOR(S) : Yoshiyuki Taoda Page 1 of 1

It is certified that error appears in the above-identified patent and that said Letters Patent is hereby corrected as shown below:

In the Claims

Claim 10, Column 78, Line 9:
"—$CR^{2a}R^{2a}$—," should be deleted, and
-- —$CR^{2a}R^{2b}$—, -- should be added.

Signed and Sealed this  
Twenty-ninth Day of November, 2022

Katherine Kelly Vidal  
*Director of the United States Patent and Trademark Office*